US012403216B2

(12) United States Patent
Hasturk et al.

(10) Patent No.: US 12,403,216 B2
(45) Date of Patent: Sep. 2, 2025

(54) CHEMICAL MODIFICATION OF SILK FIBROIN FOR FABRICATION OF ENZYMATICALLY CROSSLINKED HYDROGELS WITH TUNABLE GELATION KINETICS AND BIOACTIVITY

(71) Applicant: Trustees of Tufts College, Medford, MA (US)

(72) Inventors: Onur Hasturk, Medford, MA (US); Jaewon Choi, Cambridge, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 182 days.

(21) Appl. No.: 17/768,876

(22) PCT Filed: Oct. 19, 2020

(86) PCT No.: PCT/US2020/056386
§ 371 (c)(1),
(2) Date: Apr. 14, 2022

(87) PCT Pub. No.: WO2021/077116
PCT Pub. Date: Apr. 22, 2021

(65) Prior Publication Data
US 2024/0082459 A1 Mar. 14, 2024

Related U.S. Application Data

(60) Provisional application No. 62/923,128, filed on Oct. 18, 2019.

(51) Int. Cl.
*A61L 27/22* (2006.01)
*A61L 27/36* (2006.01)
*A61L 27/52* (2006.01)

(52) U.S. Cl.
CPC ......... *A61L 27/227* (2013.01); *A61L 27/3604* (2013.01); *A61L 27/52* (2013.01)

(58) Field of Classification Search
CPC ..... A61L 27/227; A61L 27/3604; A61L 27/52
See application file for complete search history.

(56) References Cited

U.S. PATENT DOCUMENTS

2010/0056438 A1* 3/2010 Scheibel ............... A61K 8/11
530/422
2019/0247547 A1 8/2019 Le et al.
2019/0282731 A1 9/2019 Raia et al.

FOREIGN PATENT DOCUMENTS

WO 2009148405 A1 12/2009
WO WO 2018/225049 A1 * 12/2018
WO 2021077116 A1 4/2021

OTHER PUBLICATIONS

Zhan et al. Cyclic RGD conjugated poly(ethylene glycol)-co-poly(lactic acid) micelle enhances paclitaxel anti-glioblastoma effect, Journal of Controlled Release, vol. 143, Issue 1, Apr. 2, 2010, pp. 136-142. (Year: 2010).*

(Continued)

*Primary Examiner* — Hong Yu
(74) *Attorney, Agent, or Firm* — GTC Law Group PC & Affiliates

(57) ABSTRACT

Tyramine-substituted silk fibroin compositions as well as methods for making and using the same are provided.

20 Claims, 19 Drawing Sheets

(56) References Cited

OTHER PUBLICATIONS

Riberiro et al.: Rapidly responsive silk fibroin hydrogels as an artificial matrix for the programmed tumor cells death, PLoS One, Apr. 4, 2018;13(4) (Year: 2018).*
Hasturk, et al., "Enzymatically crosslinked silk and silk-gelatin hydrogels with tunable gelation kinetics, mechanical properties and bioactivity for cell culture and encapsulation", Biomaterials. Dec. 23, 2019 (Dec. 23, 2019) vol. 232, p. 119720; entire document, 2021, 41 pages.
PCT/US2020/056386, "International Application Serial No. PCT/US2020/056386, International Preliminary Report on Patentability mailed Apr. 19, 2022", Tufts University, 9 pages.
PCT/US2020/056386, "International Application Serial No. PCT/US2020/056386, International Search Report and Written Opinion mailed Mar. 23, 2021", Tufts University, 12 pages.
Raia, et al., "Enzymatically crosslinked silk-hyaluronic acid hydrogels", Biomaterials. Mar. 27, 2017 (Mar. 27, 2017) vol. 131, p. 58-67; p. 58, abstract, p. 59, right col, para 2, p. 60, right col, para 4, Mar. 27, 2017, 6 pages.

* cited by examiner

FIGS. 7A-7D
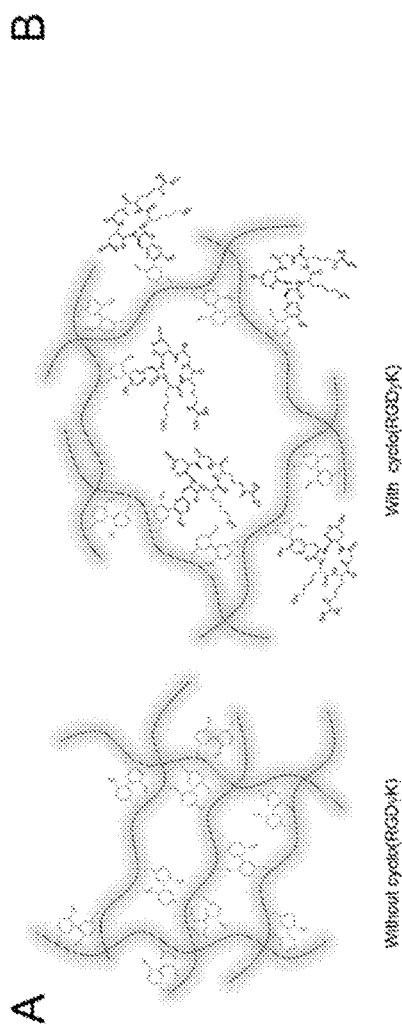
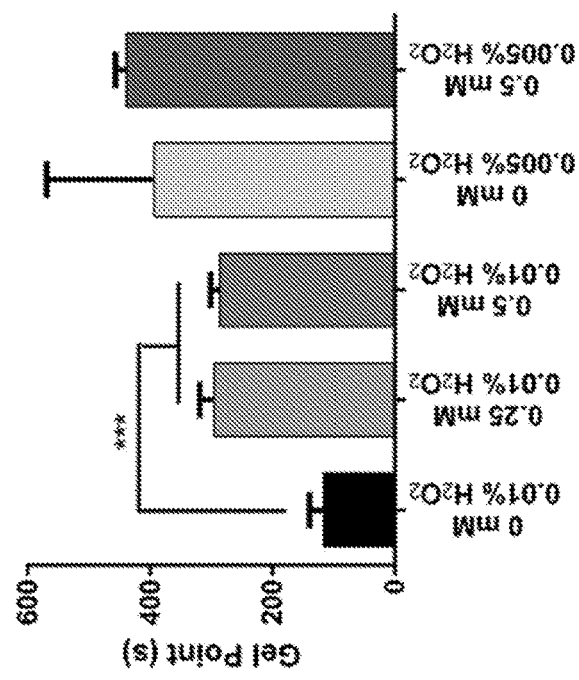
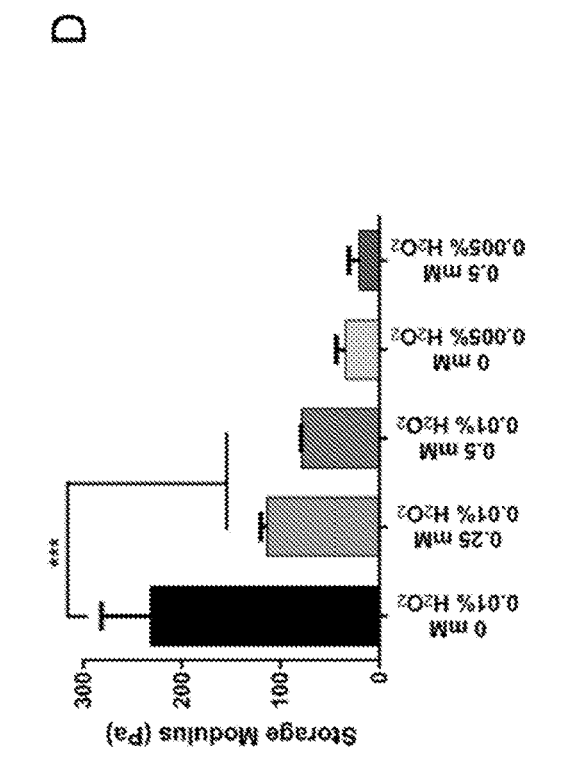

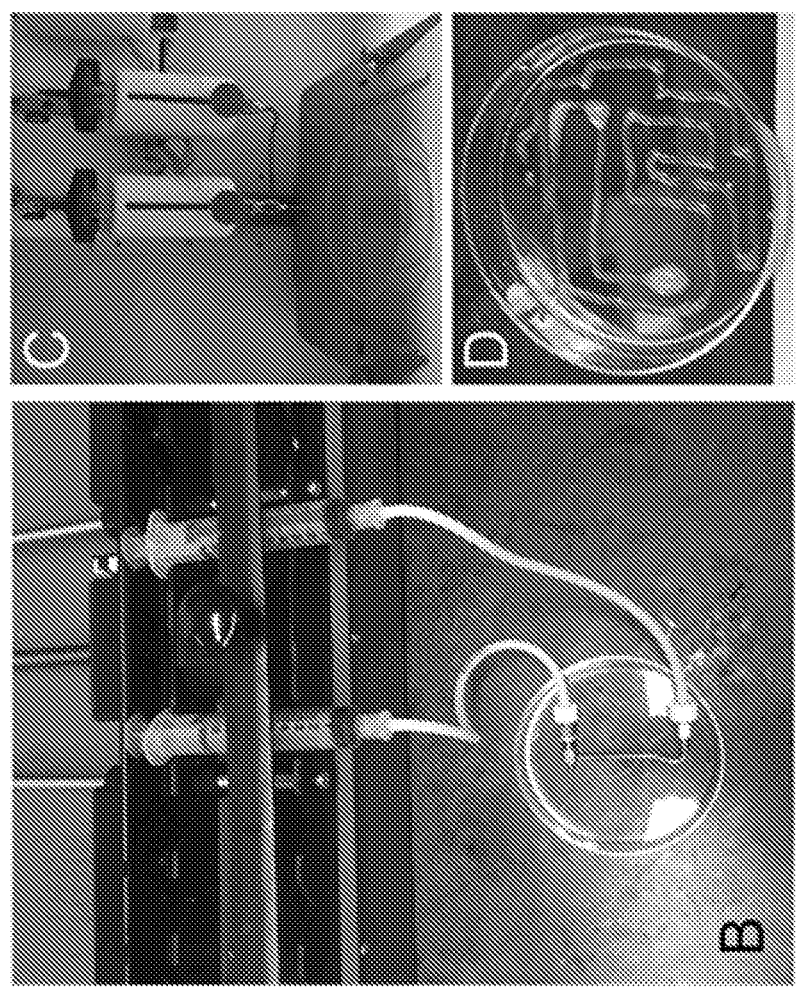
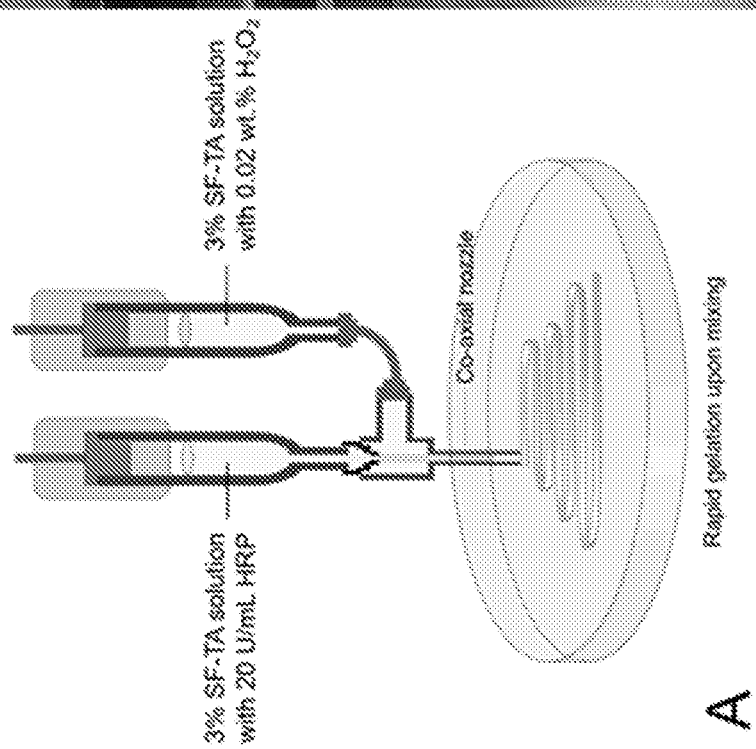
FIGS. 8A-8D

CHEMICAL MODIFICATION OF SILK FIBROIN FOR FABRICATION OF ENZYMATICALLY CROSSLINKED HYDROGELS WITH TUNABLE GELATION KINETICS AND BIOACTIVITY

CROSS-REFERENCE TO RELATED APPLICATIONS

This application claims benefit of and is a continuation of International Patent Application No. PCT/US2020/056386, filed Oct. 19, 2020, and entitled "CHEMICAL MODIFICATION OF SILK FIBROIN FOR FABRICATION OF ENZYMATICALLY CROSSLINKED HYDROGELS WITH TUNABLE GELATION KINETICS AND BIOACTIVITY," International Pub. No. WO2021077116, which is hereby incorporated by reference in its entirety for all purposes.

International Patent Application No. PCT/US2020/056386 claims the benefit of priority of U.S. Provisional Patent Application Ser. No. 62/923,128 filed on Oct. 18, 2019, the contents of which are hereby incorporated by reference herein.

STATEMENT REGARDING FEDERALLY SPONSORED RESEARCH

This invention was made with government support under grant number FA9550-17-1-0333 awarded by the United States Air Force and grant EB002520 awarded by the National Institutes of Health. The government has certain rights in this invention.

BACKGROUND

Hydrogels are three-dimensional (3D) polymeric networks with high water retention capacity and tunable physical, chemical and mechanical properties. They have been of great interest as scaffold materials in tissue engineering applications to guide cell growth and allow deposition of new extracellular matrix (ECM) while gradually degrading in the body until the original tissue architecture is restored[1]. Hydrogel-based materials have been proposed as injectable tissue fillers[2], bioinks for 3D bioprinting of artificial tissue and organ constructs with high spatial resolution, a wide range of shapes, structures and mechanical properties[3-5]; and delivery of encapsulated therapeutics and/or cells[6-9] in microscale particles with efficient diffusion rates and material-to-cell volume ratios[10-13] that allow for fabrication of tunable cell microenvironments.

One of the most commonly used rapidly gelling hydrogel system has been the ionically crosslinked polysaccharide alginate[14-16], which has very limited stability at physiological conditions due to the ongoing ion exchange mechanisms and their structural and mechanical integrities have been shown to deteriorate very quickly[17, 18]. Silk fibroin (SF) extracted from the cocoons of the domesticated silkworm Bombyx mori is a natural protein with biocompatibility, biodegradation and excellent mechanical properties owing to natural self-assembly[19]. Moreover, the high crystalline content of silk-based biomaterials provides slower degradation compared to other common biopolymers such as collagen/gelatin, elastin or HA, which rapidly degrade in vivo[20].

Aqueous SF solutions can be covalently crosslinked in the presence of horseradish peroxidase (HRP) and hydrogen peroxide ($H_2O_2$) through the formation of dityrosine bridges[21], and the mild crosslinking conditions were shown to be suitable for cell encapsulation and result in highly elastic hydrogels[22-24]. Although slow degradation and long-term structural stability[20] of silk hold promise as an alternative hydrogel system, HRP-mediated crosslinking of SF solution prepared in physiological buffers is significantly slower due to relatively higher ionic strength compared to distilled water, and it results in mechanically weaker hydrogels[25]. This limits the use of enzymatically crosslinked silk hydrogels as injectable tissue fillers, bioinks in 3D bioprinting or in microfluidic cell encapsulation, where rapid gelation is desired[26-28]. Moreover, lack of integrin-binding sequences in the primary structure of SF from B. mori[29] may result in poor cell-matrix interactions[22, 25, 30]. Therefore, a need exists for improved SF hydrogels.

SUMMARY OF THE INVENTION

In a first aspect, provided herein is a composition comprising tyramine-substituted silk fibroin, wherein a first phenol group of the tyramine-substituted silk fibroin is covalently crosslinked to a second phenol group of the tyramine-substituted silk fibroin. In some embodiments, the tyramine-substituted silk fibroin is selected from the group consisting of silkworm silk fibroin, spider silk fibroin, and recombinant silk fibroin. In some embodiments, total phenol content of the tyramine-substituted silk fibroin is at least 15% higher than total phenol content of unmodified silk fibroin. In some embodiments, the total phenol content of the tyramine-substituted silk fibroin is at least 6.0 mol %. In some embodiments, the total phenol content of the tyramine-substituted silk fibroin is at least 6.2 mol %.

In some embodiments, the composition further comprises unsubstituted silk fibroin; wherein at least one tyrosine of the unsubstituted silk fibroin is covalently crosslinked to at least one phenol group of the tyramine-substituted silk fibroin. In some embodiments, the ratio of unsubstituted silk fibroin to tyramine-substituted fibroin is in the range of 15:1 to 1:15. In some embodiments, the ratio of unsubstituted silk fibroin to tyramine-substituted fibroin is in the range of 15:1 to 1:2.

In some embodiments, the tyramine-substituted silk fibroin is created by a method comprising contacting a silk fibroin solution with tyramine hydrochloride in the presence of 1-ethyl-3-(-3-dimethylaminopropyl) carbodiimide hydrochloride and N-hydroxysuccinimide. In some embodiments, the silk fibroin solution is an aqueous silk fibroin solution.

In some embodiments, the composition additionally comprises at least one cyclic arginine-glycine-aspartic acid (RGD) peptide covalently linked to at least one phenol group of the tyramine-substituted silk fibroin. In some embodiments, the cyclic RGD peptide is a cyclic arginine-glycine-aspartic acid-tyrosine-lysing peptide (cyclo (RGDyK)). In some embodiments, the cyclo(RGDyK) peptide has the structure of formula I:

Formula I

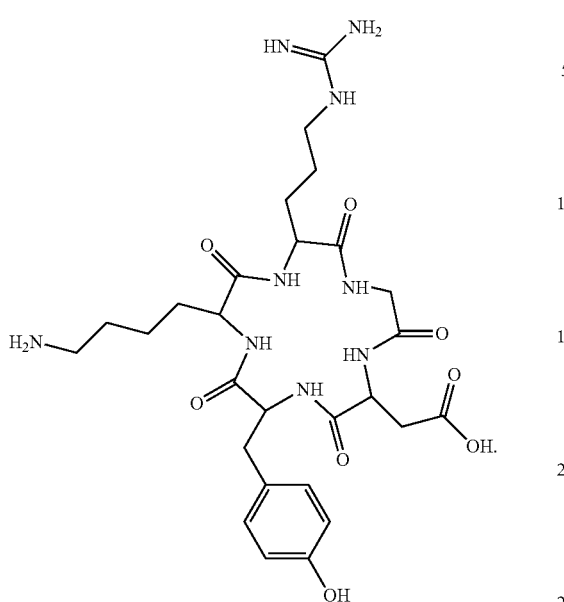

In some embodiments, the composition is biocompatible. In some embodiments, the composition is or comprises a hydrogel. In some embodiments, the composition further comprises at least one active agent. In some embodiments, the active agent is selected from the group consisting of neurotransmitters, hormones, intracellular signal transduction agents, pharmaceutically active agents, toxic agents, agricultural chemicals, chemical toxins, biological toxins, microbes, neurons, liver cells, immune system cells, vitamins, sedatives, hypnotics, prostaglandins and radiopharmaceuticals.

In some embodiments, the tyramine-substituted silk fibroin is present in an amount between about 0.5 wt. % and 10 wt. % based on total weight of the composition. In some embodiments, the unsubstituted silk fibroin is present in an amount between about 0.5 wt. % and 10 wt. % based on total weight of the composition. In some embodiments, the crosslinking is or comprises multi-phenol covalent crosslinks. In some embodiments, the multi-phenol crosslinks are selected from the group consisting of di-tyrosine crosslinks, di-tyramine crosslinks, and tyrosine-tyramine crosslinks.

In a second aspect provided herein is a composition comprising unsubstituted silk fibroin and tyramine-substituted silk fibroin, wherein at least one tyrosine-group of the unsubstituted silk fibroin is covalently crosslinked to at least one phenol-group of the tyramine-substituted silk fibroin. In some embodiments, the tyramine-substituted silk fibroin is selected from the group consisting of silkworm silk fibroin, spider silk fibroin, and recombinant silk fibroin. In some embodiments, total phenol content of the tyramine-substituted silk fibroin is at least 15% higher than total phenol content of unmodified silk fibroin. In some embodiments, the total phenol content of the tyramine-substituted silk fibroin is at least 6.0 mol %. In some embodiments, the total phenol content of the tyramine-substituted silk fibroin is at least 6.2 mol %. In some embodiments, the ratio of unsubstituted silk fibroin to tyramine-substituted silk fibroin is in the range of 15:1 to 1:15. In some embodiments, the ratio of unsubstituted silk fibroin to tyramine-substituted silk fibroin is in the range of 15:1 to 1:2. In some embodiments, the tyramine-substituted silk fibroin is created by a method comprising contacting a silk fibroin solution with tyramine hydrochloride in the presence of 1-ethyl-3-(-3-dimethylaminopropyl) carbodiimide hydrochloride and N-hydroxysuccinimide. In some embodiments, the silk fibroin solution is an aqueous silk fibroin solution.

In some embodiments, the composition additionally comprising at least one cyclic arginine-glycine-aspartic acid (RGD) peptide covalently linked to at least one phenol group of the tyramine-substituted silk fibroin. In some embodiments, the cyclic RGD peptide is a cyclic arginine-glycine-aspartic acid-tyrosine-lysing peptide (cyclo(RGDyK)). In some embodiments, the cyclo(RGDyK) peptide has the structure of formula I:

Formula I

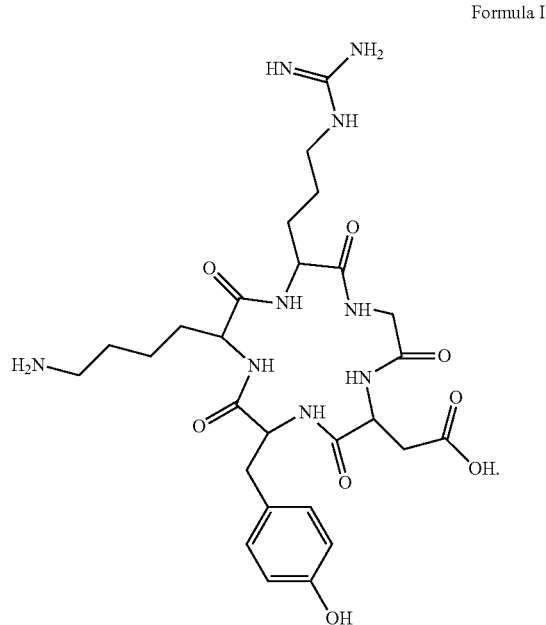 [SMILES: N=C(N)NCCCC1NC(=O)C(CCCCN)NC(=O)C(Cc2ccc(O)cc2)NC(=O)C(CC(=O)O)NC(=O)CNC1=O]

In some embodiments, the composition is biocompatible. In some embodiments, the composition is or comprises a hydrogel. In some embodiments, the composition further comprises at least one active agent. In some embodiments, the active agent is selected from the group consisting of neurotransmitters, hormones, intracellular signal transduction agents, pharmaceutically active agents, toxic agents, agricultural chemicals, chemical toxins, biological toxins, microbes, neurons, liver cells, immune system cells, vitamins, sedatives, hypnotics, prostaglandins and radiopharmaceuticals. In some embodiments, the tyramine-substituted silk fibroin is present in an amount between about 0.5 wt. % and 10 wt. % based on total weight of the composition. In some embodiments, the unsubstituted silk fibroin is present in an amount between about 0.5 wt. % and 10 wt. % based on total weight of the composition. In some embodiments, the crosslinking is or comprises multi-phenol covalent crosslinks. In some embodiments, the multi-phenol crosslinks are selected from the group consisting of di-tyrosine crosslinks, di-tyramine crosslinks, and tyrosine-tyramine crosslinks. In some embodiments, total amount of the tyramine-substituted silk fibroin and the unsubstituted silk fibroin present in the composition is between 0.5 wt. % and 10 wt. %.

In a third aspect, provided herein is a method comprising contacting a solution comprising unsubstituted silk fibroin and tyramine-substituted silk fibroin with an enzyme and a substrate for the enzyme, wherein a covalent crosslink between at least one tyrosine group in the unsubstituted silk fibroin and at least one phenol-group of the tyramine-substituted silk fibroin is formed. In some embodiments, the enzyme is selected from the group consisting of tyrosinase, laccase, a microperoxidase, soy bean peroxidase, myeloperoxidase, lactoperoxidase, eosinophil peroxidase, thyroid peroxidase, prostaglandin H synthase, and horseradish peroxidase. In some embodiments, the substrate is a peroxide selected from the group consisting of hydrogen peroxide, barium peroxide, calcium peroxide, sodium peroxide, organic peroxides and combinations thereof. In some embodiments, the enzyme is horseradish peroxidase and the substrate is hydrogen peroxide. In some embodiments, the solution is free of organic solvents and toxic materials. In some embodiments, the solution further comprises a cyclic RGD peptide. In some embodiments, the cyclic RGD peptide is a cyclic arginine-glycine-aspartic acid-tyrosine-lysing peptide (cyclo(RGDyK)). In some embodiments, the cyclo(RGDyK) peptide has the structure of formula I:

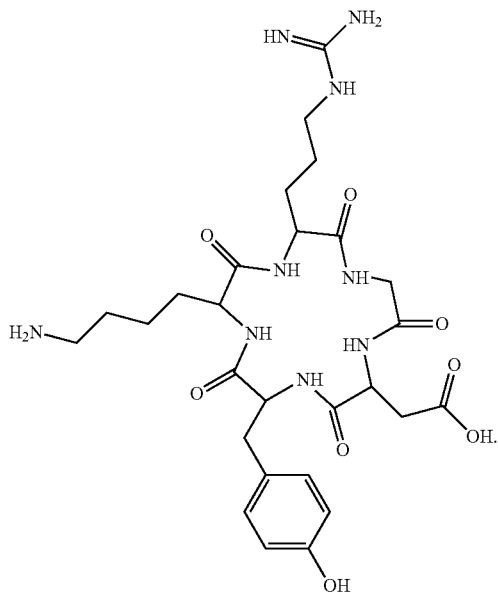

Formula I

In a forth aspect, provided herein is a method comprising contacting a solution comprising tyramine-substituted silk fibroin with an enzyme and a substrate for the enzyme, wherein a covalent crosslink between a first phenol group in the tyramine-substituted silk fibroin and a second phenol-group of the tyramine-substituted silk fibroin is formed. In some embodiments, the enzyme is selected from the group consisting of tyrosinase, laccase, a microperoxidase, soy bean peroxidase, myeloperoxidase, lactoperoxidase, eosinophil peroxidase, thyroid peroxidase, prostaglandin H synthase, and horseradish peroxidase. In some embodiments, the substrate is a peroxide selected from the group consisting of hydrogen peroxide, barium peroxide, calcium peroxide, sodium peroxide, organic peroxides and combinations thereof. In some embodiments, the enzyme is horseradish peroxidase and the substrate is hydrogen peroxide. In some embodiments, the solution is free of organic solvents and toxic materials. In some embodiments, the solution further comprises a cyclic RGD peptide. In some embodiments, the cyclic RGD peptide is a cyclic arginine-glycine-aspartic acid-tyrosine-lysing peptide (cyclo(RGDyK)). In some embodiments, the cyclo(RGDyK) peptide has the structure of formula I:

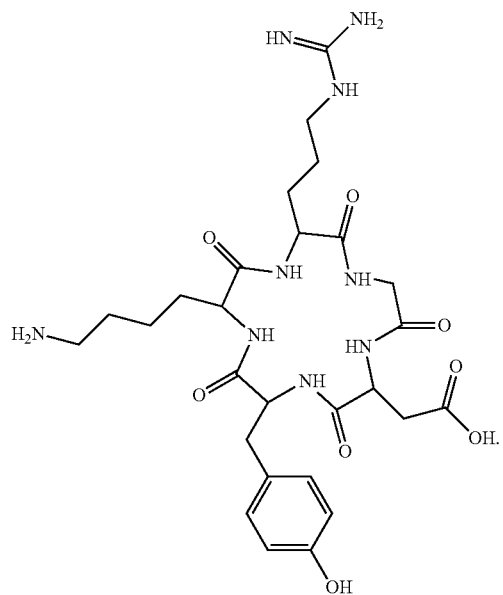

Formula I

In a fifth aspect, provided herein is a method of printing a silk fibroin hydrogel comprising providing a solution comprising a carrier and silk fibroin selected from the group consisting of unsubstituted silk fibroin, tyramine-substituted silk fibroin, and combinations thereof; separating the solution into (i) a first portion further comprising a peroxidase enzyme and (ii) a second portion further comprising a substrate for the peroxidase enzyme; and mixing the first portion and the second portion in a co-axial nozzle while printing the mixture onto a surface, whereby gelation of the hydrogel occurs during printing on the surface. In some embodiments, the peroxidase enzyme is selected from the group consisting of laccase, a microperoxidase, soy bean peroxidase, myeloperoxidase, lactoperoxidase, eosinophil peroxidase, thyroid peroxidase, and horseradish peroxidase. In some embodiments, the substrate is selected from the group consisting of hydrogen peroxide, barium peroxide, calcium peroxide, sodium peroxide, organic peroxides and combinations thereof. In some embodiments, the enzyme is horseradish peroxidase and the substrate is hydrogen peroxide. In some embodiments, the carrier is selected from the group consisting of water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, HEPES, Hank's balanced medium, Roswell Park Memorial Institute (RPMI) medium, fetal bovine serum, or combinations thereof. In some embodiments, the solution further comprises a cyclic RGD peptide. In some embodiments, the flow rate of the mixture through the co-axial nozzle is between about 0.1 ml/min and about 1.0 ml/min.

In a sixth aspect, provided herein is a method for forming a silk fibroin hydrogel microbead comprising mixing while passing through a needle (i) an aqueous solution comprising a carrier, a peroxidase enzyme, and silk fibroin selected from the group consisting of unsubstituted silk fibroin, tyramine-substituted silk fibroin, and combinations thereof and (ii) an oil phase solution comprising a substrate for the peroxidase enzyme, a surfactant, and an oil, whereby silk fibroin hydrogel microbeads are formed by gelation of the silk fibroin during mixing. In some embodiments, the peroxidase enzyme is selected from the group consisting of laccase, a microperoxidase, soy bean peroxidase, myeloperoxidase, lactoperoxidase, eosinophil peroxidase, thyroid peroxidase, and horseradish peroxidase. In some embodiments, the substrate is selected from the group consisting of hydrogen peroxide, barium peroxide, calcium peroxide, sodium peroxide, organic peroxides and combinations thereof. In some embodiments, the enzyme is horseradish peroxidase and the substrate is hydrogen peroxide. In some embodiments, the carrier is selected from the group consisting of water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, HEPES, Hank's balanced medium, Roswell Park Memorial Institute (RPMI) medium, fetal bovine serum, or combinations thereof. In some embodiments, the aqueous solution further comprises a cyclic RGD peptide. In some embodiments, the flow rate of the aqueous solution through the needle is between about 0.001 ml/min and 0.5 ml/min. In some embodiments, the flow rate of the oil phase solution through the needle is between about 1.5 ml/min and about 2.5 ml/min. In some embodiments, the oil is paraffin oil.

In a seventh aspect, provided herein is a silk fibroin hydrogel microbead made by the methods disclosed herein. In some embodiments, the diameter of the microbead is between about 5 µm and about 50 µm. In some embodiments, the microbead further comprising an active agent. In some embodiments, silk fibroin is tyramine-substituted silk fibroin.

In an eighth aspect, provided herein is a composition comprising tyramine-substituted silk fibroin, wherein a first phenol group of the tyramine-substituted silk fibroin is covalently crosslinked to a second phenol group in the composition. In some embodiments, the second phenol group is covalently bonded to one of the following: the tyramine-substituted silk fibroin, an unsubstituted silk fibroin, or a protein polymer. The protein polymer may be elastin, chitosan, collagen, gelatin, agarose, alginate, chitin, polyhydroxyalkanoates, pullan, starch, cellulose, hyaluronic acid, polydimethylsiloxane, poly(lactide-co-glycolide), resilin, poly(ethylene glycol).

In some embodiments, the provided composition retains at least 30% of an original mass of the composition upon exposure to a protease over a degradation duration of at least 4 days.

In some embodiments, the composition has a surface that has an area of cell spreading with a median value of at least 2000 µm$^2$ after 24 hours following positioning cells on the surface at a cell density of at least 1,000 cells/cm$^2$ in a growth medium.

In some embodiments, a surface of the composition has a fold change in metabolic activity of cells of at least 1.25 after at least 3 days following positioning cells on the surface a cell density of at least 1,000 cells/cm$^2$ in a growth medium.

In some embodiments, the composition has a fold change in metabolic activity of encapsulated cells of less than 2.5 after at least 3 days following encapsulating the cells in the composition comprising a growth medium, wherein the cells are present at an initial concentration of at least 1×10$^5$ cells/mL.

In a ninth aspect, provided herein is a method of contacting a solution comprising tyramine-substituted silk fibroin with an enzyme and a substrate for the enzyme, wherein a covalent crosslink between a first phenol group of the tyramine-substituted silk fibroin and a second phenol group in the composition is formed. The solution may undergo gelation from a non-gelated solution to a hydrogel upon mixing the tyramine-substituted silk fibroin, the enzyme, and the substrate. In some embodiments, the second phenol group is covalently bonded to one of the following: the tyramine-substituted silk fibroin, an unsubstituted silk fibroin, or a protein polymer. The protein polymer may be elastin, chitosan, collagen, gelatin, agarose, alginate, chitin, polyhydroxyalkanoates, pullan, starch, cellulose, hyaluronic acid, polydimethylsiloxane, poly(lactide-co-glycolide), resilin, poly(ethylene glycol). In some embodiments, In some embodiments, the tyramine-substituted silk fibroin, the substrate, and the enzyme are present at a concentration to provide a gelation time from 10 seconds to 10 minutes.

In some embodiments, wherein the tyramine-substituted silk fibroin, the substrate, and the enzyme are present at a concentration to provide a storage modulus from 100 Pa to 5 kPa.

In some embodiments, the substrate, and the enzyme are present at a concentration to retain at least 30% of an original mass of the composition upon exposure to a protease over a degradation duration of at least 4 days.

In some embodiments, the tyramine-substituted silk fibroin, the substrate, and the enzyme are present at a concentration to provide a surface of the composition that has a fold change in metabolic activity of cells of at least 1.25 after at least 3 days following positioning cells on the surface a cell density of at least 1,000 cells/cm$^2$ in a growth medium.

In some embodiments, the tyramine-substituted silk fibroin, the substrate, and the enzyme are present at a concentration to provide the composition with a fold change in metabolic activity of encapsulated cells of less than 2.5 after at least 3 days following encapsulating the cells in the composition with a growth medium, wherein the cells are present at an initial concentration of at least 1×10$^5$ cells/mL.

In some embodiments, the composition further includes at least one cyclic arginine-glycine-aspartic acid (RGD) peptide covalently linked to at least one phenol group in the composition.

In some embodiments, the tyramine-substituted silk fibroin, the substrate, the enzyme, and the cyclic RGD peptide are present at a concentration to provide a surface of the composition that has an area of cell spreading with a median value of at least 2000 µm$^2$ after 24 hours following positioning cells on the surface at a cell density of at least 1,000 cells/cm$^2$ in a growth medium

BRIEF DESCRIPTION OF DRAWINGS

The patent or patent application file contains at least one drawing in color. Copies of this patent or patent application publication with color drawings will be provided by the Office upon request and payment of the necessary fee.

(FIG. 1A) Carbodiimide coupling of tyramine (TA) groups to carboxylic acid residues on silk fibroin (SF) chains. (FIG. 1B) Encapsulation of human mesenchymal stem cells (hMSCs) within enzymatically crosslinked SF/SF-TA hydrogels with in situ conjugated cyclo(RGDyK).

(FIG. 3A) Photograph showing 5% SF/SF-TA solutions gelled in the bottom of Eppendorf tubes. Influence of SF-TA weight ratio on (i) crosslinking kinetics and (ii) maximum fluorescence intensities of (FIG. 1B) 5% hydrogels crosslinked in 40 mM HEPES buffer and (FIG. 1C) 3% hydrogels crosslinked in 0.5×DMEM buffer (n=5, *p<0.05, p<0.01 and *p<0.001, asterisks above the bars represent significance compared to SF only gels).

(FIG. 5A) Representative time sweeps (i), shear storage moduli at t=4000 s (ii) and gel (G"/G'<0.05) points (iii) of 5% hydrogels prepared in 40 mM HEPES buffer. (FIG. 5B) Representative time sweeps (i) and shear storage moduli at t=4000 s (ii) of 3% hydrogels prepared in 0.5×DMEM (n=3, *p<0.05, p<0.01 and *p<0.001).

FIGS. 7A-7D show influence of cyclo(RGDyK) on rheological properties of SF/30% SF-TA hydrogels. (FIG. 7A) Schematic representation of covalent crosslinking of silk chains with and without cyclo(RGDyK) cyclic peptide. (FIG. 7B) Representative time sweep curves, (FIG. 7C) resulting shear storage moduli at t=4000 s, and (FIG. 7D) gel (G"/G'<0.05) points of 3% SF/SF-TA solutions mixed with various concentrations of cyclo(RGDyK) and crosslinked using 0.01% or 0.005% $H_2O_2$ in 0.5×DMEM (n=3, *p<0.05, p<0.01 and *p<0.001).

FIGS. 8A-8D show 3D printing of enzymatically crosslinked SF-TA hydrogels. (FIG. 8A) Schematic representation of 3D printing based on gelation during extrusion right after the mixing of two solutions supplemented with the enzyme HRP or H2O2. (FIG. 8B) The setup used for manual printing of SF-TA hydrogels using a 2-inlet needle and a syringe pump. (FIG. 8C) Photograph showing the 2-inlet needle system attached to a commercial 3D printer Cellink. (FIG. 8D) SF-TA hydrogel patterns manually printed using the setup shown in (FIG. 8B).

(FIG. 9A) The experimental setup that consists of 2 syringe pumps and a coaxial needle used for microgel fabrication. (FIG. 9B) Brightfield micrograph of the SF-TA microgels fabricated by using an oil flow rate of 2 mL/min and an aqueous flow rate of 0.05 mL/min.

(FIG. 11A) Photograph showing the morphologies of 5% SF/SF-TA hydrogel discs crosslinked in 40 mM HEPES buffer and incubated in DPBS at 37° C. for 1, 14 and 28 days. (FIG. 111B) In vitro degradation of hydrogels over 8 days of incubation in PBS with 0.001 U/mL protease XIV (n=4, *p<0.05, p<0.01 and *p<0.001).

(FIG. 12A) Fluorescence images of hMSCs 24 h after seeding on hydrogel surfaces (green: calcein, scale bars: 100 μm). (FIG. 12B) Box-whisker distribution graphs showing the effects of cyclo(RGDyK) content on spread area at day 1 (spread areas of individual cells were quantified on fluorescent micrographs using ImageJ software, n>200). (FIG. 12C) Fold changes in metabolic activity of hMSCs on 5% silk hydrogels supplemented with cyclo(RGDyK) over 4 weeks of culture compared to day 1 (n=4, *p<0.05, p<0.01 and *p<0.001, asterisks above the bars represent significance compared to no cycloRGD control). (FIG. 12D) Fluorescent micrographs of hMSCs at days 1, 14 and 28 on 5% composite hydrogels supplemented with various concentrations of cyclo(RGDyK). Hydrogels were prepared in 40 mM HEPES buffer. (Green: calcein (live), red: EthD-1 (dead), scale bars: 100 μm).

(FIG. 13A) (i) Day 1 fluorescent micrographs of hMSCs encapsulated in 5% silk hydrogels (prepared in 40 mM HEPES) with different SF-TA weight ratios (green: live (calcein), red: dead (EthD-1), scale bars: 100 μm). (ii) % dye reduction by the cells encapsulated in 5% SF/SF-TA composite hydrogels. (FIG. 13B) (i) Fluorescent micrographs (scale bars: 100 μm) and fold changes in metabolic activity of hMSCs encapsulated in 3% SF/SF-TA composite hydrogels supplemented with cyclo(RGDyK) at various concentrations and crosslinked in 0.5×DMEM buffer using 0.01% or 0.005% $H_2O_2$ (n=4, *p<0.05, p<0.01 and *p<0.001).

FIG. 14A shows insertion of 3% w/v SF-TA hydrogel discs into the subcutaneous pockets created on the back of 12-week-old female FVB/NJ mice. FIG. 14B shows day 3 photographs of subcutaneously implanted SF-TA hydrogel discs (i) before and (ii) after removal from mice.

FIG. 16A shows nonspecific deposition of SF-TA hydrogel layers by priming of cells surface with G-TA followed by in situ crosslinking of SF-TA on the priming gelatin layer. FIG. 16B shows Cell-specific in situ crosslinking of SF-TA hydrogel layers on the cells by localized gelation through antibody-mediated cell surface-immobilized HRP.

FIG. 17A at panel (i) shows confocal and at panel (ii) shows fluorescence micrographs of L929 fibroblasts. FIG. 17B shows (i) shows confocal and at panel (ii) shows fluorescence micrographs of hMSCs after nanoencapsulation within fluorescently labeled silk hydrogel layers and after live/dead staining, respectively. Live/dead micrographs: green: calcein (live), red: EthD-1 (dead). Scale bars: 50 μm.

INCORPORATION BY REFERENCE

Figures 1A, 1B:
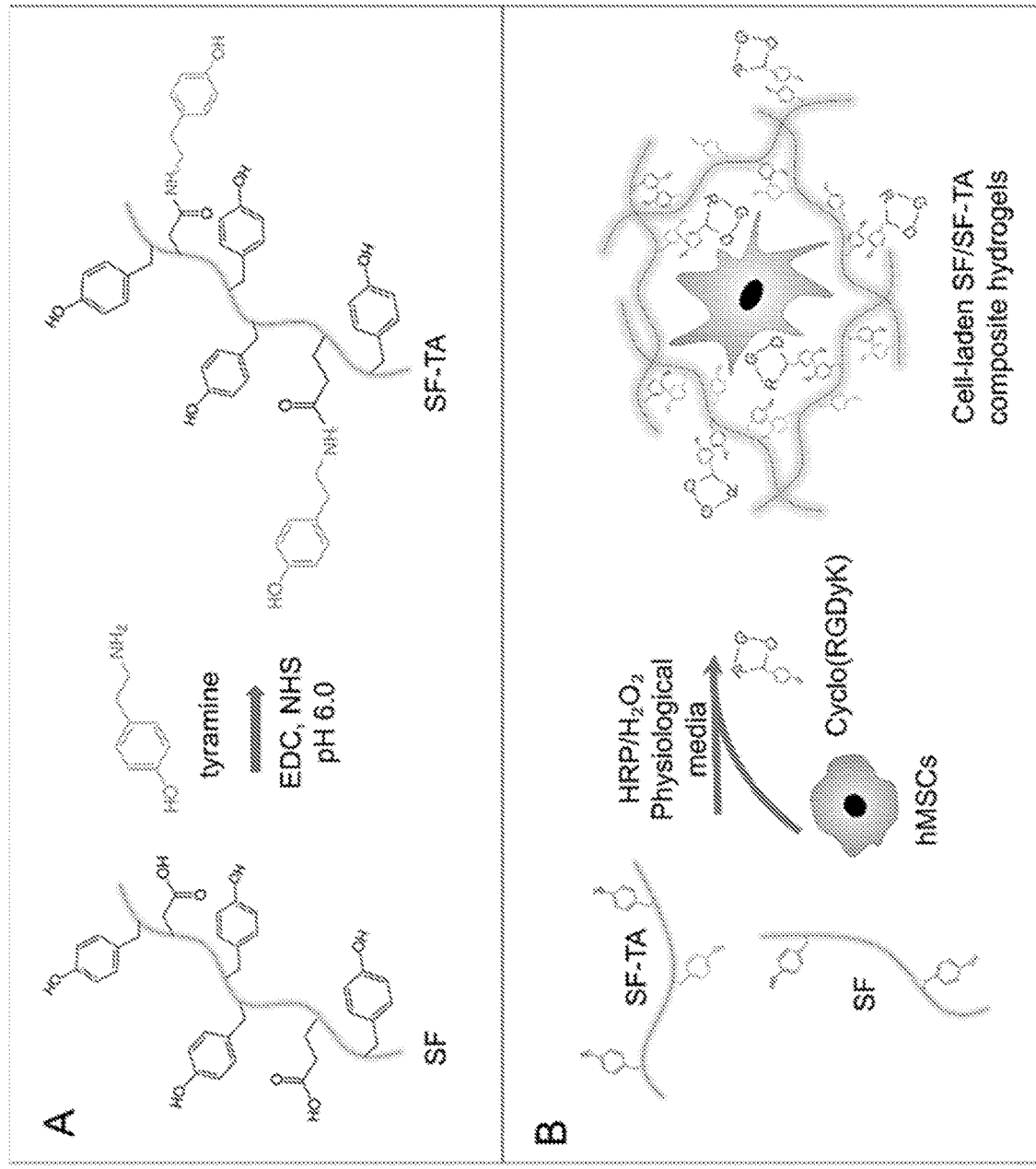
FIGS. 1A-1B show a schematic representation of the SF/SF-TA composite hydrogels for cell encapsulation.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death (e.g., less than 10% or 5%), and/or their administration in vivo does not induce significant inflammation or other such adverse effects.

As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

As used herein, the term "amino acid," in its broadest sense, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

As used herein, the term "biodegradable" refers to materials that, when introduced to cells (either internally or by being placed in proximity thereto), are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

As used herein, "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

The term "in vitro" as used herein refers to events that occur in an artificial environment, e.g., in a test tube or reaction vessel, in cell culture, etc., rather than within a multi-cellular organism.

As used herein, "in situ" refers to events that occur in the same place and/or at the same time that another phenomenon, chemical reaction, treatment, or event is occurring.

As used herein, "in vivo" refers to events that occur within a multi-cellular organism, such as a human and a non-human animal. In the context of cell-based systems, the term may be used to refer to events that occur within a living cell (as opposed to, for example, in vitro systems).

As used herein, "physiological conditions" has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

The term "polypeptide", as used herein, generally has its art-recognized meaning of a polymer of at least two amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Proteins may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. In some embodiments, proteins are antibodies, antibody fragments, biologically active portions thereof, and/or characteristic portions thereof.

As used herein, "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.).

As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

The present disclosure describes chemical modification strategies for silk fibroin (SF) involving the enrichment in phenol residues through carbodiimide coupling of tyramine groups on silk chains and in situ covalent conjugation of cyclic RGD peptides during enzymatic crosslinking to improve gelation kinetics in physiological buffers and to enhance bioactivity of the resulting hydrogels, respectively. The compositions and methods described herein provide a simple and robust strategy for rapid gelation of enzymatically crosslinked silk hydrogels with tunable bioactivity for potential uses as injectable tissue fillers, bioinks for 3D bioprinting and in droplet-based microfabrication of hydrogel spheres for encapsulation and delivery of cells and therapeutics. The methods are also applicable for different molecular weights of silk or different silks from other organisms including wild silkworms or spiders, and it provides an alternative to ionically crosslinked alginate-based hydrogels, which have limited structural and mechanical stability at physiological conditions.

As described herein, in some embodiments, provided compositions (e.g., hydrogels) are hydrophilic polymeric networks that can be utilized as scaffolds for biomedical applications (e.g., regenerative medicine, drug delivery, tissue fillers, and tissue engineering), bioinks for 3D printing, and droplet-based microfabrication of hydrogel spheres for encapsulation and delivery of cells and therapeutics. Due to their hydrophilic nature, provided compositions (e.g., hydrogels) are permeable to oxygen and nutrients and possess mechanics similar to that of native extracellular matrix, creating a receptive environment for cell proliferation.

Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, New Jersey (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta*; *Antheraea pernyi*; *Antheraea yamamai*; *Galleria mellonella*; *Bombyx mori*; *Bombyx mandarina*; *Galleria mellonella*; *Nephila clavipes*; *Nephila senegalensis*; *Gasteracantha mammosa*; *Argiope aurantia*; *Araneus diadematus*; *Latrodectus geometricus*; *Araneus bicentenarius*; *Tetragnatha versicolor*; *Araneus ventricosus*; *Dolomedes tenebrosus*; *Euagrus chisoseus*; *Plectreurys tristis*; *Argiope trifasciata*; and *Nephila madagascariensis*.

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. In accordance with various embodiments, silk fibroin may be modified prior to use in provided methods and compositions. For example, in some embodiments, silk fibroin may be modified to include more tyrosine groups than native silk fibroin (e.g., silk fibroin from a silkworm or a spider), or to include fewer tyrosine groups than native silk fibroin. By way of specific example, in some embodiments, silk fibroin may be modified to include at least one non-native tyrosine. In some embodiments, silk fibroin may be modified to remove or alter at least one tyrosine group from native silk fibroin such that it is no longer able to crosslink with tyramine-substituted silk fibroin. In some embodiments, addition of tyrosine groups to silk fibroin may occur via carbodiimide chemistry.

In general, silk fibroin for use in accordance with the present invention may be produced by any such organism, or may be prepared through an artificial process, for example, involving genetic engineering of cells or organisms to produce a silk protein and/or chemical synthesis. In some embodiments of the present invention, silk fibroin is produced by the silkworm, *Bombyx mori*. Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of nonstructural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the *Bombyx mori* fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained from the cocoon of *Bombyx mori*. In some embodiments, spider silk fibroins are obtained, for example, from *Nephila clavipes*. In some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

In some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk materials explicitly exemplified herein were typically prepared from material spun by silkworm, *Bombyx mori*. Typically, cocoons are boiled in an aqueous solution of 0.02 M $Na_2CO_3$, then rinsed thoroughly with water to extract the glue-like sericin proteins (this is also referred to as "degumming" silk). Extracted silk is then dissolved in a solvent, for example, LiBr (such as 9.3 M) solution at room temperature. A resulting silk fibroin solution can then be further processed for a variety of applications as described elsewhere herein.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

As used herein, "tyramine-substituted silk fibroin" or "SF-TA" refers to silk fibroin fragments conjugated with tyramine on carboxylic acid groups of glutamic acid and aspartic acid residues via carbodiimide coupling. See FIG. 1A. Conjugation of tyramine on to the carboxylic acid groups of glutamic acid (Glu or E) and aspartic acid (Asp or D), in particular the E and D residues in the amorphous regions of the silk fibroin, will increase the total phenol content of the silk fibroin.

In some embodiments, the total phenol content of the tyramine-substituted silk fibroin is at least 5.5 mol %, at least 5.6 mol %, at least 5.7 mol %, at least 5.8 mol %, at least 5.9 mol %, at least 6.0 mol %, at least 6.1 mol %, at least 6.2 mol %, at least 6.3 mol %, at least 6.4 mol %, at least 6.5 mol %, at least 6.6 mol %, at least 6.7 mol %, at least 6.8 mol %, at least 6.9 mol % or at least 7.0 mol %. In some embodiments, tyramine conjugation of the silk fibroin increases total phenol content by at least 10%, at least 12%, at least 15%, at least 18%, at least 20%, at least 22%, at least 25%, or at least 30% relative to the phenol content in the unmodified silk fibroin. Any known technique for quantifying the amount of tyrosine and/or tyramine groups on silk fibroin may be used. For example, in some embodiments, quantification of tyrosine and/or tyramine groups may be performed using one or more of spectrophotometric analysis (e.g., via UV absorbance), liquid chromatography-mass spectrometry (LC-MS), and high performance liquid chromatography (UPLC).

Tyramine-substituted silk fibroin is formed by contacting a silk fibroin solution with with tyramine hydrochloride in the presence of 1-ethyl-3-(-3-dimethylaminopropyl) carbodiimide hydrochloride (EDC) and N-hydroxysuccinimide (NHS). In some embodiments, the silk fibroin solution is an aqueous silk fibroin solution. In some embodiments, the aqueous silk fibroin solution additional comprises a buffer and the solution is maintained at a pH of about 6.0. In some embodiments, the tyramine hydrochloride is provided in an amount between about 100 mg per 1 g silk fibroin protein and about 800 mg per 1 g silk fibroin protein. In some embodiments, the tyramine hydrochloride is provided in an amount of about 500 mg per 1 g silk fibroin protein. In some embodiments, the ECD is provided in an amount between 25 mg per 1 g silk fibroin protein and 250 mg per 1 g silk fibroin protein. In some embodiments, the NHS is provided in an amount between 5 mg per 1 g silk fibroin protein and 100 mg per 1 g silk fibroin protein. In some embodiments, the silk fibroin solution is contacted with tyramine hydrochloride, ECD, and NHS with stirring under ambient conditions for between about 5 hours and about 24 hours.

As used herein, "unsubstituted silk fibroin" refers to silk fibroin or silk fibroin fragments that have not been conjugated with tyramine. Unsubstituted silk fibroin may still be modified in other ways, substituted with other moieties, or subject to other chemical processes necessary for gelation and preparation of compositions provided herein. In some embodiments, unsubstituted silk fibroin is the reference by which an increase or decrease in phenol content is measured.

In some embodiments, silk fibroin fragments and tyramine-modified silk fibroin may be of any application-appropriate size. For example, in some embodiments, silk fibroin fragments and tyramine-modified silk fibroin may have a molecular weight of 200 kDa or less (e.g., less than 125 kDa, 100 kDa, 75 kDa, 50 kDa). Without wishing to be held to a particular theory, it is contemplated that the size of silk fibroin fragments and tyramine-modified silk fibroin may impact gelation time and rate of crosslinking. By way of specific example, in some embodiments, use of silk fragments and tyramine-modified silk fibroin of a relatively low molecular weight (e.g., less than 200 kDa) may result in relatively more rapid crosslinking due, at least in part, to the greater mobility of the available chains for reacting in a crosslinking step.

In some embodiments, hydrogels of the present invention produced from silk fibroin fragments can be formed by degumming silk cocoons in an aqueous solution at temperatures of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, silk fibroin fragments and tyramine-modified silk fibroin may be solubilized in a carrier prior to gelation. In some embodiments, a carrier can be a solvent or dispersing medium. In some embodiments, a solvent and/or dispersing medium, for example, is water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, HEPES, Hank's balanced medium, Roswell Park Memorial Institute (RPMI) medium, fetal bovine serum, or suitable combinations and/or mixtures thereof.

In some embodiments, the properties of provided compositions may be modulated by controlling a concentration of silk fibroin. In some embodiments, a weight percentage of silk fibroin (including silk fibroin, unsubstituted silk fibroin, tyramine-substituted silk fibroin, or combinations thereof) can be present in a solution at any concentration suited to a particular application. In some embodiments, an aqueous silk fibroin solution (or a provided composition, for example, a provided hydrogel) can have silk fibroin (including silk fibroin, unsubstituted silk fibroin, tyramine-substituted silk fibroin, or combinations thereof) at a concentration of about 0.1 wt % to about 95 wt %, 0.1 wt % to about 75 wt %, or 0.1 wt % to about 50 wt %. In some embodiments, an aqueous silk fibroin solution (or a provided composition, for example, a provided hydrogel) can have silk fibroin (including silk fibroin, unsubstituted silk fibroin, tyramine-substituted silk fibroin, or combinations thereof) at a concentration of about 0.1 wt % to about 10 wt %, about 0.1 wt % to about 5 wt %, about 0.1 wt % to about 2 wt %, or about 0.1 wt % to about 1 wt %. In some embodiments, a silk fibroin solution (or a provided composition, for example, a provided hydrogel) have silk fibroin (including silk fibroin, unsubstituted silk fibroin, tyramine-substituted silk fibroin, or combinations thereof) at a concentration of about 10 wt % to about 50 wt %, about 20 wt % to about 50 wt %, about 25 wt % to about 50 wt %, or about 30 wt % to about 50 wt %. In some embodiments, a weight percent of silk (including silk fibroin, unsubstituted silk fibroin, tyramine-substituted silk fibroin, or combinations thereof) in solution (or a provided composition, for example, a provided hydrogel) is about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, is about less than 25 wt %, or is about less than 30 wt %. In some embodiments, a weight percent of silk (including silk fibroin, unsubstituted silk fibroin, tyramine-substituted silk fibroin, or combinations thereof) in solution (or a provided composition, for example, a provided hydrogel) is at least 1 wt %, is at least 1.5 wt %, is at least 2 wt %, is at least 2.5 wt %, is at least 3 wt %, is at least 3.5 wt %, is at least 4 wt %, is at least 4.5 wt %, is at least 5 wt %, is at least 5.5 wt %, is at least 6 wt %, is at least 6.5 wt %, is at least 7 wt %, is at least 7.5 wt %, is at least 8 wt %, is at least 8.5 wt %, is at least 9 wt %, is at least 9.5 wt %, is at least 10 wt %, is at least 11 wt %, is at least 12 wt %, is at least 13 wt %, is at least 14 wt %, is at least 15 wt %, is at least 16 wt %, is at least 17 wt %, is at least 18 wt %, is at least 19 wt %, is at least 20 wt %, is at least 25 wt %, or is at least 30 wt %.

In some embodiments, the properties of provided compositions may be modulated by controlling a concentration of tyramine-substituted silk fibroin. In some embodiments, a weight percentage of tyramine-substituted silk fibroin can be present in a solution at any concentration suited to a particular application. In some embodiments, an aqueous tyramine-substituted silk fibroin solution (or a provided composition, for example, a provided hydrogel) can have silk fibroin at a concentration of about 0.1 wt % to about 95 wt %, 0.1 wt % to about 75 wt %, or 0.1 wt % to about 50 wt %. In some embodiments, an aqueous tyramine-substituted silk fibroin solution (or a provided composition, for example, a provided hydrogel) can have silk fibroin at a concentration of about 0.1 wt % to about 10 wt %, about 0.1 wt % to about 5 wt %, about 0.1 wt % to about 2 wt %, or about 0.1 wt % to about 1 wt %. In some embodiments, a tyramine-substituted silk fibroin solution (or a provided composition, for example, a provided hydrogel) have silk fibroin at a concentration of about 10 wt % to about 50 wt %, about 20 wt % to about 50 wt %, about 25 wt % to about 50 wt %, or about 30 wt % to about 50 wt %. In some embodiments, a weight percent of tyramine-substituted silk in solution (or a provided composition, for example, a provided hydrogel) is about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, is about less than 25 wt %, or is about less than 30 wt %.

In some embodiments, the properties of provided compositions may be modulated by controlling ratio of tyramine-substituted silk fibroin and silk fibroin. In some embodiments, the hydrogel compositions provided herein include only tyramine-substituted silk fibroin. In some embodiments, the ratio of silk fibroin to tyramine-substituted silk fibroin is in the range of 15:1 to 1:15, the range of 12:1 to 1:12, the range of 10:1 to 1:10, the range of 10:1 to 1:1, the range of 10:1 to 5:1, the range of 1:1 to 1:10, or the range of 1:5 to 1:10. In some embodiments, the tyramine-substituted silk fibroin is present in the hydrogel composition in an amount of about 5%, about 10%, about 15%, about 20%, about 25%, about 30%, about 35%, about 40%, about 45%, about 50%, about 60%, about 70%, about 80%, about 90% or about 100% of the total polymer concentration of the hydrogel composition with the remainder of the polymer concentration being silk fibroin. In some embodiments, the total polymer concentration in the hydrogel compositions is about 2%, about 3%, about 4%, about 5%, about 6%, or about 7%. In some embodiments, the total polymer concentration in the hydrogen composition is between about 1% and about 7%, between about 2% and about 6%, or between about 3% and about 5%.

In some embodiments, a provided composition may form a porous matrix or scaffold (e.g., a foam, or lyophilized composition). For example, the porous scaffold can have a porosity of at least about 10%, at least about 20%, at least about 30%, at least about 40%, at least about 50%), at least about 60%, at least about 70%, at least about 80%, at least about 90%, or higher.

In certain embodiments, particularly where provided compositions are or comprise hydrogels, silk fibroin from *Bombyx mori* cocoons can provide protein that can be utilized as naturally derived hydrogels with good biocompatibility, mechanical strength and ease of chemical modifications. Silk-based hydrogels can be prepared via many methods including sonication, pH, vortexing, electric fields, polyols, surfactants, and enzymatic reactions. For example, as previously reported, the covalently crosslinking of the phenolic groups of tyrosine residues in silk fibroin using horseradish peroxidase (HRP) and hydrogen peroxide ($H_2O_2$), resulted in a cytocompatible, mechanically tunable, elastomeric protein biomaterial. See, for example, U.S. Patent Publication No. 2016/0256604 and U.S. Patent Publication No. 2019/0282731, each of which are incorporated herein in their entirety. These enzymatically formed hydrogels can avoid the brittle nature of physically (beta sheet formed) crosslinked silk hydrogels. Due to their resilience, lack of harsh crosslinking conditions, and tunable mechanics, similar to that of native tissues, these enzymatically crosslinked silk hydrogels provide a useful system for efficient cell encapsulation and tissue engineering.

However, these pure silk hydrogels lack bioactivity and depending on reaction conditions can undergo changes in mechanics over time due to slow crystallization. The hydrogel compositions described herein include tyramine-substituted silk fibroin and/or cyclic RGD polymers to increase bioactivity, improve gelation kinetics, and improve mechanical properties of the hydrogels.

As used herein, "cyclic RGD polymer" refers to an arginine-glycine-aspartic acid polymer containing a circular sequences of bonds connecting the amino and carboxyl ends of the residues in the peptide. In some embodiments, the cyclic RGD polymer includes a phenolic group. In some embodiments, the cyclic RGD includes tyrosine. In some embodiments, the cyclic RGD polymer is cyclo(RGDyK), a cyclic peptide of arginine-glycine-aspartic acid-tyrosine-lysine having the structure of formula I:

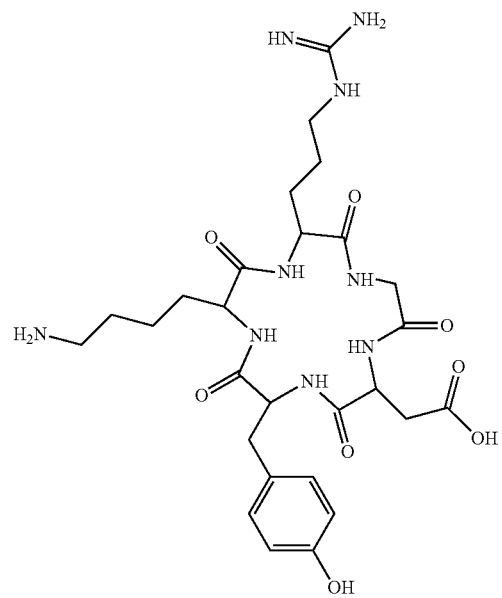

Formula I

Prior to the present invention, there were few reports that address modulating the enzymatically crosslinked silk hydrogels through crosslinking of substituted silk fibroin using this enzymatic reaction. Recently, the enzymatic crosslinking of silk and cardiac extracellular matrix (cECM) showed enhanced growth in vitro and infiltration in vivo but did not show a large effect in stiffening over time (see Stoppel, W. et al., 2016, "Elastic, silk-cardiac extracellular matrix hydrogels exhibit time-dependent stiffening that modulates cardiac cell response." Journal of Biomedical Materials Research: Part A., 104(12): 3058-3072). To overcome these factors, we sought to incorporate hydrophilic, bioactive tyramine-substituted silk fibroin to potentially inhibit crystallization and stiffening and provide cell instructive cues.

As is known in the art, the process of joining two or more peptide/protein molecules through intermolecular covalent bonds is referred to crosslinking. A variety of crosslinking modes are contemplated as useful in accordance with various embodiments.

Notably, in some embodiments, the methods of crosslinking described herein avoid harsh crosslinking conditions including, but not limited to—use of harsh or toxic chemicals and/or use of physical crosslinking (e.g., β-sheet formation). In some embodiments, a crosslinking step may occur in an aqueous environment. In some embodiments, a crosslinking step may occur in the absence of organic solvents or other toxic materials. In some embodiments, all covalent coupling and hydrogel crosslinking reactions are carried out in aqueous solutions at ambient conditions. In some embodiments, all covalent coupling and hydrogel crosslinking reactions are carried in the absence of organic solvent. As used herein, "organic solvent-free" refers to reaction conditions or solutions that are free of any organic solvent.

Covalently crosslinking, for example, silk and hyaluronic acid hydrogels using a variety of chemical crosslinking methods has been proposed to treat skin and soft tissue conditions. Common chemical crosslinkers, such as butanediol diglycidyl ether (BDDE), operate under harsh conditions, not only leading to HA degradation but also prohibiting cell encapsulation. A milder method of crosslinking that was described involved the use of 1-ethyl-3-[3-dimethylaminopropyl]carbodiimide hydrochloride (EDC) chemistry with hexamethylene diamine (HDMA). Although this method can be carried out under physiological conditions, the crosslinking agents can be cytotoxic. Therefore hydrogels created using these methods are often washed prior to injection and can possibly lead to cell and tissue death when crosslinked in situ. Accordingly, in some embodiments, harsh or toxic reagent, such as BDDE, EDC, and/or HMDA are not used.

Accordingly, as described herein are compositions made by copolymerizing (1) silk fibroin and tyramine-substituted silk fibroin, (2) tyramine-substituted silk fibroin alone, (3) silk fibroin and tyramine-substituted silk fibroin in the presence of a cyclic RGD peptide, or (4) tyramine-substituted silk fibroin in the presence of a cyclic RGD peptide using an enzymatic crosslinking step to generate biocompatible, elastomeric hydrogels that have improved bioactivity, improved gelation kinetics, and improved mechanical properties.

Without wishing to be bound by any particular theory or reaction chemistry and stoichiometry, crosslinking of silk fibroin protein in the compositions described herein may include, without limitation, (i) crosslinking of at least one tyrosine group of unsubstituted silk fibroin to at least one tyrosine group of unsubstituted silk fibroin; (ii) crosslinking of at least one tyrosine group on unsubstituted silk fibroin to at least one phenol-group of tyramine-substituted silk fibroin, including di-tyrosine and tyrosine-tyramine linkages; (iii) crosslinking of at least one tyrosine group of unsubstituted silk fibroin to a cyclic RGD peptide; (iv) crosslinking of at least one phenol-group of tyramine-substituted silk fibroin to at least one phenol-group of tyramine-substituted silk fibroin, including di-tyrosine, di-tyramine, and tyrosine-tyramine linkages; (v) crosslinking of at least one phenol-group of tyramine-substituted silk fibroin to a cyclic RGD peptide; (vi) crosslinking of at least one phenol-group of a non-silk phenol-containing polymer to at least one phenol-group of a non-silk phenol-containing polymer, including di-tyrosine, di-tyramine, and tyrosine-tyramine linkages; (vii) crosslinking of at least one phenol-group of a non-silk phenol-containing polymer to at least one phenol-group of a tyramine-substituted silk fibroin including di-tyrosine, di-tyramine, and tyrosine-tyramine linkages, (viii) crosslinking of at least one phenol-group of a non-silk phenol-containing polymer to a tyrosine group of unsubstituted silk fibroin, including di-tyrosine and tyrosine-tyramine linkages; (ix) crosslinking of at least one phenol-group of a non-silk phenol-containing polymer to a cyclic RGD peptide; and (x) combinations thereof.

By modulating the polymer, HRP and $H_2O_2$ concentrations, the mechanical properties, crystallization, and biological responses over extended times could be controlled. Ultimately, this hydrogel will provide a versatile tunable platform for a wide range of biomedical applications (including cell encapsulation, tissue regeneration, and tissue augmentation), bioinks for 3D printing, and droplet-based microfabrication of hydrogel spheres. One of skill in the art will appreciate that this technology is not limited to the crosslinking of silk and tyramine-substituted silk fibroin but can also be used to with any polymer/peptide/protein containing phenolic groups to incorporate specific biological or mechanical properties.

In some embodiments, silk fibroin and a tyramine-substituted silk fibroin are crosslinked directly to one another (e.g., there is no spacer between the two, for example, no epoxide or multiamine spacer). In some embodiments, crosslinking in provided methods and compositions is or comprises multi-phenol crosslinks. In some embodiments, multi-phenol crosslinks are selected from the group consisting of di-tyrosine crosslinks, di-tyramine crosslinks, and tyrosine-tyramine crosslinks. In some embodiments, crosslinking does not include physical crosslinking (e.g., via β-sheet formation). In some embodiments wherein the crosslinking does not include physical crosslinking, provided compositions or methods may include β-sheet formation during a later time or step subsequent to a crosslinking step. In some embodiments, crosslinking does not include chemical crosslinking (e.g., using harsh or toxic chemicals, via addition reaction(s), exposure to high energy radiation such as gamma rays or electron beams). In some embodiments, crosslinking may comprise one or more of a condensation reaction(s), carbodiimide crosslinking, and glutaraldehyde crosslinking.

In some aspects, provided methods may comprise contacting a silk solution, a tyramine-substituted silk solution, or combinations thereof with an enzyme, and inducing gelation of the silk solution comprising the enzyme in the presence of a substrate for the enzyme. In some embodiments, the mixture can be mixed gently to induce gelation. In some embodiments, the method employs a horseradish peroxidase enzyme (HRP) and hydrogen peroxide ($H_2O_2$) to enzymatically crosslink silk fibroins. Without wishing to be bound by theory, the horseradish peroxidase enzyme and hydrogen peroxide (e.g., an oxidizing agent) can be used to enzymatically crosslink the tyrosine side chains that are found in the native silk fibroin. The gel initiation and gelation rate and/or kinetic properties of the process can be tunable or controlled, for example, depending on concentrations of silk, enzyme (e.g., HRP), and/or substrate for the enzyme (e.g., $H_2O_2$).

In some embodiments, the silk fibroin and tyramine-substituted silk fibroin may each be provided in a separate solution prior to the associating step. In some embodiments, the tyramine-substituted silk fibroin may be enzymatically crosslinked to a separate phenol-containing polymer and the tyramine-substituted silk fibroin and the phenol-containing polymer may each be provided in a separate solution prior to the associating step. Without wishing to be held to a particular theory, in some embodiments, attempting to solubilize silk fibroin with at least one phenol-containing polymer may result in aggregation and/or precipitation of the silk and/or inability to fully solubilize the phenol-containing polymer.

In some embodiments, the compositions provided herein may further include a non-silk phenol containing polymer. Any application-appropriate phenol-containing polymer may be used. The specific phenol-containing polymer(s) used in a particular embodiment may depend on one or more of: the specific application of a provided composition, the physical or mechanical properties desired in the resultant composition, or the desired time to gelation for a particular embodiment (e.g., if encapsulation of one or more active agents is desired, it may be advantageous to have rapid gelation occur, such within one minute or less from the initiation of a crosslinking step).

In some embodiments, a phenol-containing polymer is or comprises a peptide or protein. In some embodiments, a phenol-containing polymer is a hydrophilic and/or bioactive polymer. In some embodiments, a phenol-containing polymer is or comprises a tyramine-containing and/or tyrosine-containing peptide or protein. In some embodiments, a tyramine-containing and/or tyrosine-containing peptide or protein is a peptide or protein that has been modified to incorporate one or more tyramine and/or tyrosine groups such that they are available to react as described herein. In some embodiments, a tyramine-containing and/or tyrosine-containing polymer is or comprises hyaluronic acid and/or polyethylene glycol.

Due to its biological and structural importance, as well as its ease of modification, HA can be an attractive polymer in general for biomedical applications and has been explored in drug delivery, synovial fluid supplementation, ocular and anti-adhesive surgery aids, wound healing, and soft tissue repair and augmentation. Since the turnover of HA is rapid (about ⅓ of the total HA body content is degraded and reformed daily), covalent crosslinking is necessary to increase mechanical stability for tissue engineering purposes. Covalent crosslinking can occur either directly through chemical approaches or by modifying the hydroxyl or carboxyl groups of HA with functional moieties, which can then be crosslinked. Tyramine-substituted HA (TS-HA) has been previously synthesized to provide a biocompatible hydrogel that can be enzymatically crosslinked, avoiding the harsh environment often required for chemical crosslinking methods. By utilizing HRP and $H_2O_2$, the tyramine functionalized carboxyl groups are covalently linked allowing for hydrogel formation under physiological conditions. These hydrogels have been explored in a wide range of applications in tissue engineering and drug delivery.

The combination of silk and hyaluronic acid has been previously explored in the form of hydrogels, films, microparticles, and sponges for cartilage, neuronal, and cardiac tissue engineering. One method of combining these two polymers in a bulk hydrogel is entrapping hyaluronic acid in a crystalline silk network through the application of ultrasonication. This physically crosslinked hydrogel facilitated human mesenchymal (hMSC) attachment and growth while providing mechanical integrity. A similar method was used to develop silk fibroin/HA hydrogels, which provided adequate mechanics and biological cues to maintain nucleus pulposus-like chondrogenic cell growth for tissue regeneration. However, the reliance on physically crosslinked, β-sheet, networks, results in brittle behavior, limiting applications and making them difficult to handle.

In some embodiments, a tyramine-containing and/or tyrosine-containing polymer comprises a modified form (e.g., wherein one or more phenol or tyramine group(s) added) of one or more of: dopamine, L-DOPA, serotonin, adrenaline, noradrenaline, salicylic acid, alginate, dextran, collagen, gelatin, chitosan, carboxymethylcellulose, heparin, poly(vinyl alcohol), sugars (e.g., lactose, cellulose, mannose, galactose, glucose, maltose, etc) or dimers or trimers thereof.

It is specifically contemplated that any of a variety of amounts of phenol-containing polymer may be used in accordance with various embodiments. By way of specific non-limiting example, in some embodiments, provided compositions may include between 0.01 wt % and 75 wt % phenol-containing polymer. In some embodiments, provided compositions may include at least 0.01 wt % phenol-containing polymer (e.g., at least 0.05, 0.1, 0.5 1, 2, 3, 4, 5, 10, 15, 20, 25, 30, 35, 40 45, 50, 55, 60, 65 wt %). In some embodiments, provided compositions may include at most 75 wt % phenol-containing polymer (e.g., at most 70, 65, 60, 55, 50, 45, 40, 35, 30, 25, 20, 15, 10, 5 wt %).

Previous methods often resulted in crosslinking agents remaining in association with a crosslinked composition, requiring some sort of purification or removal step. In some embodiments, provided methods avoid this need. Accordingly, in some embodiments, provided methods do not include a purification step. In some embodiments, provided methods do not require a removal step to reduce or eliminate the presence of one or more contaminants (e.g., cross linkers, toxic or harsh chemicals, etc) before use (e.g., injection or other administration). In some embodiments, provided methods do not require or utilize organic solvents (particularly not volatile organic solvents).

In accordance with various embodiments, provided methods include the use of one or more enzymes, along with an appropriate exogenous substrate, if needed, capable of forming covalent bonds between silk fibroin and tyramine-substituted silk fibroin. In accordance with various embodiments where a provided composition is or comprises a hydrogel, provided methods may include one or more steps to induce gelation including gentle mixing, heating, etc. as appropriate for a particular enzyme (and potentially substrate). In some embodiments, enzymatic crosslinking (e.g., as is used in many embodiments of gelation reactions herein) is induced by addition of an enzyme substrate, e.g., before, after, or together with the enzyme. In some embodiments, phenolic groups on silk fibroin and tyramine-substituted silk fibroin are the substrate for an enzyme used in provided methods. By way of specific example, in some embodiments, when an enzyme (e.g., horseradish peroxidase) is combined with $H_2O_2$ in the presence of phenolic groups, the horseradish peroxidase will catalyze the decomposition of $H_2O_2$ at the expense of aromatic proton donors (i.e. phenol) in a phenol-containing polymer. As such, for example, in some embodiments, silk fibroin (which contain tyrosines) and tyramine-substituted silk fibroin (which contains tyrosines and tyramines) may act as a reducing substrate. In such cases, the reaction ultimately results in phenolic radicals that can form a covalent bonds via condensation of aromatic rings.

In accordance with various embodiments, any of a variety of enzymes may be used to crosslink silk fibroin with one or more phenol-containing polymers. In some embodiments, the enzyme is or comprises a peroxidase. In some embodiments, a peroxidase may be or comprise a plant-based or mammal-based peroxidase. In some embodiments, an enzyme or substrate may be or comprise at least one of hydrogen peroxide, tyrosinase, laccase, hemin, a microperoxidase, cytochrome c, porphyrins, fenton, soy bean peroxidase, myeloperoxidase, lactoperoxidase, eosinophil peroxidase, thyroid peroxidase, prostaglandin H synthase, and horseradish peroxidase. In some embodiments an enzyme substrate is a peroxide. In some embodiments, a peroxide is hydrogen peroxide, barium peroxide, calcium peroxide, sodium peroxide, organic peroxides or combinations thereof.

In some embodiments, methods of providing, preparing, and/or manufacturing a covalently crosslinked hydrogel in accordance with the present invention comprises enzymatically introducing crosslinks. In some embodiments, a method of providing, preparing, and/or manufacturing a covalently crosslinked hydrogel in accordance with the present invention comprises introducing crosslinks with peroxidase (e.g., in the presence of peroxide). In some embodiments, a peroxidase selected from the group consisting of animal heme-dependent peroxidase, bromoperoxidase, glutathione peroxidase, haloperoxidase, horseradish peroxidase, lactoperoxidase, myeloperoxidase, thyroid peroxidase, vanadium and combinations thereof. In some embodiments, a peroxidase is utilized at a concentration between about 0.001 mg/mL and about 10 mg/mL. In some embodiments, a peroxide is selected from the group consisting of barium peroxide, calcium peroxide, hydrogen peroxide, sodium peroxide, organic peroxides and combinations thereof.

In some embodiments, provided compositions (e.g., hydrogels) of the present invention may be provided, prepared, and/or manufactured from a solution of protein polymer (e.g., of silk such as silk fibroin) that is adjusted to (e.g., by dialysis) and/or maintained at a sub-physiological pH (e.g., at or below a pH significantly under pH 7). For example, in some embodiments, a provided composition is provided, prepared, and/or manufactured from a solution of protein polymer that is adjusted to and/or maintained at a pH near or below about 6. In some embodiments, a provided composition is provided, prepared, and/or manufactured from a solution of protein polymer with a pH for instance about 6 or less, or about 5 or less. In some embodiments, a provided composition is provided, prepared, and/or manufactured from a solution of protein polymer with a pH in a range for example of at least 6, at least 7, at least 8, at least 9, and at least about 10.

In some embodiments, an enzyme (e.g., a peroxidase) is utilized in a concentration between, for example: about 0.001 mg/mL and about 100 mg/mL, about 0.001 mg/mL and about 90 mg/mL, about 0.001 mg/mL and about 80 mg/mL, about 0.001 mg/mL and about 70 mg/mL, about 0.001 mg/mL and about 60 mg/mL, about 0.001 mg/mL and about 50 mg/mL, about 0.001 mg/mL and about 40 mg/mL, about 0.001 mg/mL and about 30 mg/mL, about 0.001 mg/mL and about 20 mg/mL, about 0.001 mg/mL and about 10 mg/mL, or about 0.001 mg/mL and about 5 mg/mL. In some embodiments, a solution concentration, for example a peroxidase concentration is: less than about 1 mg/mL, less than about 1.5 mg/mL, less than about 2 mg/mL, less than about 2.5 mg/mL, less than about 3 mg/mL, less than about 3.5 mg/mL, less than about 4 mg/mL, less than about 4.5 mg/mL, less than about 5 mg/mL, less than about 5.5 mg/mL, less than about 6 mg/mL, less than about 6.5 mg/mL, less than about 7 mg/mL, less than about 7.5 mg/mL, less than about 8 mg/mL, less than about 8.5 mg/mL, less than about 9 mg/mL, less than about 9.5 mg/mL, less than about 10 mg/mL, less than about 11 mg/mL, less than about 12 mg/mL, less than about 13 mg/mL, less than about 14 mg/mL, less than about 15 mg/mL, less than about 16 mg/mL, less than about 17 mg/mL, less than about 18 mg/mL, less than about 19 mg/mL, or less than about 20 mg/mL.

In some embodiments, one or more agents or enhancers may be used in accordance with provided methods. By way of specific example, in some embodiments wherein horseradish peroxidase is used, hydrogen peroxide ($H_2O_2$) may also be included, for example, as an oxidizing agent. In some embodiments, an oxidizing agent or enhancer (e.g., hydrogen peroxide) may have a concentration between 0.1 and 100 mM (e.g., between 1 and 100 mM, 10 and 100 mM, 1 and 50 mM, etc).

In some embodiments, a cyclic RGD peptide is added during gelation. The cyclic RGD peptide is crosslinked to the silk fibroin or tyramine-substituted silk fibroin in situ during the enzymatic gelation reaction and no separate chemical reaction is required. In some embodiments, the cyclic RGD peptide is included in an amount of at least about 0.1 mM, at least about 0.2 mM, at least about 0.25 mM, 0.3 mM, at least about 0.4 mM, at least about 0.5 mM, at least about 0.6 mM, at least about 0.7 mM, at least about 0.8 mM, at least about 0.9 mM, or at least about 1.0 mM. In some embodiments, the cyclic RGD peptide is included in an amount between about 0.1 mM and about 1.0 mM, between about 0.2 mM and about 0.8 mM, or between about 0.25 and 0.75 mM.

As described herein, including in the Examples below, provided methods allow for the creation of compositions having any of a variety of enhanced properties.

Typically, a composition (e.g., hydrogel) is formed in vitro for later use. In contrast, some embodiments of provided methods and combinations may be formed in situ. Without wishing to be held to a particular theory, this ability of some embodiments may be due, at least in part, to the mild crosslinking conditions used herein. In some embodiments, provided compositions may be formed during administration or immediately before administration.

Figures 3A, 3B, 3C:
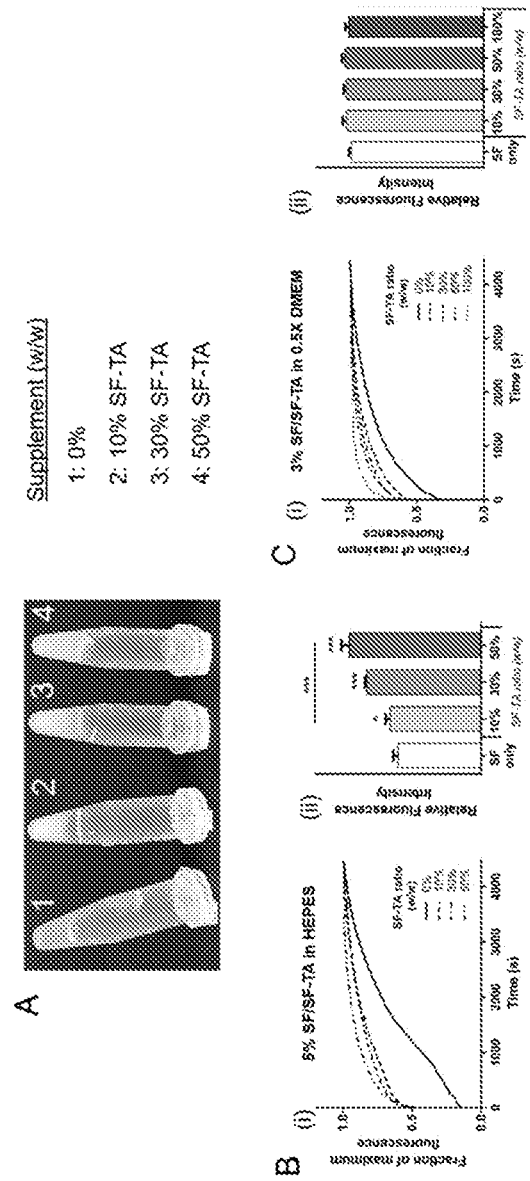
FIGS. 3A-3C show gelation of silk hydrogels supplemented with tyramine-modified silk.

In some embodiments, provided methods and compositions include a very rapid time to gelation. Specifically, in accordance with various embodiments, provided compositions may exhibit any of a range of gelation times. Changes in the ratio of silk fibroin and tyramine-substituted will effect gelation time, as depicted in FIGS. 3A-3C. HRP-mediated crosslinking of unmodified silk fibroin solution prepared in physiological buffers is significantly slower due to relatively higher ionic strength compared to distilled water, and it results in weaker hydrogels. The provided methods and compositions have improved gelation times and improved mechanical properties.

As depicted in FIGS. 3B and 3C, in some embodiments, gelation time is decreased as the concentration of tyramine-substituted silk fibroin is increased. In some embodiments, where a slower gelation time is desired for a particular application, a provided composition may be tuned to gel over a period of approximately 30 minutes to two hours (e.g., between 30 minutes and one hour, between 30 minutes and 90 minutes, or between one hour and two hours).

In some embodiments, where a faster gelation time is desired for a particular application, a provided composition may be tuned to gel over a period of approximately 30 minutes or less (e.g., 25 minutes, 20 minutes, 15 minutes, 10 minutes, 5 minutes, 1 minute, or less). In some embodiments, a provided hydrogel exhibits a gelation time of between 10 seconds and 20 minutes after the crosslinking step (e.g., between 10 seconds and 500 seconds, between 10 seconds and 400 seconds, between 10 seconds and 300 seconds, between 10 seconds and 200 seconds, between 10 seconds and 100 seconds, between 10 seconds and 60 seconds). In some embodiments, the provided hydrogel exhibits a gelation time that occurs within at least 10 seconds, or at least 30 seconds, or at least 60 seconds, or at least 120 seconds, or at least 180 seconds, or at least 200 seconds. In some embodiments, the provided hydrogel exhibits a gelation time that occurs in less than 500 seconds, or less than 450 seconds, or less than 400 seconds, or less than 350 seconds, or less than 300 seconds, or less than 250 seconds. In some embodiments, increasing the relative amount of tyramine-substituted silk fibroin results in a decreased time to gelation. In some embodiments, increasing the concentration of the cyclic RGD peptide results in a decreased time to gelation.

In some embodiments, provided compositions may exhibit improved storage modulus and/or higher strain to failure characteristics. By way of specific example, in some embodiments, provided compositions may exhibit a strain to failure of at least 20% (e.g. at least 30%, 40%, 50%, 60%, 70%, 80%, 90%, 100%, 125%, 150%, or more), while previously known compositions exhibit a strain to failure of at most 10%. In some embodiments, provided compositions may have a storage modulus between 10 Pa-5.5 KPa (e.g., between 10 Pa and 5 KPa, between 10 Pa and 1 KPa, between 100 Pa and 5.5 KPa, between 100 Pa and 1 KPa, etc.). In some embodiments, the provided compositions may have a storage modulus of at least 100 Pa, or at least 200 Pa, or at least 300 Pa, or at least 400 Pa, or at least 500 Pa, or at least 1 kPa, or at least 1.5 kPa, or at least 2 kPa. In some embodiments, the provided compositions may have a storage modulus of less than 2.5 kPa, or less than 3 kPa, or less than 3.5 kPa, or less than 4 kPa, or less than 4.5 kPa, or less than 5 kPa.

In some embodiments, provided compositions may exhibit improved unconfined compressive properties (e.g., compressive modulus). In some embodiments, provided compositions exhibit an increase of 100% or more in the compressive modulus, as compared to compositions not including crosslinking of tyramine-substituted silk fibroin as herein described. By way of additional example, in some embodiments, a provided composition may have a compressive moduli of between 200 Pa and 1 MPa (e.g., between 200 Pa and 500 kPa).

In some embodiments, provided compositions may exhibit improved or altered types of crosslinks as compared to compositions (e.g., gels) created using prior methods. For example, in some embodiments, provided compositions may include primarily (e.g., greater than 50% of the total crosslinks) dityramine crosslinks or tyramine-tyrosine crosslinks. In some embodiments, a provided composition may include substantially only (e.g., greater than 95% of the total crosslinks) dityramine crosslinks. In some embodiments, a provided composition may include substantially only (e.g., greater than 95% of the total crosslinks) tyramine-tyrosine crosslinks.

In some embodiments, provided compositions may exhibit a lower degree of crystallization over time (e.g. beta-sheet crystallization). In some embodiments, provided compositions exhibit substantially no crystallization (e.g. beta-sheet crystallization) over a particular time frame, for example, a week, a month, 3 months, six months, or a year or more. In some embodiments, the amount of crystallization over time may be assessed via FTIR analysis, specifically, by quantifying a shift in the spectra from 1640 $cm^{-1}$ to 1620 $cm^{-1}$. In some embodiments, the shift may be quantified, for example, by determining the ratio of the average peak absorbance at 1620-1625 $cm^{-1}$ and 1640-1650 $cm^{-1}$ which represents the ratio of silk fibroin in beta-sheet configuration as compared that the silk fibroin in random coil configuration. In some embodiments, increasing the relative amount of tyramine-substituted silk fibroin results in a decrease in beta-sheet content.

Generally, an increasing ratio means that there is increasing beta-sheet content as compared to the amount of random coil present in a particular composition. In some embodiments, FTIR spectra may be deconvoluted by fitting a Gaussian curve. In some embodiments, the degree of crystallization in a particular composition may be assessed via x-ray scattering and/or circular dichroism.

In some embodiments, provided compositions may exhibit improved swelling properties. Specifically, in some embodiments, provided compositions may exhibit a mass fraction of at most 1.00 after soaking in an aqueous solution for 12 hours. In some embodiments, provided compositions may have mass fractions of between 0.4-0.99 after soaking in an aqueous solution for 12 hours. In some embodiments, provided compositions may have mass fractions of greater than 1.00 (e.g., greater than 1.1, 1.2. 1.3, 1.4, 1.5, 2.0, 2.5, 5.0, etc) after soaking in an aqueous solution for 12 hours. In some embodiments, provided compositions may exhibit a mass fraction of between 0.4 and 5.0 after soaking in an aqueous solution for 12 hours.

In some embodiments, provided compositions may exhibit a variety of morphologies. In some embodiments, increasing the relative amount of tyramine-substituted silk fibroin results in the provided composition becoming more opaque. In some embodiments, the provided compositions become more opaque as the beta-sheet content increases either as the results of increased storage time or increased relative tyramine-substituted silk fibroin content.

In some embodiments, provided compositions may exhibit tunable in vivo and in vitro enzymatic degradation properties. In some embodiments, upon exposure to a protease, the compositions provided herein lose about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% of the original mass of the composition. In some embodiments, the compositions lose at least about 10% of the original mass after about 1 day, about 2 days, about 3 days, about 4 days, about 5 days, about 6 days, or about 7 days, or about 8 days when exposed to a protease.

In some embodiments, upon exposure to a protease, the compositions retain at least about 30%, or at least about 40%, or at least about 50%, or at least about 60%, to less than 70%, or less than 80%, or less than 85%, or less than 90% of the original mass thereof for a duration (e.g., 1 to 8 days). In some embodiments, the duration is at least about 1 day, at least about 2 days, at least about 3 days, at least about 4 days, to less than about 5 days, or less than about 6 days, or less than about 7 days, or less than about 8 days. In some embodiments, increasing the relative amount of tyramine-substituted silk fibroin results in reduced or delayed degradation of the composition upon exposure to a protease.

In some embodiments, an example test method for determining the retention of mass for the provided compositions includes preparing a hydrogel disk from a 200 µL solution in a cylindrical mold having a 1 cm diameter, and incubating the solution in a buffer (e.g., DPBS) at room temperature for a duration to induce gelation. The gelation duration may range from 1 hour to 6 hours, e.g., at least 1 hour, at least 2 hours, at least 3 hours, to less than 4 hours, less than 5 hours, or less than 6 hours. The hydrogel disk may then be transferred into a solution of 300 µL of 0.001 U/mL of protease (e.g., type XIV from *Streptomyces griseus*) dissolved in a buffer (e.g., DPBS) to induce degradation over a duration. The degradation duration may be from 1 day to 8 days (e.g., at least 1, 2, 4, 6, 8 days, or more). In some embodiments, the enzyme solution is changed every 2 days over the course of the degradation duration. After removal of the enzyme solution, hydrogels are washed in purified or distilled water (e.g., Ultrapure™ distilled water) at room temperature, lyophilized, and weighed. Results are reported as a mass fraction of the initial weight at day zero.

In some embodiments, the provided compositions may exhibit tunable bioactivity, such as improved integrin mediated cell adhesion, spreading and organization of actin cytoskeleton, modulation of cell survival, proliferation, and differentiation via mechanotransduction. Incorporating cyclic RGD peptides into the provided compositions reduces the susceptibility to enzymatic degradation, improves cell-matrix interactions to a higher degree by binding selectively to $\alpha_v\beta_3$ and $\alpha_v\beta_5$ integrins with higher affinity compared to linear counterparts.

Figures 12A, 12B, 12C, 12D:
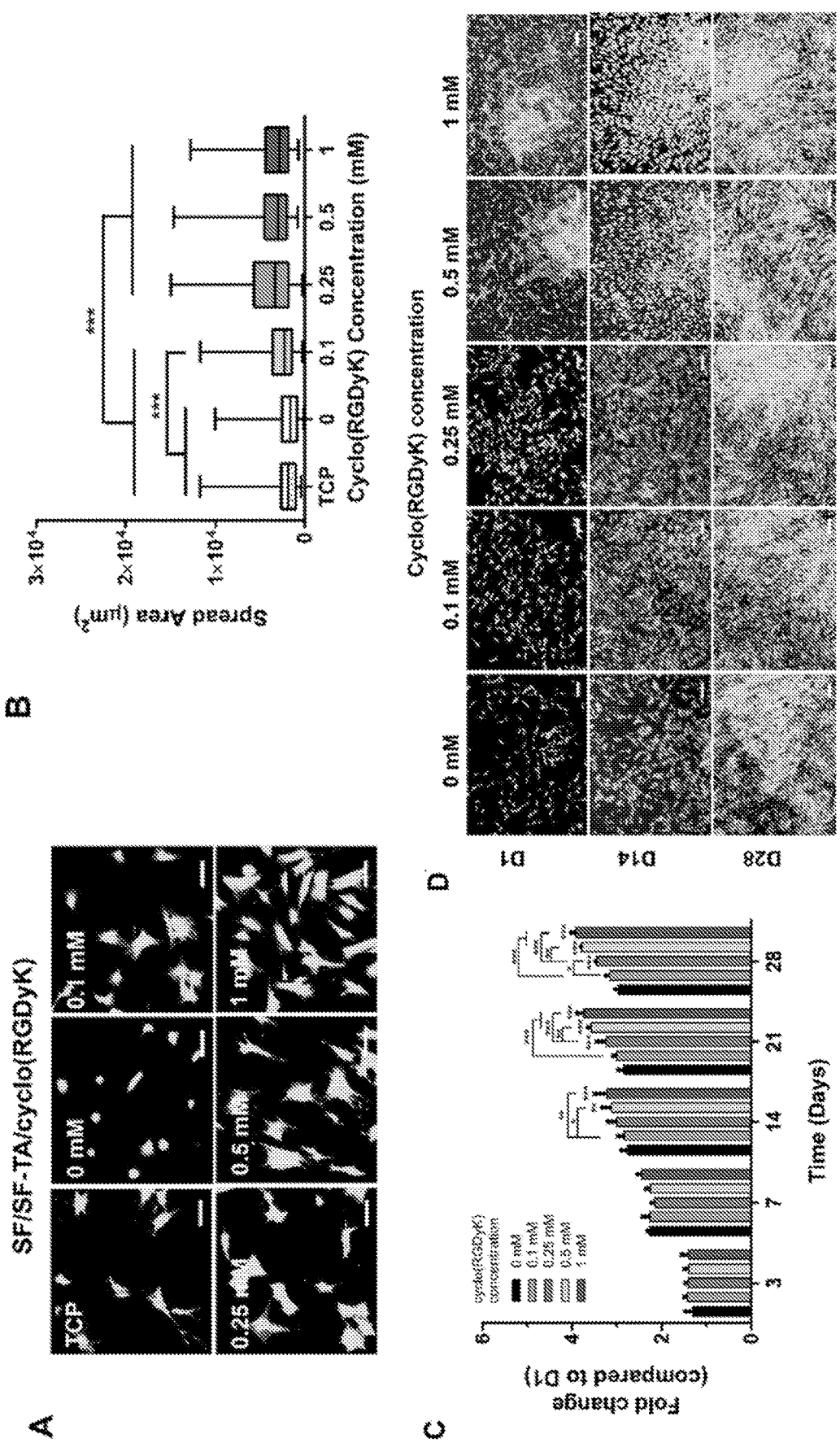
FIGS. 12A-12D show hMSCs behavior on 5% SF/SF-TA composite hydrogels supplemented with cyclo(RGDyK).

In some embodiments, the bioactivity of the provided compositions is measured using area of cell spreading after 24 hours on a surface of the provided composition. In some embodiments, the provided compositions are first coated on a substrate. Suitable test substrates include, but are not limited to, tissue culture plastic (TCP) (e.g., polystyrene). In some embodiments, the area of cell spreading on a surface of the provided compositions after 24 hours ranges from a median value of at least 2000 $\mu m^2$, or at least 2500 $\mu m^2$, or at least 3000 $\mu m^2$, or at least 3500 $\mu m^2$, to less than 4000 $\mu m^2$, or less than 4500 $\mu m^2$, or less than 5000 $\mu m^2$, or less than 5500 $\mu m^2$, or less than 6000 $\mu m^2$. The presence of a cyclic RGD peptide improves bioactivity and the area of cell spreading. As shown in FIG. 12B, the area of cell spreading on TCP without the provided compositions exhibited a round morphology after 24 hours, and had a median value of 1500 $\mu m^2$ after 24 hours. Compared to the TCP control and the provided composition without a cyclic RGD peptide, the area of cell spreading for provided compositions having the cyclic RGD peptide exhibited a flattened geometry and demonstrated improved spread over the surface of the provided composition.

In some embodiments, the bioactivity of the provided compositions is measured using a fold change in metabolic activity of cells on a surface of the provided compositions over a duration. The fold change is a measure of metabolic activity over the duration of culture compared to the metabolic activity on day 1 of culture. In some embodiments, the fold change of metabolic activity of the cells ranges from 1 to 4. In some embodiments, the fold change of metabolic activity of the cells is at least 1, or at least 1.25, or at least 1.5, or at least 1.75, or at least 2, or at least 2.25, or at least 2.5, or at least 2.75, to less than 3, or less than 3.25, or less than 3.5, or less than 3.75, or less than 4. In some embodiments, the duration of the fold change measurements ranges from 2 day to 28 days. In some embodiments, the duration is at least 2 days, at least 3 days, at least 4 days, at least 5 days, at least 6 days, at least 7 days, to less than 14 days, to less than 21 days, or less than 28 days.

In some embodiments, an example test method for measuring the area of cell spreading and/or a fold change of metabolic activity may include depositing a composition provided herein on the substrate, and seeding cells on a surface of the provided composition at a cell density (e.g., at least 1,000 cells/cm$^2$, or at least 2,000 cells/cm$^2$, or at least 3,000 cells/cm$^2$, to less than 4,000 cells/cm$^2$, or less than 5,000 cells/cm$^2$). Exemplary cells for the test include, but are not limited to, human bone marrow mesenchymal stem cells (hMSCs). The cells may then be submerged in a volume of growth medium, and allowed to spread over the surface of the provided composition for a duration (e.g., 24 hours for the area of cell spreading, or from 1 day to 28 days for the metabolic activity). Suitable growth mediums include, but are not limited to, Dulbecco's Modified Eagle Medium supplemented with or without 10% fetal bovine serum, 1% Penicillin-Streptomycin, 1% non-essential amino acids, and 1% ng/mL of fibroblast growth factor-2). Suitable volumes of growth medium range from 0.5 mL to 5 mL (e.g., at least 0.5 mL, at least 1 mL, at least 2 mL, to less than 3 mL, or less than 4 mL, or less than 5 mL). The cells may be stained and fluorescence images of the cells may be analyzed using imaging software (e.g., ImageJ, 1.48v, NIH, USA) to quantify area of cell spreading. Metabolic activity of the cells may be determined at the specified duration using a metabolic activity assay, such as alamarBlue viability assay (Invitrogen, Carlsbad, CA). The fold change for surface metabolic activity is a measure of the increase in percentage of dye present at the specified duration after normalization to initial measurements at day 1.

In some embodiments, the bioactivity of the provided compositions is measured using a fold change in metabolic activity of cells that are encapsulated in the provided compositions. The fold change of cells encapsulated in the provided compositions is a measure of the decrease in percentage of dye present at the specified duration after a normalization to initial measurements at day 1. In some embodiments, the fold change of metabolic activity of the encapsulated cells is ranges from 0.1 to 2.5 over the duration. In some embodiments, the fold change of metabolic activity of the encapsulated cells ranges less than 2.5, or less than 2.25, or less than 2, or less than 1.75, or less than 1.5, or less than 1.25, or less than 1, or less than 0.75, to at least 0.5, or at least 0.25, or at least 0.1. In some embodiments, the duration of the fold change measurements for encapsulated cells ranges from 2 day to 28 days. In some embodiments, the duration is at least 2 days, at least 3 days, at least 4 days, at least 5 days, at least 6 days, at least 7 days, to less than 14 days, to less than 21 days, or less than 28 days.

In some embodiments, an example test method for measuring a fold change of metabolic activity of encapsulated cells may include depositing a composition provided herein into a well-plate with cells at a concentration (e.g., at least 1×10$^5$ cells/mL, or at least 2×10$^5$ cells, to at least 3×10$^5$ cells/mL, to less than 4×10×10$^5$ cells/mL, or less than 5×10$^5$ cells/mL). Exemplary cells for the test include, but are not limited to, human bone marrow mesenchymal stem cells (hMSCs). The wells may be flooded with a volume of growth medium, and allowed to culture for a duration (e.g., from 1 day to 28 days for the metabolic activity). Suitable growth mediums include, but are not limited to, Dulbecco's Modified Eagle Medium supplemented with or without 10% fetal bovine serum, 1% Penicillin-Streptomycin, 1% non-essential amino acids, and 1% ng/mL of fibroblast growth factor-2). Suitable volumes of growth medium range from 0.5 mL to 5 mL (e.g., at least 0.5 mL, at least 1 mL, at least 2 mL, to less than 3 mL, or less than 4 mL, or less than 5 mL). The growth medium may be changed every 3 days. Metabolic activity of the cells may be determined at the specified duration using a metabolic activity assay, such as alamarBlue viability assay (Invitrogen, Carlsbad, CA). The fold change for encapsulated cell metabolic activity is a measure of the decrease in percentage of dye present at the specified duration after normalization to initial measurements at day 1.

Figure 15:
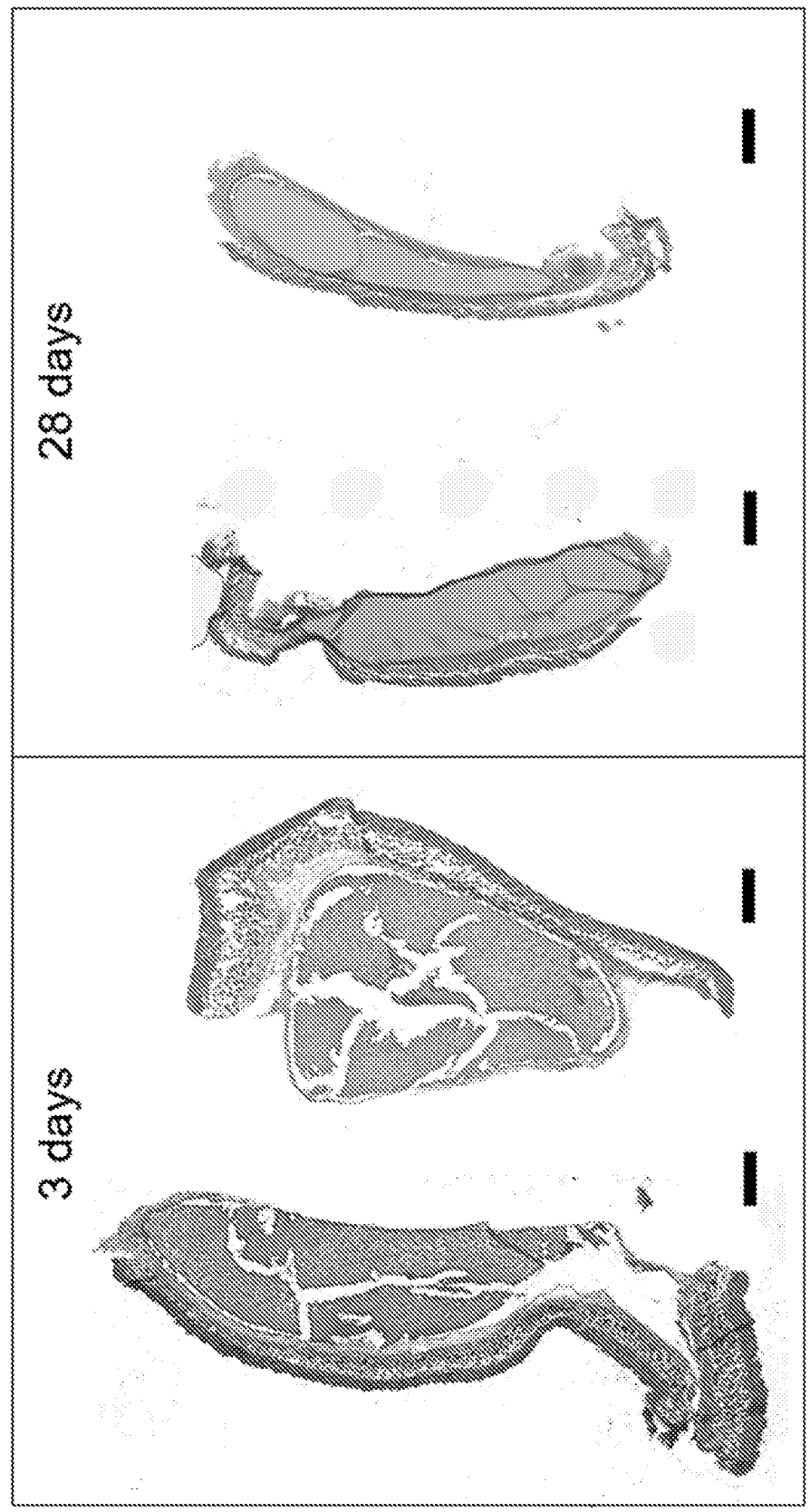
FIG. 15. Hematoxylin and eosin stained slices of cutaneous tissues containing SF-TA hydrogel discs at 3 or 28 days. Scale bars: 1 mm.

In some embodiments, provided compositions may retain at least a portion of an original volume and/or mass after implantation in vivo over a duration. In some embodiments, provided compositions may retain at least 30% of an original volume and/or mass after implantation in vivo, or at least 40%, or at least 50%, or at least 60%, or at least 70%, or at least 80% of the original volume and/or mass after implantation in vivo. In some embodiments, the duration is at least 1 day, or at least 2 days, or at least 3 days, or at least 4 days, or at least 5 days, or at least 6 days, or at least 7 days, to less than 14 days, or less than 21 days, or less than 28 days. As shown in FIG. 15, implanted compositions may retain at least a portion of the original volume and/or mass after 28 days in vivo.

In some embodiments, provided compositions (e.g., hydrogels) can comprise one or more (e.g., one, two, three, four, five or more) active agents and/or functional moieties (together, "additives"). Without wishing to be bound by a theory, an additive can provide or enhance one or more desirable properties, e.g., strength, flexibility, ease of processing and handling, biocompatibility, bioresorability, surface morphology, release rates and/or kinetics of one or more active agents present in the composition, and the like. In some embodiments, one or more such additives can be covalently or non-covalently linked with a composition (e.g., with a polymer such as silk fibroin that makes up the hydrogel) and can be integrated homogenously or heterogeneously (e.g., in a gradient or in discrete portions of a provided composition) within the silk composition.

In some embodiments, an additive is or comprises a moiety covalently associated (e.g., via chemical modification or genetic engineering) with a polymer (e.g., silk fibroin or tyramine-substituted silk fibroin). In some embodiments, an additive is non-covalently associated with a hydrogel or hydrogel component.

In some embodiments, provided compositions (e.g., hydrogels) comprise additives at a total amount from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided compositions (e.g., hydrogels) include one or more additives at a molar ratio relative to polymer (i.e., a polymer:additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety polymer:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety polymer:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, provided compositions (e.g., hydrogels) comprise additives, for example, therapeutic, preventative, and/or diagnostic agents.

In some embodiments, an additive is or comprises one or more therapeutic agents.

In general, a therapeutic agent is or comprises a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or comprises an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, provided compositions (e.g., hydrogels) comprise additives, for example, cells. In some embodiments, methods of using provided compositions may comprise adhering cells to a surface of a covalently crosslinked hydrogel. In some embodiments, methods of using provided compositions may comprise encapsulating cells within a matrix a covalently crosslinked hydrogel. In some embodiments, methods of using provided compositions may comprise encapsulating cells for introducing cells to a native tissue. Cells suitable for use herein include, but are not limited to, progenitor cells or stem cells (e.g., mesenchymal stem cells), smooth muscle cells, skeletal muscle cells, cardiac muscle cells, glial cells (e.g., astrocytes), neurons, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. In some embodiments, cells are adhered to or encapsulated in compositions comprising covalently crosslinked tyramine-substituted silk fibroin and a cyclic RGD peptide.

In some embodiments, provided compositions (e.g., hydrogels) comprise additives, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Figures 16A, 16B:
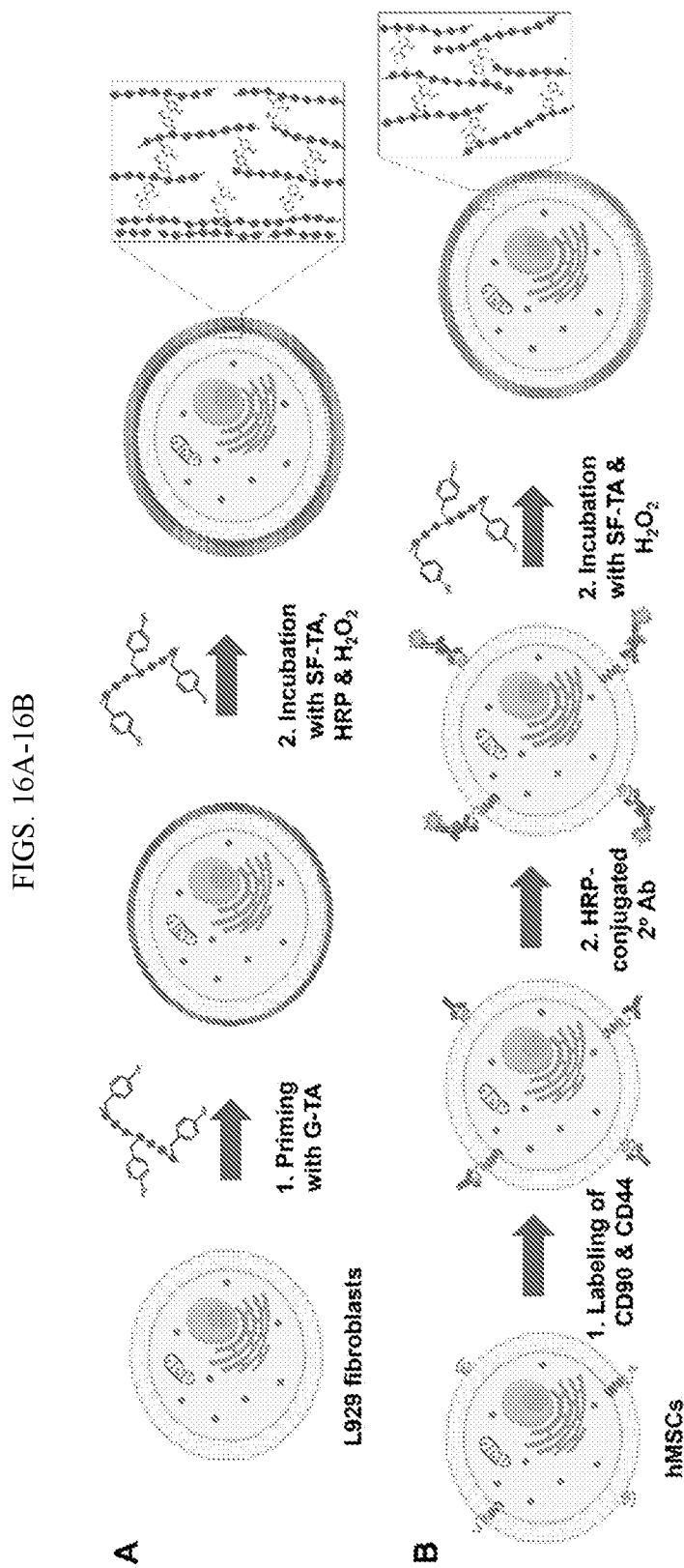
FIGS. 16A-16B show schematic illustrations of nanoencapsulation of individual mammalian cells within covalently crosslinked SF-TA hydrogel nanolayers.

Referring to FIGS. 16A-16B, in some embodiments, provided compositions may encapsulate individual cells. In some embodiments, the provided compositions form nanolayers that encapsulate the individual cells. In some embodiments, a priming protein polymer comprising phenol groups is coupled to the external surface of the individual cell. The priming protein polymer may have a positive charge that becomes electrostatically coupled to the external surface of the cell, which has a negative charged cell surface. Suitable priming protein polymers include elastin, chitosan, collagen, gelatin, agarose, alginate, chitin, polyhydroxyalkanoates, pullan, starch, cellulose, hyaluronic acid, polydimethylsiloxane, poly(lactide-co-glycolide), resilin, poly(ethylene glycol). The priming protein polymer may be covalently bonded to either a tyramine-substituted silk fibroin, a tyrosine group of an unmodified silk fibroin, or combinations thereof. The tyramine-substituted silk fibroin and/or unmodified silk fibroin may form a second nanolayer that surrounds the priming protein layer. In some embodiments, each of these nanolayers completely surrounds the cell.

In some embodiments, individually encapsulated cells may be formed from a method that includes priming an exterior surface of the cell with the priming protein polymer. The priming protein polymer may first be modified to contain an increased phenol content (e.g., tyramine or tyrosine). The increased phenol content may be achieved using the methods described herein for producing tyramine-substituted silk fibroin (e.g., coupling the phenol to the protein using EDC and NHS). The method further includes contacting tyramine-substituted silk fibroin and/or unmodified silk fibroin to the priming protein polymer and crosslinking a phenol group of the protein polymer to a phenol group in the tyramine-substituted silk fibroin and/or unmodified silk fibroin. The ratios of tyramine-substituted silk fibroin to unmodified silk fibroin may be the same as those described above.

Referring to 16B, the tyramine-substituted silk fibroin and/or unmodified silk fibroin may be directly coupled to the exterior surface of the cell. In some embodiments, the tyramine-substituted silk fibroin and/or unmodified silk fibroin completely surround the individual cell in a nanolayer or multiple nanolayers of covalently crosslinked tyramine-substituted silk fibroin and/or unmodified silk fibroin.

In some embodiments, individually encapsulated cells may be formed from a method that includes conjugating an enzyme to a surface of the cell. An antibody may be used to form enzyme-conjugated antibody complexes on the surface of the cell. A phenol containing polymer, tyramine-substituted silk fibroin, unmodified silk fibroin, or combinations thereof may then be contacted to the external surface of the cell along with a substrate for the enzyme (e.g., hydrogen peroxide) to induce localized covalent crosslinking. The localized covalent crosslinking may form a nanolayer that encapsulates the individual cell.

In some embodiments, provided compositions (e.g., hydrogels) comprise additives, for example, antibiotics. Antibiotics suitable for incorporation in various embodiments include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, provided compositions (e.g., hydrogels) comprise additives, for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, provided compositions (e.g., hydrogels) comprise additives, for example, antibodies. Suitable antibodies for incorporation in hydrogels include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, provided compositions (e.g., hydrogels) comprise additives, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided compositions (e.g., hydrogels) comprise additives, for example, particularly useful for wound healing. In some embodiments, agents useful for wound healing include stimulators, enhancers or positive mediators of the wound healing cascade (e.g., wound healing growth factors) which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided compositions (e.g., hydrogels) comprise additives, for example, an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

In some embodiments, provided compositions (e.g., hydrogels) comprise additives, for example, nucleic acid agents. In some embodiments, a composition may release nucleic acid agents. In some embodiments, a nucleic acid agent is or comprises a therapeutic agent. In some embodiments, a nucleic acid agent is or comprises a diagnostic agent. In some embodiments, a nucleic acid agent is or comprises a prophylactic agent.

It will be appreciated by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or comprise deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or comprises at least one protein-coding element. In some embodiments, a nucleic acid has a nucleotide sequence that is or comprises at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or comprises an oligonucleotide. In some embodiments, a nucleic acid agent is or comprises an antisense oligonucleotide. Nucleic acid agents may include a chemical modification at the individual nucleotide level or at the oligonucleotide backbone level, or it may have no modifications.

In some embodiments of the present invention, a nucleic acid agent is an siRNA agent. Short interfering RNA (siRNA) comprises an RNA duplex that is approximately 19 basepairs long and optionally further comprises one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to comprise sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase IB (PTP1B).

In some embodiments, provided compositions (e.g., hydrogels) comprise additives, for example, one or more growth factors. In some embodiments, a provided composition may release one or more growth factors. In some embodiments, a provided composition may release multiple growth factors. In some embodiments growth factors known in the art include, for example, adrenomedullin, angiopoietin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided compositions (e.g., hydrogels) comprise additives, for example, that are particularly useful for healing. Exemplary agents useful as growth factors for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFp3, TGFp1, and TGFp2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, FIB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof, INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox® lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that growth factor agents useful for healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, provided compositions (e.g., hydrogels) comprise additives, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, provided compositions (e.g., hydrogels) comprise additives, for example, that are or comprise fluorescent and/or luminescent moieties.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication No. 2004/0067503; Valeur, B., "Molecular Fluorescence: Principles and Applications," John Wiley and Sons, 2002; Handbook of Fluorescent Probes and Research Products, Molecular Probes, 9$^{th}$ edition, 2002; and The Handbook—A Guide to Fluorescent Probes and Labeling Technologies, Invitrogen, 10$^{th}$ edition, available at the Invitrogen web site; both of which are incorporated herein by reference).

In accordance with various embodiments, provided compositions may take any of several forms. In some embodiments, a provided composition may be or comprise a tube, particle, film, foam, wire, hydrogel, etc. In some embodiments, a provided composition may be or comprise a lyophilized form of a tube, particle, film, foam, wire, etc. In some embodiments, a provided composition may be or comprise a hydrogel. In some embodiments, a provided composition may further include an additional structure such as a tube, particle, film, foam, wire, hydrogel, etc. In some embodiments, a provided composition may be partially or totally encapsulated in an additional structure. In some embodiments, a provided composition may partially or totally encapsulate an additional structure.

In some embodiments, a provided composition is configured to be injectable. In some embodiments, a viscosity of an injectable composition is modified by using a pharmaceutically acceptable thickening agent. In some embodiments, a thickening agent, for example, is methylcellulose, xanthan gum, carboxymethyl cellulose, hydroxypropyl cellulose, carbomer, or combination thereof. A preferred concentration of the thickener depends upon a selected agent and viscosity for injection.

As will be recognized by one of skill in the art, previously known hydrogel compositions are typically made from synthetic and natural polymers, for example, polyesters, polyurethanes, polyethers, elastin, resilin. Synthetic polymers have also been developed that exhibit high resilience and recovery from both applied tensile and compressive forces.

Poly(glycerol sebacate) (PGS) for example has shown utility as a scaffold for engineering vascular, cardiac, and nerve tissues. Additionally, synthetic bioelastomers based on polyurethanes, including for examples variants of poly(ethylene glycol), poly(8-caprolactone), and poly(vinyl alcohol), modified with degradable segments have also been developed and used for soft tissue, bone, and myocardial repairs. The present disclosure encompasses the recognition of significant drawback, however, that are often associated with traditional hydrogels, both natural and synthetic. For example, although desirable features such as tunable mechanics, cell encapsulation attributes, biocompatibility, biodegradability or elasticity have been reported for certain traditional hydrogels, the present disclosure appreciates that, in general, such traditional hydrogels cannot offer a combination of all of these characteristics.

By way of specific example, previously developed hydrogel technologies typically lack certain of the mechanical properties described for hydrogels herein, and/or lack the ability to specifically tune such properties, e.g., via production methodologies. Alternatively or additionally, previously developed hydrogel technologies typically lack certain of the favorable degradation mechanics provided by hydrogels described herein and/or lack the ability to specifically tune such properties. Still further, in many cases, traditional hydrogels fail to display certain degradation properties described for hydrogels provided herein; rapid degradation of such previously-developed hydrogels often limits their use to short term scaffolding. Yet further, in many cases, traditional hydrogel technologies require organic solvents during processing, which can result in toxicity, can interfere with cell or protein encapsulation (and particularly with maintenance of structural and/or functional integrity of encapsulated entities), and cannot resist long term strains when incorporated in vivo.

Further, many traditional hydrogels form, at least in part, through physical entanglements and hydrogen bonding between hydrophobic domains, resulting in β-sheet formation, β-sheet crystals have been shown to provide structure, strength, and long term stability of hydrogels. However, β-sheet crystals also display brittle behavior, as the crystals prevent long range displacements. Accordingly, and as described herein, provided compositions, including those in hydrogel form, provide sophisticated control and/or balance of such properties.

In accordance with various embodiments, provided herein with a method of printing silk fibroin hydrogels. The printed silk fibroin hydrogels may include unsubstituted silk fibroin, tyramine substituted silk fibroin, cyclic RGD peptide, an active agent, and combinations thereof. An aqueous solution comprising silk fibroin (e.g., unsubstituted silk fibroin and/or tyramine substituted silk fibroin) and a carrier is prepared. The carrier can be a solvent or dispersing medium, such as, but not limited to, water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, HEPES, Hank's balanced medium, Roswell Park Memorial Institute (RPMI) medium, fetal bovine serum, or suitable combinations and/or mixtures thereof. The aqueous silk fibroin solution is split into at least two separate portions; (i) a first portion of the silk fibroin solution including horseradish peroxidase or another suitable peroxidase enzyme as described herein; and (ii) a second portion of the silk fibroin solution including hydrogen peroxide or another suitable peroxide as described herein. Either or both portions may further include a cyclic RGD peptide and/or an active agent. Additional portions of the silk fibroin solution may be prepared which include unsubstituted silk fibroin, a cyclic RGD peptide, other phenolic-containing polymers, or combinations thereof. The portions are combined during printing (e.g., bioprinting or 3D printing), whereby gelation occurs. Printing of silk fibroin hydrogels as described herein is not limited to combining the first and second portions, and may also including combining a third, fourth, fifth, sixth, seventh or greater portions to achieve the desired properties. Suitable 3D printers and bioprinters are known and used in the art and available commercially. In some embodiments, the portions of the silk fibroin solution are mixed using a syringe pump and a 2-inlet needle (e.g., a co-axial needle) or a co-axial nozzle. In some embodiments, the portions are mixed at a flow rate between about 0.1 ml/min and about 1.0 ml/min. In some embodiments, the portions are mixed at a flow rate of about 0.5 ml/min. The portions may be printed onto any suitable surface known in the art. Suitable surfaces include, but are not limited to, glass, plastic, rubber, cell culture plates, cell culture plates coated with a substrate, or the like. In general, rapid gelation and an increase in opacity can be observed upon mixing of the portions, which can be tuned and controlled based on the concentration of the tyramine-substituted silk fibroin solution and other factors.

In accordance with various embodiments, provided herein are compositions comprising silk fibroin hydrogel microbeads. The silk fibroin hydrogel microbeads may include unsubstituted silk fibroin, tyramine substituted silk fibroin, cyclic RGD peptide, an active agent, and combinations thereof. The silk fibroin hydrogel microbeads include chemically crosslinked silk fibroin. In some embodiments, the hydrogel microbeads are between 5 µm and 50 µm in diameter. In some embodiments, the hydrogel microbeads are between 8 µm and 40 µm in diameter. In some embodiments, the hydrogel microbeads are between 10 µm and 30 µm in diameter.

The hydrogel microbeads may be formed using co-flow microfluidics. The co-flow microfluidic methods including mixing an aqueous solution and an oil or lipid phase solution. In some embodiments, the aqueous solution and the oil/lipid phase solution are mixed at a flow rate between about 0.001 ml/min and 3 ml/min. In some embodiments, the flow rate of the for the oil/lipid phase solution is higher than the flow rate for the aqueous solution. In some embodiments, the flow rate of the oil/lipid phase solution is between 1.5 ml/min and 2.5 ml/min. and the aqueous phase flow rate is between 0.001 ml/min and 0.5 ml/min. In some embodiments, the oil/lipid phase solution is between 1.8 and 2.2 ml/min. and the aqueous phase flow rate is between 0.01 and 0.1 ml/min. In some embodiments, the solutions are mixed through a co-axial nozzle or a co-axial needle. The aqueous solution includes a carrier, silk fibroin, and horseradish peroxidase or another suitable peroxidase enzyme as described herein. The silk fibroin in the aqueous solution may be unsubstituted silk fibroin or tyramine-substituted silk fibroin. The carrier can be a solvent or dispersing medium, such as, but not limited to, water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, HEPES, Hank's balanced medium, Roswell Park Memorial Institute (RPMI) medium, fetal bovine serum, or suitable combinations and/or mixtures thereof. The oil or lipid phase solution includes hydrogen peroxide or another suitable peroxide as described herein, a surfactant, and a lipid or oil. The surfactant may be any suitable surfactant known in the art. The lipid or oil may be any lipid or oil known in the art suitable for use in microfluidic devices.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The present invention has been described in terms of one or more preferred embodiments, and it should be appreciated that many equivalents, alternatives, variations, and modifications, aside from those expressly stated, are possible and within the scope of the invention.

Example 1

It is known that the increasing number of phenol groups on polymer chains improve gelation speed and mechanical properties of HRP/$H_2O_2$-crosslinked hydrogels by increasing the crosslinking density[31]. Modulation of gelation kinetics by using tyramine-substituted SF is proposed as a safer approach compared to increasing HRP[32, 33] and/or $H_2O_2$[34] concentrations. In addition to increasing the total phenol content, tyramine-substitution on SF is expected to provide more accessible phenol residues even at high ionic strength considering that aspartic and glutamic acid residues are in the amorphous regions of SF unlike tyrosine residues, a large portion of which is found in semi-crystalline hydrophobic domains[35]. The advantage of SF-TA over the other phenol-conjugated proteins or polysaccharides is that since SF is already rich in tyrosine residues, tyramine-substituted silk can be crosslinked with unmodified silk at any weight ratio for fine tuning of crosslinking density to modulate gelation kinetics and mechanical properties of the resulting hydrogels without altering HRP or $H_2O_2$ concentrations. Rapid gelation of relatively low concentration SF-TA solutions in physiological buffers allows for in situ crosslinking during 3D printing or fabrication of hydrogel microspheres using microfluidics approach.

Arginine-glycine-aspartic acid (RGD) sequence is found in many extracellular matrix (ECM) proteins such as vitronectin, fibrinogen, collagen and laminin, and it is known to regulate integrin mediated cell adhesion, spreading and organization of actin cytoskeleton, which further modulate survival, proliferation, and differentiation via mechanotransduction[36]. Cyclic RGD peptides were shown to display lower susceptibility to enzymatic degradation[37] and improve cell-matrix interactions to a higher degree by binding selectively to $\alpha_v\beta_3$ and $\alpha_v\beta_5$ integrins with higher affinity compared to linear counterparts[38, 39]. Therefore, in situ conjugation of cyclic RGD peptides is proposed to improve the bioactivity of SF/SF-TA silk composite hydrogels. The present disclosure describes the in situ conjugation of a cyclic RGD peptide with a tyrosine residue into an enzymatically crosslinked hydrogel matrix to introduce integrin-binding ligands. The strategy also eliminates the step of covalent conjugation of RGD peptides on SF chains before hydrogel crosslinking.

Different chemical groups, peptides and biochemical agents have been covalently conjugated to silk biomaterials through a variety of chemistries, including carbodiimide coupling, cyanuric chloride-activated or diazonium salt coupling on tyrosine residues[40], and nucleophilic substitution of deprotonated serine hydroxyl groups at methyl group of α-haloacetyl compounds[41]. Direct carbodiimide coupling on aspartic and glutamic acid side chains in the amorphous domains of silk fibroin has been the most widely employed approach to conjugate new functionalities with a primary amine group including enzymes such as HRP into porous silk sponges[42] and cholesterol oxidase on woven silk mats[43]; large molecules such as NeutrAvidin on silk microspheres or protein in solution[44]; growth factors such as parathyroid hormone (PTH) on silk films[45]; proteins such as wheat germ agglutinin (WGA) on silk protein in solution; and integrin binding arginine-glycine-glutamic acid (RGD) or titanium binding, laminin-derived, or antimicrobial peptides on silk protein in solution[46, 47] as well as silk biomaterials in various forms[48-52]. The same strategy was also used to introduce charged polyamino acids on tyrosine and serine-carboxylated silk fibroin to synthesize silk-based ionomers[53-57]. Coupling of tyramine groups have been reported on several natural or synthetic polymers such as gelatin[31, 58], poly(glutamic acid) (PGA)[59], hyaluronic acid (HA)[60-63], dextran[64-66], alginate[67, 68], heparin[69], cellulose[70], chondroitin sulfate[71], poly(vinyl alcohol) (PVA)[72] and poly(ethylene glycol) (PEG)[73] to enable enzymatic crosslinking of their aqueous solutions, but it has not been performed on silk before to modulate its gelation kinetics. Unlike these polymers, unmodified silk is already rich in phenol groups from the tyrosine residues and therefore it can be crosslinked with tyramine-substituted silk at any weight ratio for fine-tuning of the gelation kinetics without altering the concentration of HRP or $H_2O_2$.

Silk fibroin-based hydrogels have been fabricated before via physical or covalent crosslinking of aqueous silk solution. Physical crosslinking has been achieved through induction of R-sheet formation by applying shearing forces using vortex[74] or sonication[75]; lowering of solution pH towards isoelectric point of fibroin[76, 77]; or polyalcohol treatment[78]. Physical crosslinking of silk-based hydrogels has been utilized before for 3D printing or fabrication of micro/nanoparticles. Examples include self-curing silk bioinks physical crosslinking of which was induced by polyalcohols such as glycerol[79, 80] or poly(ethylene glycol) (PEG)[80, 8]. Similarly, micro- and submicron silk microspheres were fabricated by inducing physical crosslinking with methanol[82] or PEG[83] in the continuous phase using a co-flow capillary device. The silk concentration in these formulations, however, was very high (>10% w/v), which result in high stiffness[22] and low porosity[83] that are known to impair viability and proliferation of encapsulated cells in hydrogel matrices[84]. Besides genipin crosslinking of amine groups on the lysine residues[85] or photocrosslinking of methacryate groups covalently conjugated on silk fibroin[86], oxidation of tyrosine residues into dityrosine bridges by tyrosinase-catalysis[87], riboflavin-mediated photoactivation[88], HRP/$H_2O_2$[22] or Fe(III) ion-mediated Fenton reaction[89] has also been used for covalent crosslinking and used as injectable tissue fillers[90], bioink for 3D bioprinting applications using a sacrificial alginate template [91] as well as for fabrication of scaffolds for tissue engineering[92, 93] and regeneration[94], elastometic fibers[23], microfluidic devices[95], or lenses for optoelectronic applications[96]. Cell encapsulation has been reported in both physically and enzymatically crosslinked hydrogels, but gelation was slow, and the cells were added some time (~10 min) after gelation was induced by vortex[74], sonication[75] or HRP/$H_2O_2$ reaction[22, 25] to prevent sedimentation of the cells. This approach, however, is not practical in bioprinting or droplet-based microencapsulation applications. Faster enzymatic crosslinking can be achieved by increasing the concentration of HRP[32, 33] and/or $H_2O_2$[34], which may raise concerns of immunological responses in vivo[35, 97] and apoptotic or necrotic cytotoxicity[98], respectively. Adding phenol red in silk solution was also found to increase gelation speed through bonding of phenolic hydroxyl groups to silk tyrosine side chains[25], but the red color of the hydrogels and the risk of dye leakage at high concentrations may raise aesthetic and cytotoxicity concerns, respectively. Silk solutions blended with tyramine-substituted hyaluronic acid were shown to gel significantly faster compared to silk only control, but high viscosity and hydrophilicity of HA were stated as issues for effective mixing of the two polymers[99]. Thus, tyramine-substitution of silk fibroin introduced here provides a safer and more practical approach for faster enzymatic gelation of aqueous silk solutions, particularly in physiological buffers for cell encapsulation.

Lack of cell recognition sequences in the primary structure of silk fibroin has been identified as a potential issue in terms of proper interactions of the encapsulated cells with the silk hydrogel matrices, which was addressed by others by blending silk solution with ECM components such as collagen[100], gelatin[101-110] cardiac ECM[92]; or by carbodiimide coupling of ECM-derived peptides such as IKVAV on SF prior to physical crosslinking[113] Linear RGD peptides were tethered onto silk films[48-50], fibers[51], and nanofibrous mats[52] via carbodiimide coupling and their bioactivity was improved significantly. Tyramine-substituted silk, however, cannot be coupled with RGD peptides via carbodiimide reaction since aspartic and glutamic acid residues are already occupied by the tyramine groups. Instead, in situ conjugation of cyclic RGD peptides with a tyrosine into the hydrogels during enzymatic crosslinking was employed here to improve cell-matrix interactions of the hydrogels. This strategy does not require an additional step of chemical modification and can be employed for the hydrogels of unmodified silk as well.

Fabrication of SF/SF-TA composite hydrogels supplemented with cyclo(RGDyK) for encapsulation of human mesenchymal stem cells—Silk fibroin of B. mori includes two chains linked by a disulphide bond: a light chain with a molecular weight of 26 kDa and a heavy chain with a molecular weight of 391 kDa. The primary structure of the heavy chain has 4 distinct motifs: a highly repetitive GAGAGS sequence (SEQ ID NO:1) and relatively less repetitive GAGAGSGAAS sequences (SEQ ID NO:2) that form the crystalline regions, GAGAGY (SEQ ID NO:3)/ GAGAGVGY (SEQ ID NO:4) sequence that assembles into semicrystalline domains, and amorphous regions that contain negatively charged, hydrophobic and aromatic residues[112]. The negatively charged amino acids, namely glutamic (Glu, 0.6 mol %) and aspartic acid (Asp, 0.5 mol %) found in these amorphous regions can be conjugated with primary amines of new functional groups through carbodiimide coupling[40]. Here we targeted the carboxylic acid side groups of these Asp and Glu residues to increase the total phenol content of silk heavy chain by 20% from 5.3 mol % (Tyr) to 6.4 mol % by conjugation of tyramine residues (FIG. 1A). The SF-TA was crosslinked with unmodified SF-TA at various ratios to determine its influence on gelation kinetics, shear mechanical properties, β-sheet content, morphology and enzymatic degradation of composite hydrogels. Aqueous SF-TA solution was used in bathless printing of hydrogel patterns using a coaxial needle without an inner needle by mixing pre-hydrogel solutions with HRP or $H_2O_2$ before extrusion (FIGS. 8A-8D), which has been recently reported by others for 3D bioprinting of tyramine-substituted gelatin hydrogels with a core-shell structure[113]. The novelty of our approach includes homogenous printing of aqueous silk bioinks with low concentration and viscosity through HRP-mediated crosslinking using a pre-defined $H_2O_2$ concentration that can be employed for printing of cell-laden silk hydrogel constructs. SF-TA solution was also used for fabrication of silk hydrogel microbeads using a coaxial needle for co-flow of the aqueous SF-TA+HRP stream with a $H_2O_2$-dispersed paraffin oil stream. Unlike the previous methods reported for fabrication of physically crosslinked silk microspheres, our strategy allows for fabrication of covalently crosslinked silk microgels at low silk concentration without the use of methanol or polyalcohols in the dispersed or continuous phases.

The next step was to encapsulate human mesenchymal stem cells in composite hydrogels with different SF-TA weight ratios with or without in situ conjugated cyclic RGD peptides to assess the bioactivity of composite hydrogels. It is possible to in situ conjugate linear peptides with a tyrosine residue into hydrogels during RP-mediated crosslinking[114-116], but this strategy has not been employed before for conjugation of any peptides in silk hydrogels or for conjugation of cyclic peptides in any hydrogel matrices. Here SF/SF-TA composite pre-hydrogel solutions were supplemented with cyclo(RGDyK) peptides and crosslinked via $HRP/H_2O_2$ reaction for in situ conjugation of cyclic peptides into cell-encapsulating hydrogel matrices (FIG. 1B). By modulation of SF/SF-TA weight ratios and cyclic RGD concentration, it was aimed to fabricate composite hydrogels with tunable gelation kinetics and bioactivity for encapsulation and culture of hMSCs.

For the present study, 60 minute-boiled (MB) silk fibroin (with a densiometric peak at ~50 kDa[117]) was used for tyramine substitution. The findings indicate that SF-TA significantly enhances gelation kinetics and shear mechanical properties and delays enzymatic crosslinking of the composite hydrogels, while in situ conjugation of cyclo (RGDyK) improves cell-matrix interactions. The SF/SF-TA/ cyclo(RGDyK) composite hydrogel formulations offer biocompatible alternatives for ionically crosslinked alginate or enzymatically crosslinked phenol-substituted gelatin or polysaccharides that display no self-assembly behavior for the culture and encapsulation of mammalian cells in tissue engineering and regenerative medicine applications.

Materials—All chemicals were purchased from Sigma-Aldrich and used as received without further purification unless otherwise specified. Cocoons from *Bombyx mori* silkworm were obtained from Tajima Shoji Co (Yokohama, Japan). Custom-synthesized Cyclo(RGDyK) peptides were purchased from Genescript Biotech Corp. (Piscataway NJ). $^1H$ NMR spectra were recorded with a Bruker Avance 500 NMR Spectrometer using $D_2O$ as the solvent. UV-Vis absorbance or fluorescence emissions were measured using a SpectraMax M2 multi-mode microplate reader (Molecular Devices, Sunnyvale, CA). Tyrosine, tyramine, dityrosine, tyrosine-tyramine and dityramine content of the hydrogels was analyzed using an Agilent 1200 series LC in tandem with an Agilent 6410 triplequadruple MS/MS (Agilent Technologies, Santa Clara, CA). Shear mechanical properties of hydrogels were characterized using an ARES-LS2 rheometer (TA Instruments, New Castle, DE). Infrared spectra were measured on solids in ambient atmosphere with a JASCO FTIR 6200 spectrometer (JASCO, Tokyo, Japan) with a MIRacle™ attenuated total reflection (ATR) with germanium crystal. Cell imaging was carried out using BZ-X700 Fluorescence Microscope (Keyence Corp., Itasca, IL) or TCS SP8 microscope from Leica Microsystems (Wetzlar, Germany).

Preparation of aqueous silk solutions—Aqueous silk solutions were prepared as described before[22]. Briefly, *B. mori* cocoons were degummed to remove sericin protein by boiling 5 g of cut cocoons in 2 L of 0.02 M sodium carbonate solution for 60 min and rinsing three times in deionized (DI) water. Degummed fibers were dried overnight and solubilized in 9.3 M lithium bromide solution at a concentration of 20% (w/v) for 4 h at 60° C. The solution was then dialyzed against distilled water using regenerated cellulose dialysis tubing (3.5 kD MWCO, Spectrum Labs Inc, Rancho Dominguez, CA). Dialysis water was changed 6 times over 3 days and the resulting solution was centrifuged 2 times at 9,000 rpm at 4° C. for 20 min to remove insoluble particles. The concentration of silk solution was determined by weighing a known volume of sample before and after drying overnight at 60° C.

Figure 2:
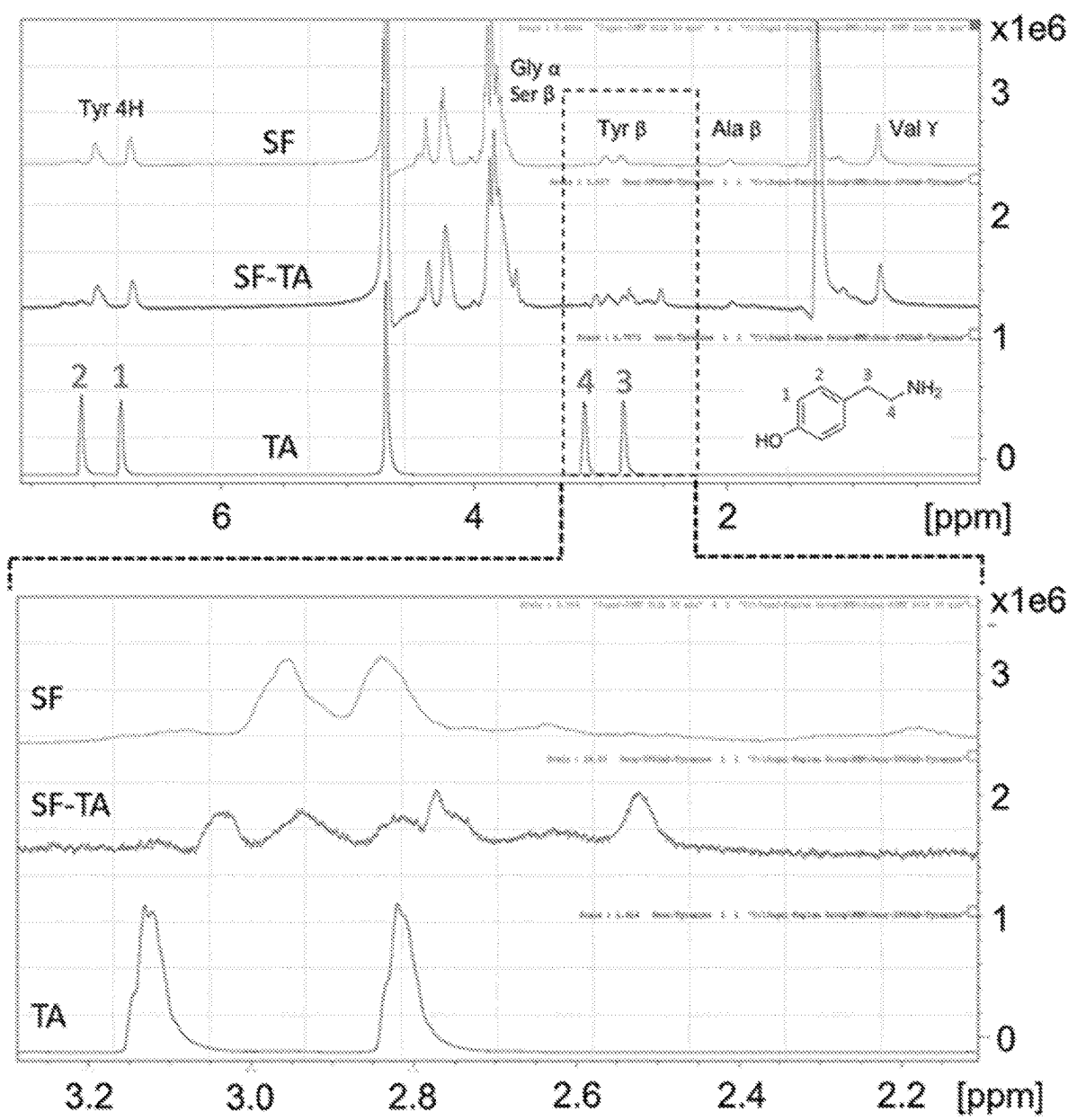
FIG. 2 shows $^1$HNMR spectra of silk fibroin (SF), tyramine-substituted silk fibroin (SF-TA) and tyramine hydrochloride (TA).

Synthesis and characterization of tyramine-substituted SF (SF-TA)—SF-TA derivative was synthesized via carbodiimide-mediated reaction. Briefly, 2% (w/v) SF solutions was prepared in 0.05 M 2-(N-morpholino)ethanesulfonic acid (MES) buffer (pH 6.0) and reacted with tyramine hydrochloride (500 mg per 1 g protein) in the presence of 1-ethyl-3-(-3-dimethylaminopropyl) carbodiimide hydrochloride (EDC) (Thermo Fisher Scientific, Rockford, IL) (184 mg per 1 g protein) and N-hydroxysuccinimide (NHS) (57 mg per 1 g protein) under stirring at room temperature for 18 h. Solution was dialyzed against distilled water using 3.5 MWCO tubing with 6 changes over 3 days. SF-TA was kept as a solution at 4° C. for up to a month. To confirm the presence of tyramine groups on silk after carbodiimide coupling, 15 mg/mL SF and SF-TA solutions were lyophilized and then redissolved in deuterated water ($D_2O$). SF and SF-TA solutions were analyzed with an NMR spectrometer. Alkyl proton peaks of tyramine were observed on SF-TA spectrum next to Tyr β proton peaks between 2.4-3.2 ppm (FIG. 2).

Gelation and rheological properties of SF/SF-TA composite hydrogels—To prepare SF/SF-TA hydrogels, aqueous SF was mixed with SF-TA solution at a final protein concentration of 50 mg/mL or 30 mg/mL in 40 mM hydroxyethyl) piperazine-1-ethanesulfonic acid (HEPES) buffer (pH 7.4) or 0.5× Dulbecco's Modified Eagle Medium (DMEM) High glucose with final SF-TA ratio ranging between 0-100%

(Table 1). Crosslinking kinetics of hydrogels was monitored at 37° C. by measuring fluorescence emission using a microplate reader. Gelation of 150 µL solutions was initiated with 10 U/mL HRP (type VI) and 0.01 or 0.005 wt. % $H_2O_2$ in a black 96-well plate and fluorescence emission at 415 nm after excitation at 315 nm was monitored for 4500 s. Results are reported after normalizing to a blank measurement taken before $H_2O_2$ was added (n=5).

TABLE 1

Concentrations of each component in 5% and 3% SF/SF-TA hydrogels. Samples are denoted by the weight ratio of SF-TA to total polymer concentration.

| Sample | SF Concentration (mg/ml) | SF-TA Concentration (mg/ml) |
|---|---|---|
| 5% hydrogels | | |
| SF only | 50 | 0 |
| 10% | 45 | 5 |
| 20% | 40 | 10 |
| 30% | 35 | 15 |
| 50% | 25 | 25 |
| 3% hydrogels | | |
| SF only | 30 | 0 |
| 10% | 27 | 3 |
| 30% | 21 | 9 |
| 50% | 15 | 15 |
| SF-TA only | 0 | 30 |

The sol-gel transition of SF/SF-TA composite hydrogels occurred upon mixing with HRP and $H_2O_2$. Hybrid hydrogels were opaque, the degree of which increased with increasing SF-TA content (FIG. 3A). Gelation speed (FIG. 3B-i) and fluorescent intensity (FIG. 3B-ii) of 5% SF/SF-TA hydrogels crosslinked in 40 mM HEPES increased with increasing SF-TA content, indicating an increase in crosslinking density. For 3% SF/SF-TA hydrogels crosslinked in 0.5×DMEM, however, no significant change was observed in fluorescence intensity (FIG. 3C-ii) even though gelation speed increased significantly (FIG. 3C-i).

Figure 4:
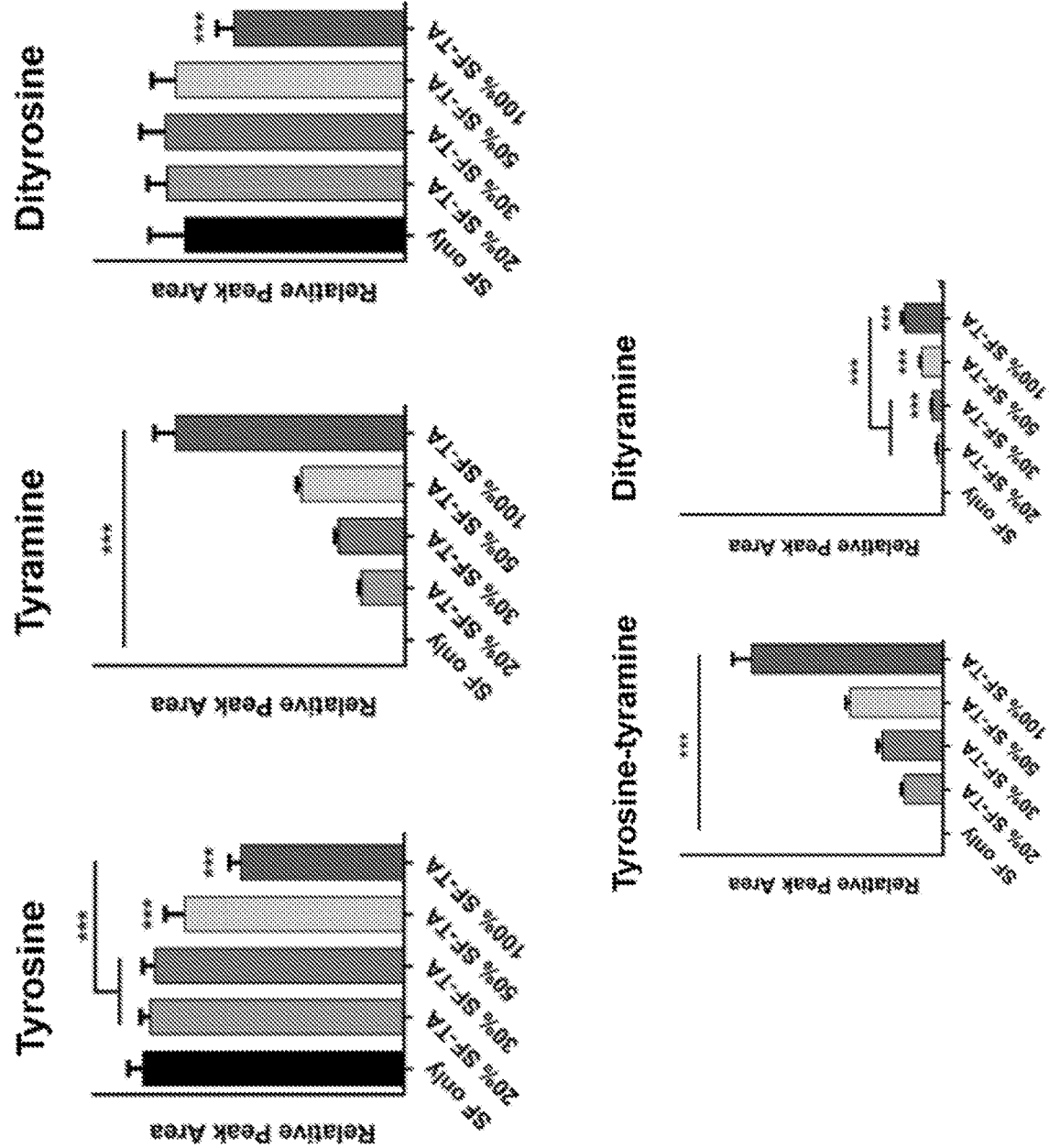
FIG. 4 shows relative peak areas of unreacted tyrosine or tyramine residues and covalent dityrosine, tyrosine-tyramine and dityramine crosslinks in 3% SF/SF-TA hydrogels crosslinked in 0.5×DMEM buffer using 0.01% $H_2O_2$ (n=3, *p<0.05, p<0.01 and *p<0.001, asterisks above the bars represent significance compared to SF only hydrogels).

Unreacted tyrosine and tyramine residues as well as dityrosine, tyrosine-tyramine and dityramine crosslinks were analyzed using a LC-MS/MS operated in positive electrospray ionization mode. 3% SF-TA hydrogels were hydrolyzed in 6N HCl for 4 hours at 60° C. Hydrolyzed samples were dehydrated and then reconstituted in 75% v/v LCMS grade acetonitrile in water to obtain a 400 µg/mL solution. 20 microliter samples were injected into a hydrophobic interaction liquid chromatography column at 40° C. and a rate of 1.0 µL/min. Column was first equilibrated at 95:5 acetonitrile (0.1% v/v formic acid) to water (0.1% v/v formic acid) and after 1 minute the mobile phase was adjusted to 5:95 acetonitrile to water over 5 minutes, held at high water for 2 minutes, and then returned to high acetonitrile. Nitrogen gas was operated at a flow rate of 11 L/min and set to 300° C. Fragment ions for each analyte of interest were identified using a product scan, and the collision energy for each ion was optimized to yield the maximum product. This information was integrated into a multiple reaction monitoring (MRM) program in the Agilent Mass Hunter software. The peak areas of dityrosine bonds and unreacted tyrosines decreased while those of tyrosine-tyramine and dityramine crosslinks increased with increasing SF-TA weight ratio (FIG. 4), suggesting covalent crosslinking of SF and SF-TA chains.

Figure 5A:
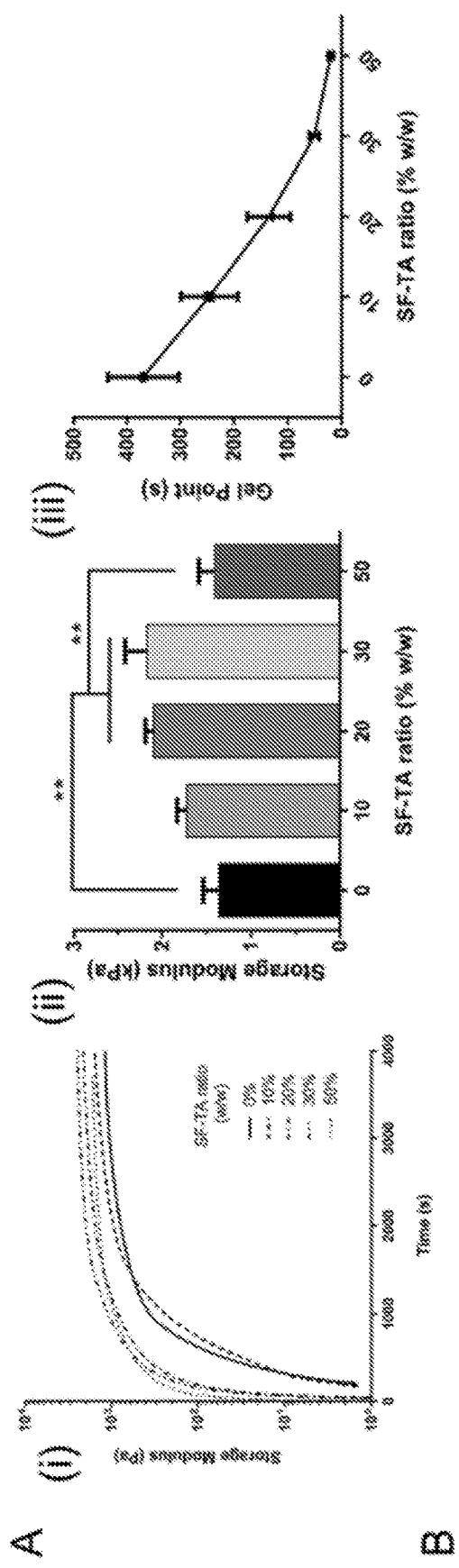
FIGS. 5A-5B show rheological properties of SF/SF-TA composite hydrogels.
Figure 5B:
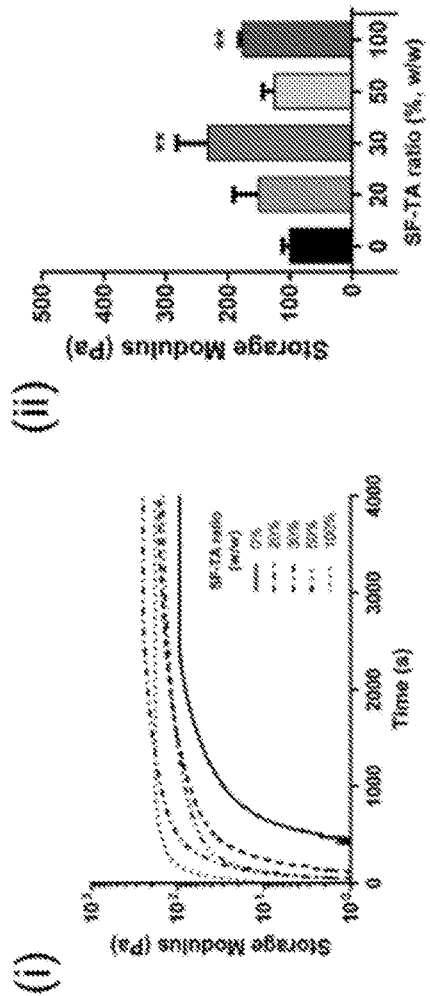
Figure 6A:
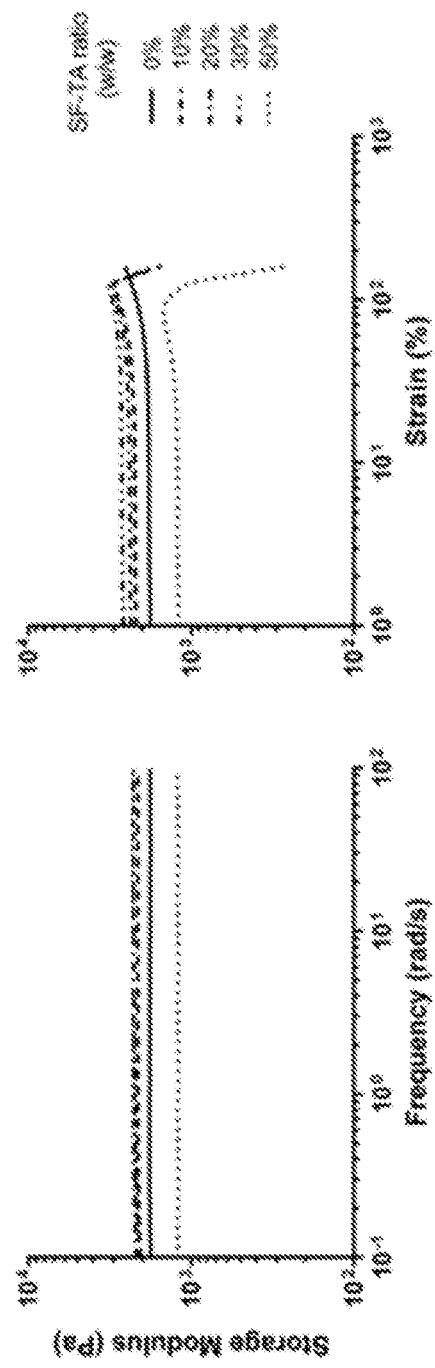
FIGS. 6A-6B show frequency and strain sweeps of (FIG. 6A) 5% and (FIG. 6B) 3% SF/SF-TA hydrogels crosslinked using 0.01 wt % $H_2O_2$ in 40 mM HEPES or 0.5×DMEM, respectively.
Figure 6B:
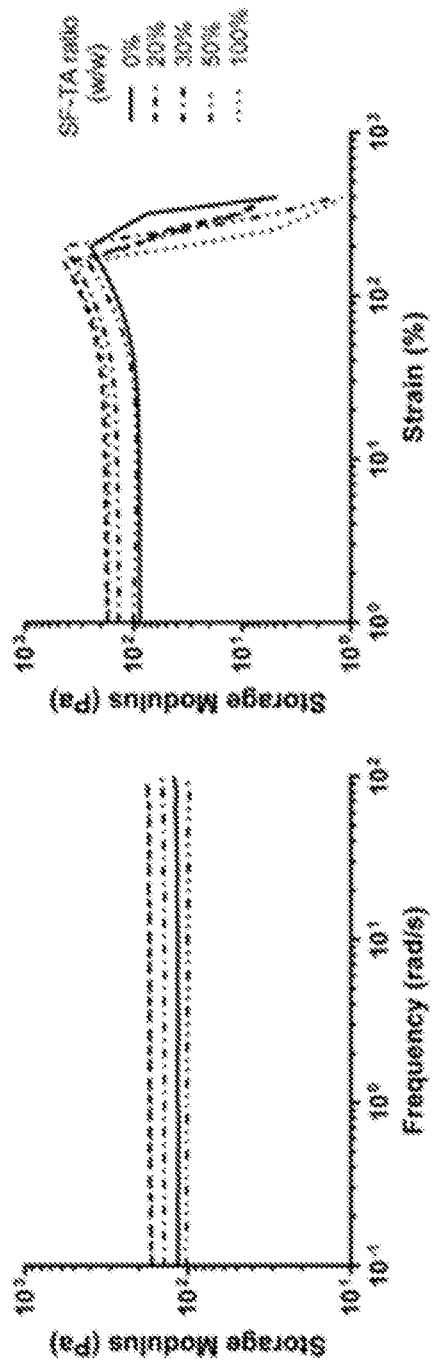

Rheological properties of the hydrogels were measured at 37° C. using a rheometer with a 25 mm stainless steel upper cone and temperature controlled Peltier bottom plate. A 420 µL aliquot of pre-hydrogel solutions with 10 U/mL HRP was loaded onto the Peltier and the cone was lowered to 47 µm. To initiate gelation, 4.2 µL of 1% or 0.5% $H_2O_2$ was injected into the gap during a 10 s precycle at a steady shear rate of 100/s. The gap was sealed with mineral oil to prevent evaporation during analysis. A dynamic time sweep was performed at 1 Hz with a 1% applied strain for 4,000 s to determine gelation kinetics and storage moduli. Dynamic frequency sweeps (0.1-100 rad/s at 1% strain) and strain sweeps (0.1%- to failure, at 1 Hz) were conducted to analyze elastic behavior of resulting hydrogels (n=3). Rheological properties were measured in the linear viscoelastic region, where the storage modulus was independent of the applied strain. Increasing SF-TA content increased gelation speed (FIG. 5A-i, B-i) and the shear storage moduli (FIG. 5A-ii, B-ii) up to a certain level, and gradually reduced the gel point (G"/G'<0.05) (FIG. 5A-iii). All gels tested regardless of SF-TA content, protein concentration or crosslinking media were frequency independent and withstood at least 100% shear strain (FIG. 6). Cyclic RGD peptides included in 3% SF/30% SF-TA hydrogels were expected to be conjugated to silk chains during crosslinking (FIG. 7A). Including cyclo(RGDyK) into the pre-hydrogel solution reduced gelation speed (FIG. 7B), lowered the storage modulus (FIG. 7C) and increased the gel point (FIG. 7D) compared to no peptide control at both 0.01 and 0.005 wt % $H_2O_2$.

Printability of SF-TA hydrogels and droplet-based microfluidic microgel fabrication—For the printing of the enzymatically crosslinked SF-TA hydrogels, 3% w/v solution was prepared in 0.5×DMEM high glucose colorless media and divided into 2 tubes. They were supplemented with either 20 U/mL HRP or 0.02 wt. % $H_2O_2$ (FIG. 8A) and loaded into separate 10 mL syringes connected to a custom-built 22 gauge steel needle with 2 inlets (Rame-Heart) (FIG. 8B). The 2-inlet needle was designed so that it can be used on commercial bioprinters as well (FIG. 8C). Syringes filled with SF-TA solutions were positioned on a syringe pump and connected to the needle with Masterflex silicone tubing with an inner diameter of 0.8 mm using female and male luer adapters (Cole-Parmer, IL USA). Flow rate was set to 0.5 mL/min and random patterns were manually printed on a plastic petri dish. Rapid gelation and an increase in opacity were observed upon mixing of two solutions during extrusion (FIG. 8D).

Figures 9A, 9B:
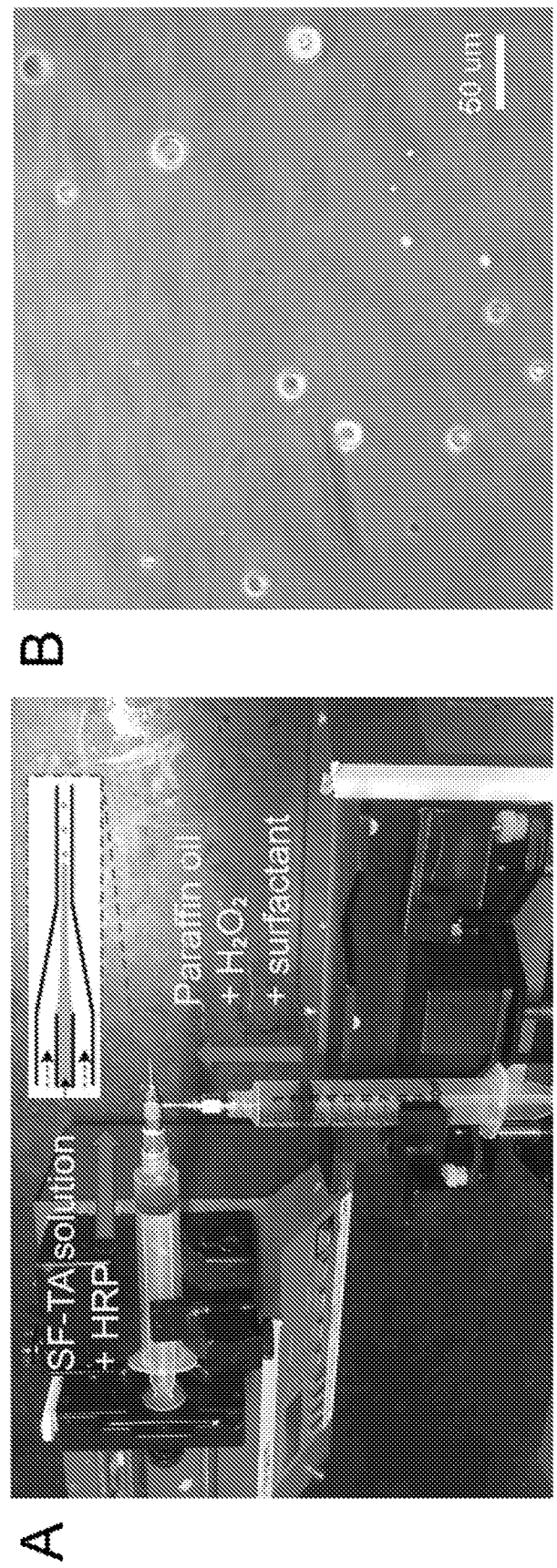
FIGS. 9A-9B show fabrication of SF-TA hydrogel microbeads using the co-flow microfluidics approach.
Figure 10:
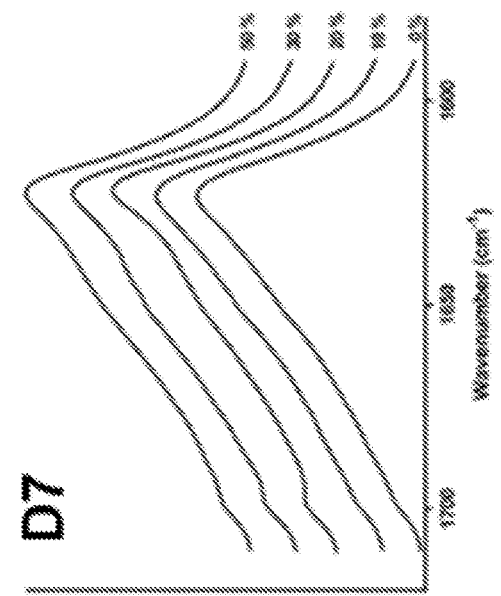
FIG. 10 shows ATR-FTIR absorbance spectra and β-sheet content of 5% SF/SF-TA hydrogels crosslinked in 40 mM HEPES and incubated in DPBS at 37° C. for 4 weeks (n=3, *p<0.05, p<0.01 and *p<0.001).
Figure 10:
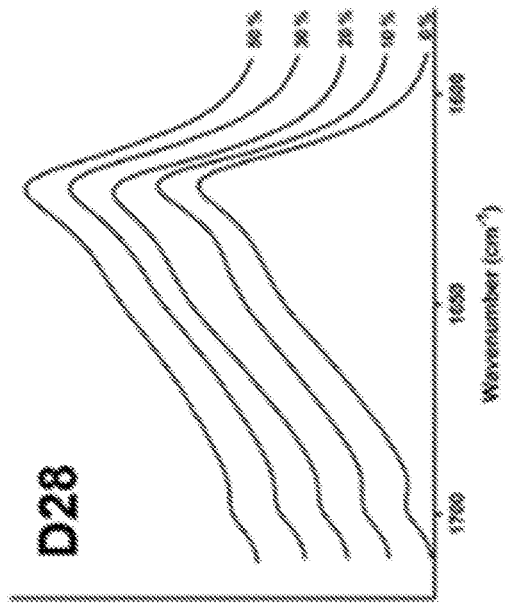
Figure 10:
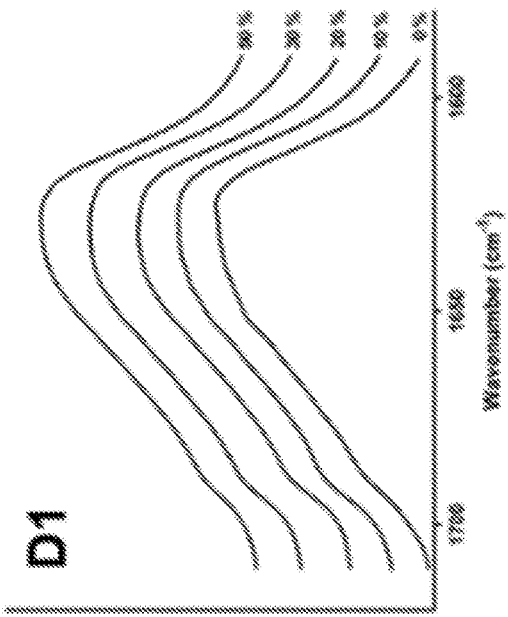
Figure 10:
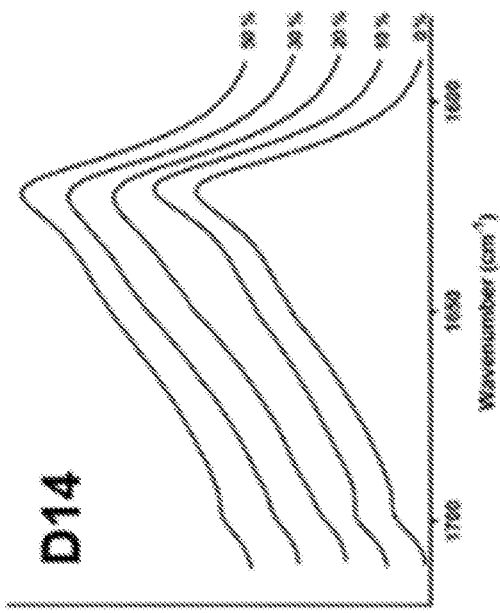
Figure 10:
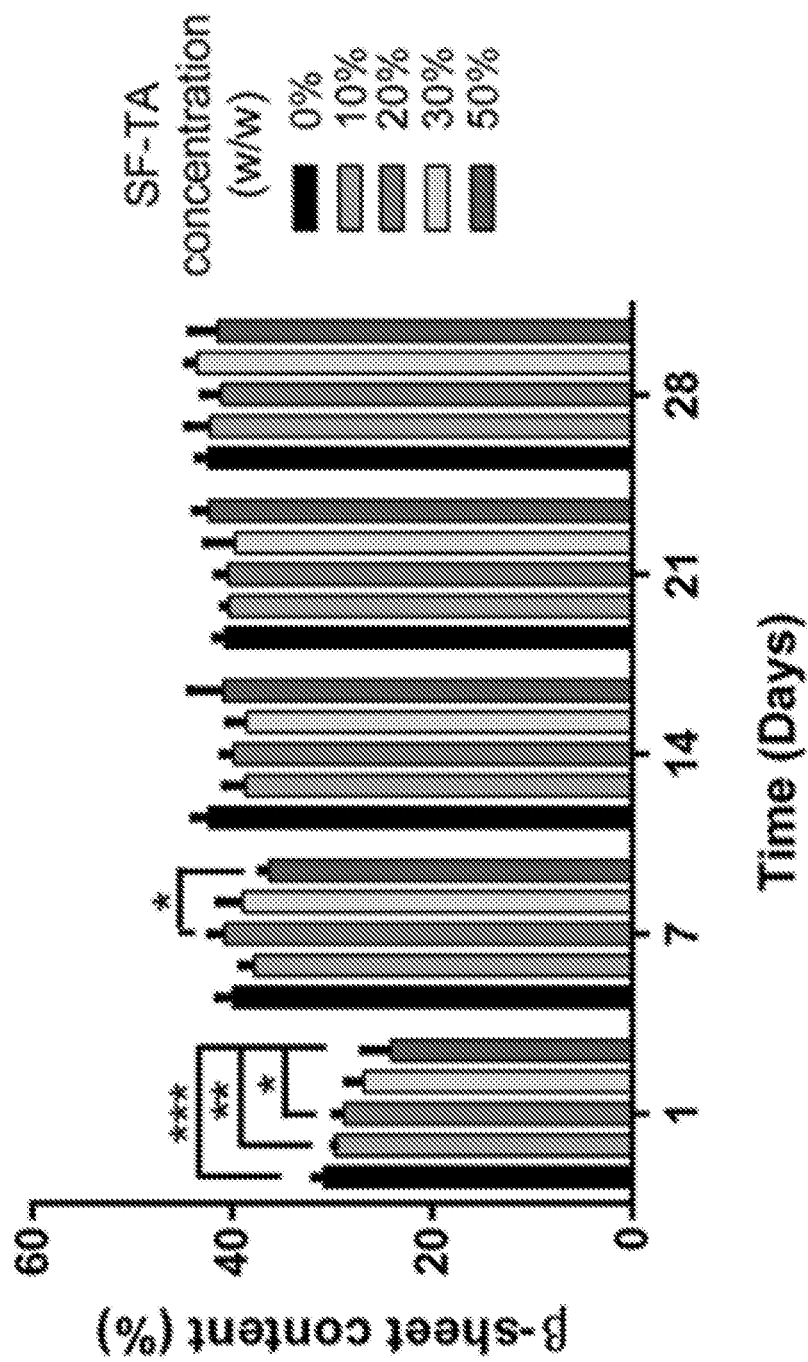

Enzymatically crosslinked silk microgels were fabricated via microfluidic approach using the co-flow geometry. To prepare a $H_2O_2$-dispersed oil phase, 100 µL of 30 wt % $H_2O_2$ was added into 1 mL of paraffin oil and the aqueous phase was dispersed within the oil phase by mixing with a tissue homogenizer for 10 min. The mixture was then centrifuged at 3000 rpm for 10 min, the oil phase was collected and supplemented with 3% v/v Span80 as the surfactant. 3% w/v SF-TA solution was prepared in 0.5× DMEM colorless media and supplemented with 10 U/mL HRP. Both the pre-hydrogel solution and the oil phase were sterile filtered using a 0.22 µm filter to remove any micron scale impurities and loaded into separate 10 mL syringes. Syringes were positioned on separate syringe pumps and connected to a co-axial needle with a 28 gauge inner and 14 gauge outer needle. The inner and outer needles were directly connected to the syringes filled with the SF-TA solution and the oil phase, respectively (FIG. 9A). Aqueous and oil flow rates were optimized at 0.05 and 2 mL/min to obtain silk microgels with diameters ranging between 10-30 µm (FIG. 9B).

β-sheet content of composite hydrogels—Secondary structure of the hydrogels was analyzed using an ATR-FTIR. Hydrogel discs (4 mm diameter, ~2-3 mm height) were prepared by gelling 200 µL aliquots of solutions in polydimethylsiloxane (PDMS) molds incubated in 1 mL DPBS for 1, 7, 14, 21 and 28 days (n=3). After washing in deuterium oxide three times for 30 min each, measurements were conducted by averaging 32 scans with a resolution of 4 cm$^{-1}$ between 600 and 4000 cm$^{-1}$. After deconvolution, β-sheet content was calculated as the ratio of areas of peak absorbances at 1616-1621, 1622-1627, 1628-1637 and 1697-1703 cm$^{-1}$ to total area between 1580-1720 cm$^{-1}$. β-sheet content of 5% hydrogels at day 1 was in the range of 20-30% and decreased with increasing SF-TA. At day 7, SF only and SF/SF-TA hydrogels reached a p-sheet content of approximately 40% and remained approximately the same over 4 weeks (FIG. 10).

Figures 11A, 11B:
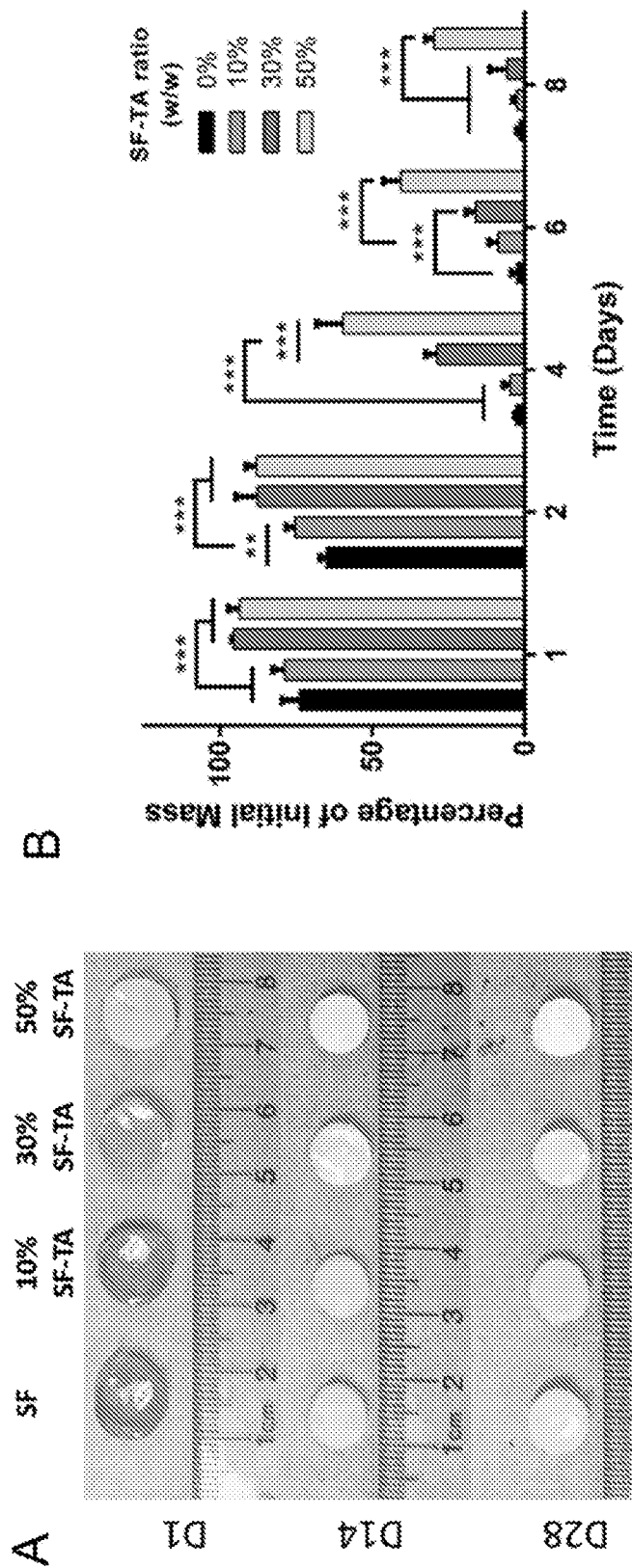
FIGS. 11A-11B show morphology and enzymatic degradation of SF/SF-TA hydrogels.

Hydrogel morphology and in vitro enzymatic degradation—The 5% and 3% composite hydrogels prepared in 40 mM HEPES and 0.5×DMEM, respectively, were incubated in PBS at 37° C. and their morphologies were monitored over 4 weeks. All hydrogel discs shrank significantly and became opaquer by day 14 compared to day 1 (FIG. 11A) due to the increase in β-sheet content. Hydrogel discs prepared from 200 µL solutions in PDMS molds were incubated in DPBS at room temperature for 4 h. Hydrogels were then transferred into 300 µL of 0.001 U/mL of protease (type XIV from *Streptomyces griseus*) dissolved in DPBS and incubated for 1, 2, 4, 6 or 8 days. The enzyme solution was changed every 2 days. After removal of the enzyme solution, hydrogels were washed in Ultrapure™ distilled water (ThermoFisher Scientific, Waltham, MA) over night at room temperature, lyophilized and weighed. Results are reported as the mass fraction of the initial weight at day 0 (n=4). Increasing SF-TA delayed the degradation of 5% hydrogels (FIG. 11B). Less than 5% of the initial mass of SF only hydrogels remained at day 4 while those of SF/50% SF-TA was around 60% and 30% their original weights at days 4 and 8, respectively. Considering that the delivery vehicles should sustain desired release kinetics while the tissue engineering scaffolds should gradually degrade in the body while guiding cell growth and deposition of new ECM until the original tissue architecture is restored [122], tunable degradation of SF/SF-TA hydrogels is an important advantage.

In vitro human mesenchymal stem cell response—Human bone marrow mesenchymal stem cells (hMSCs) (ATCC, Manassas, VA) were cultured in DMEM High glucose supplemented with 10% fetal bovine serum (FBS), 1% Penicillin-Streptomycin (Life Technologies, Carlsbad, CA), 1% non-essential amino acids and 1 ng/mL of fibroblast growth factor-2 (FGF-2) (Invitrogen, Carlsbad, CA). 5% SF/20% SF-TA solutions supplemented with 0, 0.1, 0.25, 0.5 or 1 mM cyclo(RGDyK) were prepared in 40 mM HEPES and 300 µL aliquots with 10 U/mL HRP and 0.01% $H_2O_2$, and allowed to cure in 24-well plates for 1 h at 37° C. in an incubator. Cells at passage 3 were seeded onto tissue culture plastic (TCP) controls and hydrogel surfaces at a density of 4,000 cells/cm$^2$ in 1 mL of growth medium without FBS. At day 1, seeding media was replaced with regular growth media with FBS and it was changed every 3 days. Many cells on no RGD controls displayed a round morphology at day 1 while those on the hydrogels supplemented with cyclic RGD flattened and spread well (FIG. 12A). Area of cell spreading increased and reached a plateau with increasing cyclo(RGDyK) concentration (FIG. 12B). The fold change in metabolic activity over 4 weeks increased significantly with increasing cyclo(RGDyK) concentration, reaching a maximum of 3.92-fold on hydrogels with 1 mM cyclo (RGyK) (FIG. 12C). At day 14, cells on all hydrogels spread well and reached confluency at day 28 (FIG. 12D).

Figures 13A, 13B:
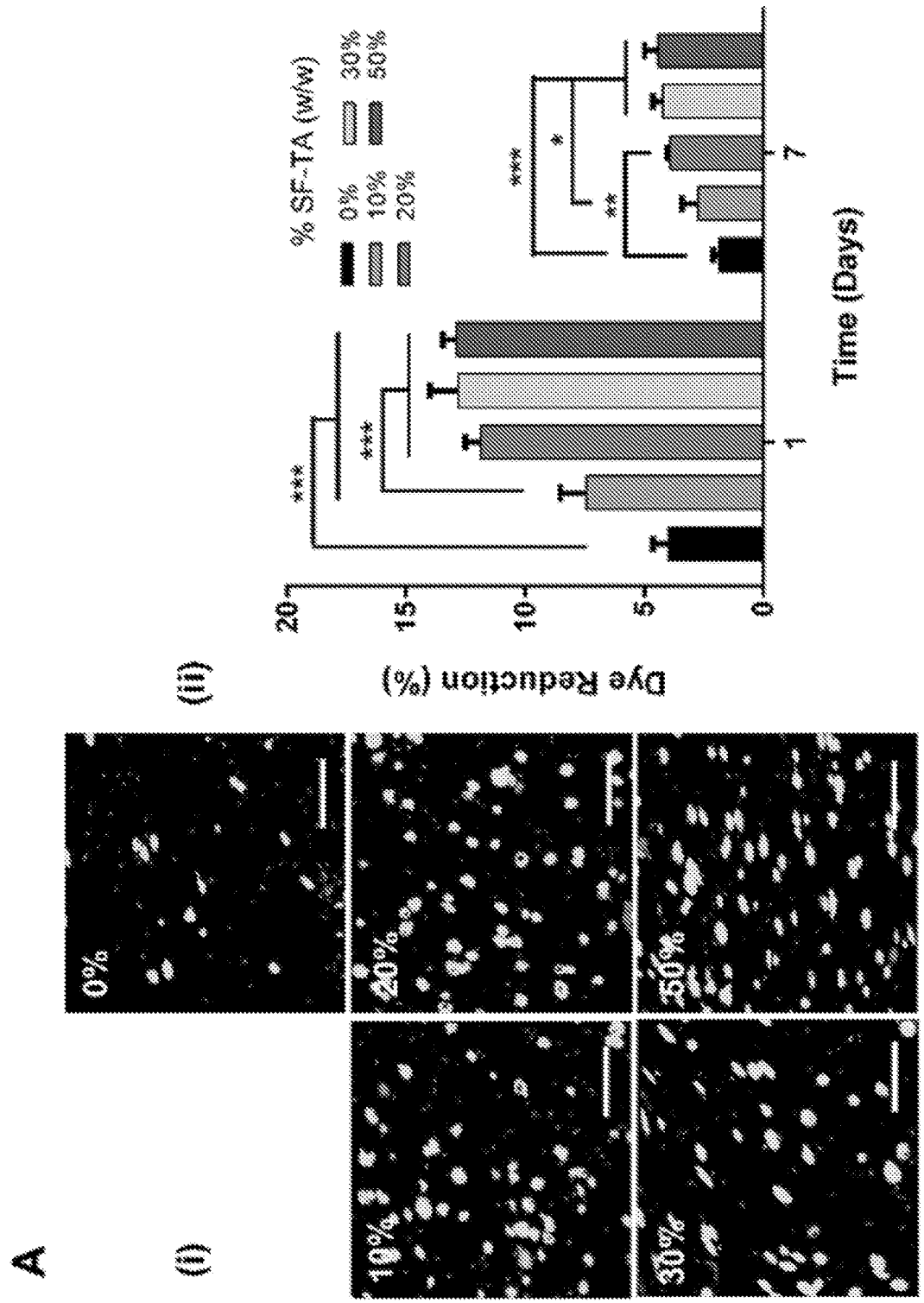
FIGS. 13A-13B show viability and morphology of hMSCs encapsulated in silk hydrogels.
Figures 13A, 13B:
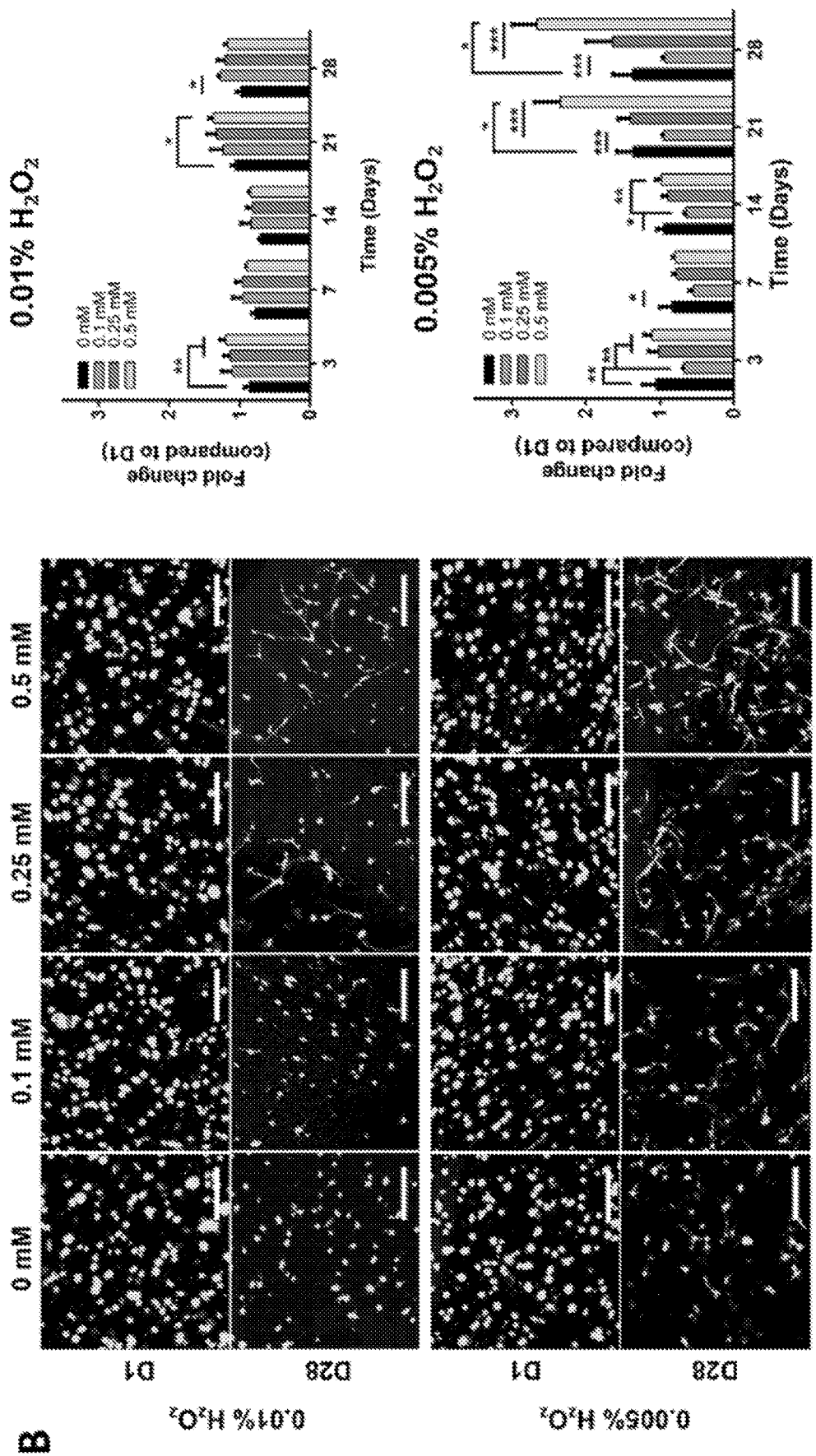

For cell encapsulation, 300 uL pre-hydrogel solutions with 10 U/mL HRP were prepared in 40 mM HEPES or 0.5×DMEM and mixed with cells at passage 3 at a concentration of 2×10$^5$ cells/mL. Cell-laden precursor solutions with 0.01 or 0.005 wt. % $H_2O_2$ were then allowed to cure in 24 well-plates for 1 h at 37° C. in an incubator. The wells were then flooded with 1 mL of culture media and it was changed every 3 days. Viability and morphology of hMSCs cultured on and encapsulated in hydrogels were characterized using a fluorescence or confocal microscope, respectively, after Live/Dead staining. Day 1 fluorescence images of the cells cultured on the hydrogels were analyzed using ImageJ (1.48v, NIH, USA) to quantify cell spread areas (n>200). Metabolic activity of the cells was determined at days 1, 3, 7, 14, 21 and 28 by alamarBlue viability assay (Invitrogen, Carlsbad, CA) according to the manufacturer's directions. Results are reported as the fold change in % dye reduction at day 3, 7, 14, 21 and 28 after normalization to initial measurement at day 1 (n=4). Fewer dead cells were observed (FIG. 13A-i) and % dye reduction at day 1 increased significantly in 5% w/v hydrogels crosslinked in HEPES buffer with increasing SF-TA content from 0 to 50% w/w, but metabolic activity decreased in all groups at day 7 (FIG. 13A-ii). In 3% hydrogels crosslinked in 0.5×DMEM, fold change in metabolic activity increased significantly and cells exhibited elongated or branched morphologies with cytoplasmic extensions upon an increase in cyclo (RGDyK) concentration at low (0.005% wt. %) $H_2O_2$ (FIG. 13B).

In Vivo Response to SF-TA Hydrogel Discs:

Hydrogel discs of 8 mm diameter and 4 mm height were fabricated in autoclaved PDMS molds using 200 µL sterile filtered aliquots of 3% w/v SF-TA in 0.5×DMEM High glucose using 10 U/mL HRP and 0.01 wt % $H_2O_2$. Preformed gels were implanted subcutaneously into 12-week old female Friend Virus B NIH Jackson (FVB/NJ) mice (The Jackson Laboratory, Bar Harbor, ME) under the protocol approved by the Tufts Institutional Animal Care and Use Committee (M2019-121) (n=3, 2 hydrogel discs per animal). The mice were anesthetized initially at 3% isoflurane and maintained at 2% for the duration of the surgery. Prior to making the incision, the area was shaved, sterilized using disinfectant and ethanol swabs and a subcutaneous injection of the sustained-release buprenorphine (0.5 mg/mL) analgesic was administered at a dose of 1 mg/kg.

Figure 14A:
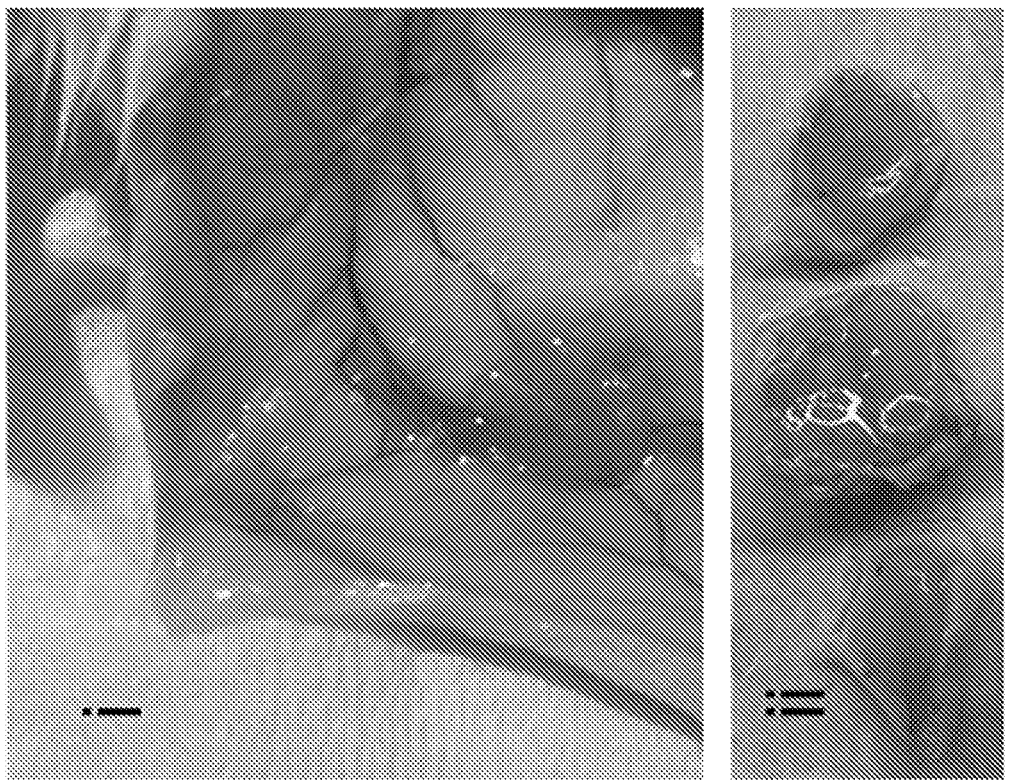
FIGS. 14A-14B show in vivo animal tests.
Figure 14B:
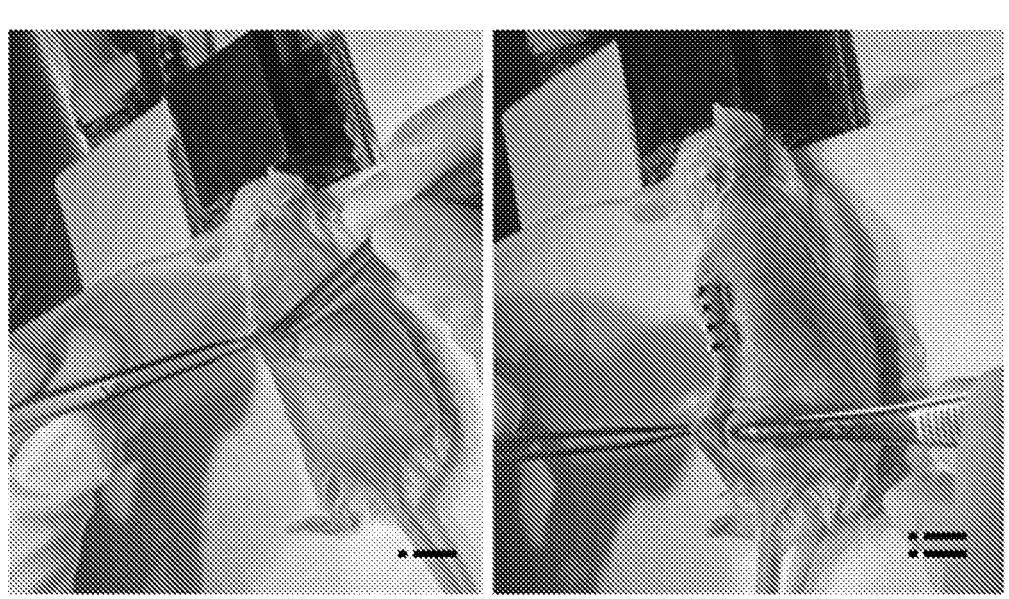

Two independent incisions (6-10 mm) were made on the back of each mouse to create a subcutaneous pocket using scissors and a blunt probe and the preformed SF-TA hydrogel discs were inserted into the pockets (FIG. 14A, panel i). Incisions were closed with 1 or 2 stainless steel wound clips (FIG. 14A, panel ii). The mice were monitored daily and euthanized by C02 asphyxiation after 3 or 28 days and the hydrogel discs together with the surrounding cutaneous tissues were collected (FIG. 14B). After resection and fixation in 4% paraformaldehyde for 48 hours, the hydrogel discs submerged in increasing concentrations of sucrose (15-30% w/v) in PBS for 48 hours, flash frozen using dry ice in optimal cutting temperature (OCT) media and stored at −80° C. freezer until cryo-sectioning. The samples were sliced into 15 µm cross-sections using a cryostat and collected on Fisherbrand tissue path superfrost plus gold slides (Fisher Scientific, Hampton, NH). The samples were stained with hematoxylin and eosin (H&E) and imaged using fluorescence microscope.

No adverse effects from the implants were observed over 3 or 28 days. H&E staining showed formation of a thin inflammatory capsule surrounding the gels over 3 days indicating a typical foreign body response, which became more apparent at 28 days (FIG. 15). The hydrogel discs displayed a relatively bioinert behavior since no excessive inflammation or cell infiltration into the gels were observed over 4 weeks. Hydrogel discs from day 3 were larger in size and were broken into several pieces during the processing, while the samples from day 28 were significantly smaller and intact, pointing out the stiffening of the gels over time in in vivo conditions similar to the observations made in vitro.

In Situ Crosslinking of SF-TA Hydrogel Nanolayers on Mammalian Cell Membrane for Nanoencapsulation of Individual Cells:

L929 murine fibroblast cells from mouse subcutaneous connective tissues (ATCC, Manassas, VA) were used for nonspecific deposition of SF-TA hydrogel nanolayers on the cells by priming the cell surface with tyramine-substituted gelatin (G-TA) (FIG. 16A). Gelatin type A from porcine skin (Sigma Aldrich) was substituted with tyramine residues on carboxylic acid groups of aspartic and glutamic acid side chains in a similar fashion with the synthesis of SF-TA. Briefly, 2% (w/v) gelatin solution was prepared in 0.05 MES buffer (pH 6.0) and reacted with tyramine hydrochloride (Sigma-Aldrich, St. Louis, MO) (500 mg per 1 g protein) in the presence of EDC (184 mg per 1 g protein) and NHS (57 mg per 1 g protein) under stirring at RT for 18 h. The solution was dialyzed against distilled water at 37° C. using 3.5 MWCO tubing with 6 changes over 3 days, lyophilized and stored at −20° C.

G-TA and SF or SF-TA were labeled on primary amine residues with rhodamine B isothiocyanate (RBITC) or fluorescein isothiocyanate (FITC), respectively, for the visualization of deposition on mammalian cells. RBITC or FITC were dissolved in dimethyl sulfoxide (DMSO) at a concentration of 10 mg·mL$^{-1}$, diluted 4 times with distilled water and 100 µL of it was added dropwise to 10 mL of 5 mg·mL$^{-1}$ G-TA or SF-TA solution in 0.1 M carbonate buffer (pH 9.0). The mixture was stirred for 1 h at RT and then dialyzed in 3.5 kDa cutoff dialysis membranes against distilled water for 3 days with six water changes. RBITC-conjugated G-TA was lyophilized and stored at −20° C. FITC-conjugated SF-TA solution was concentrated to ~2% w/v by water evaporation from the dialysis tubing in a fume hood over 2 days.

The surface of L929 fibroblasts were primed with G-TA or RBITC-labeled G-TA by incubating the cells in 5 mg·mL$^{-1}$ solution in HD50 (40 mM HEPES, 5% w/v dextrose, 50 mM NaCl, pH 7.4) buffer at a density of $10^6$ cells·mL$^{-1}$ for 1 min at RT under gentle shaking. After washing with blank HD50 buffer, cells were resuspended in 5 mg·mL$^{-1}$ SF-TA or FITC-labeled SF-TA in HD50 buffer supplemented with 10 U·mL$^{-1}$ HRP and 0.1 mM $H_2O_2$ and incubated for 20 min at RT under gentle shaking. Cells were washed with HD50 buffer and seeded on TCP for live/dead staining or confocal imaging.

For cell specific nanoencapsulation in SF-TA hydrogel layers, hMSCs were labeled on surface with HRP-conjugated antibodies to localize covalent crosslinking to the cell surface (FIG. 16B). MSC specific surface markers cluster of differentiation (CD) 90 (CD90, a.k.a. Thymocyte differentiation antigen 1 (Thy-1)) and 44 (CD44, a.k.a. homing cell adhesion molecule (HCAM)) [120] were targeted for labeling. hMSCs at passage 3 were suspended in 400 µL of DMEM High Glucose supplemented with 0.3 µg·mL$^{-1}$ anti-human CD90 (AF-9, ab23894) and 0.3 µg·mL$^{-1}$ anti-human CD44 (MEM-263, ab9524) IgG1 mouse monoclonal antibodies at a density of 5×10$^5$ cells·mL$^{-1}$ and incubated at RT for 30 min. After washing twice with 1×PBS, cells were incubated in 400 µL DMEM High Glucose supplemented with 0.55 µg·mL$^{-1}$ of HRP-conjugated polyclonal goat anti-mouse IgG1 heavy chain (ab97240) (Abcam, Cambridge, MA) at RT for 30 min. After washing twice with 1×PBS, cells were resuspended in 1% w/v SF-TA or FITC-labeled SF-TA solution in 0.5×DMEM High Glucose supplemented with 0.1 mM $H_2O_2$ and incubated for 20 min at RT. Cells were washed with 1×PBS and seeded on TCP for live/dead staining or confocal imaging.

Confocal imaging showed that the surface of L929 fibroblasts incubated with fluorescently-labeled G-TA solution was positive for RBITC signal (FIG. 17A, panel i), conforming the deposition of G-TA layers on plasma membrane likely through electrostatic interactions between the positively charged gelatin type A and the negatively charged cell surface [118, 119]. Cells incubated with FITC-labeled SF-TA, however, did not display any fluorescence signal due to the low positively charged amino acid content of SF. G-TA primed cells that were incubated in FITC-labeled SF-TA solution supplemented with HRP and $H_2O_2$ showed high FITC signal while no $H_2O_2$ or no G-TA control groups were negative for the fluorescence signal (FIG. 17A, panel i), suggesting that HRP-mediated covalent crosslinking between the surface-deposited G-TA and the free SF-TA chains in the solution allowed for the deposition of SF-TA hydrogel layers on cell surface rather than the nonspecific binding of SF-TA chains to cell surface or G-TA layers. The encapsulation protocol did not show significant cytotoxicity as the live/dead imaging of the cells revealed a viability above 90% (FIG. 17A, panel ii).

Figures 17A, 17B:
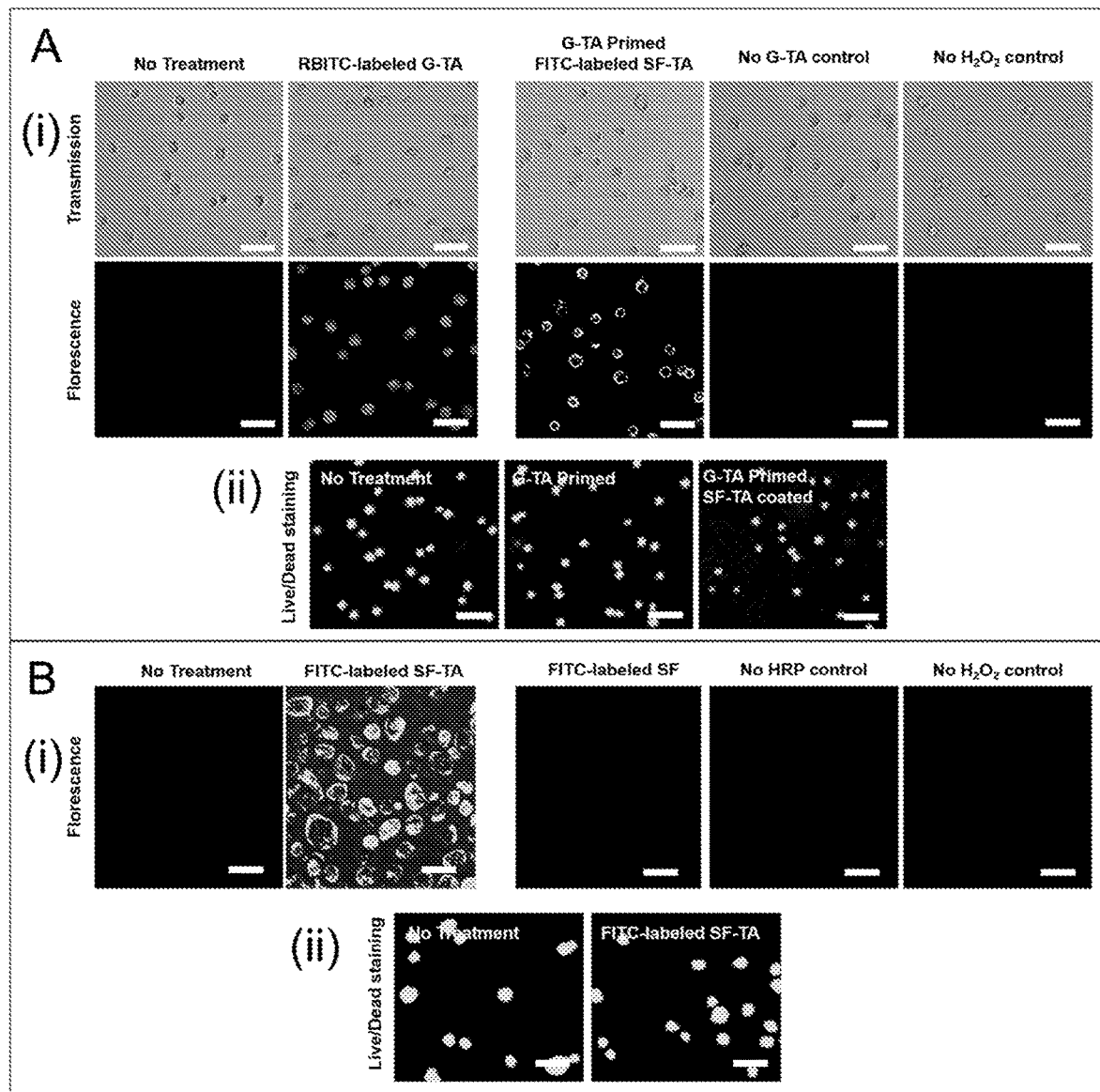
FIGS. 17A-17B show confocal and fluorescence micrographs of L929 fibroblasts and hMSCs after nanocoating with enzymatically crosslinked SF-TA and live/dead staining.

The data from cell-specific crosslinking of SF-TA that was localized on the surface of hMSCs through antibody-mediated immobilization of HRP on the cells revealed that tyramine modification of SF enabled single cell nanoencapsulation within silk-based hydrogel layers. hMSCs labeled with HRP-conjugated antibodies and incubated in FITC-labeled SF-TA solution supplemented with $H_2O_2$ were positive for fluorescence signal while the ones incubated in FITC-labeled SF were negative, indicating that significantly faster crosslinking of SF-TA in physiological buffer (0.5× DMEM) compared to SF allowed for gelation on cell surface (FIG. 17B, panel i). Moreover, the lack of FITC signal in the no HRP and no $H_2O_2$ controls showed that the deposition of SF-TA on the cells was not nonspecific and was in situ crosslinking mediated by cell surface-immobilized HRP. No significant difference was observed in cell viability between the untreated and nanocoated cells (FIG. 17B, panel ii), suggesting that the nanoencapsulation process was cytocompatible.

REFERENCES

[1] Yildirimer, L., & Seifalian, A. M. (2014). Three-dimensional biomaterial degradation—Material choice, design and extrinsic factor considerations. Biotechnology advances, 32(5), 984-999.

[2] Nicodemus, G. D., & Bryant, S. J. (2008). Cell encapsulation in biodegradable hydrogels for tissue engineering applications. Tissue Engineering Part B: Reviews, 14(2), 149-165.

[3] Tasoglu, S., & Demirci, U. (2013). Bioprinting for stem cell research. Trends in biotechnology, 31(1), 10-19.

[4] Zhang, Y. S., Yue, K., Aleman, J., Mollazadeh-Moghaddam, K., Bakht, S. M., Yang, J., Dokmeci, M. R. (2017). 3D bioprinting for tissue and organ fabrication. Annals of biomedical engineering, 45(1), 148-163.

[5] Gudapati, H., Dey, M., & Ozbolat, I. (2016). A comprehensive review on droplet-based bioprinting: past, present and future. Biomaterials, 102, 20-42.

[6] Wan, J. (2012). Microfluidic-based synthesis of hydrogel particles for cell microencapsulation and cell-based drug delivery. Polymers, 4(2), 1084-1108.

[7] Kang, A., Park, J., Ju, J., Jeong, G. S., & Lee, S. H. (2014). Cell encapsulation via microtechnologies. Biomaterials, 35(9), 2651-2663.

[8] Rossow, T., Lienemann, P. S., & Mooney, D. J. (2017). Cell microencapsulation by droplet microfluidic templating. Macromolecular Chemistry and Physics, 218(2), 1600380.

[9] Hasturk, O., & Kaplan, D. L. (2019). Cell armor for protection against environmental stress: Advances, challenges and applications in micro- and nanoencapsulation of mammalian cells. Acta biomaterialia, 95, 3-31.

[10] Chimene, D., Lennox, K. K., Kaunas, R. R., & Gaharwar, A. K. (2016). Advanced bioinks for 3D printing: a materials science perspective. Annals of biomedical engineering, 44(6), 2090-2102.

[11] McGill, M., Coburn, J. M., Partlow, B. P., Mu, X., & Kaplan, D. L. (2017). Molecular and macro-scale analysis of enzyme-crosslinked silk hydrogels for rational biomaterial design. Acta biomaterialia, 63, 76-84.

[12] Kim, K. S., Park, S. J., Yang, J. A., Jeon, J. H., Bhang, S. H., Kim, B. S., & Hahn, S. K. (2011). Injectable hyaluronic acid-tyramine hydrogels for the treatment of rheumatoid arthritis. Acta biomaterialia, 7(2), 666-674.

[13] Toh, W. S., Lim, T. C., Kurisawa, M., & Spector, M. (2012). Modulation of mesenchymal stem cell chondrogenesis in atunable hyaluronic acid hydrogel microenvironment. Biomaterials, 33(15), 3835-3845.

[14] C. H. Goh, P. W. S. Heng, L. W. Chan, Alginates as a useful natural polymer for microencapsulation and therapeutic applications. Carbohyd. Polym. 88(1) (2012) 1-12.

[15] B. Rzany, Overview on injectable fillers: Efficacy and safety, in: M. De Maio, B. Rzany (Eds.), Injectable fillers in aesthetic medicine, Springer, Berlin, 2014, pp. 1-16.

[16] E. Axpe, M. Oyen, Applications of alginate-based bioinks in 3D bioprinting. Int. J. Mol. Sci. 17(12) (2016) 1976.

[17] H. J. Kong, D. Kaigler, K. Kim, D. J. Mooney, Controlling rigidity and degradation of alginate hydrogels via molecular weight distribution. Biomacromolecules 5(5) (2004) 1720-1727.

[18] [D. Shahriari, J. Koffler, D. A. Lynam, M. H. Tuszynski, J. S. Sakamoto, Characterizing the degradation of alginate hydrogel for use in multilumen scaffolds for spinal cord repair. J. Biomed. Mater. Res. A, 104(3) (2016) 611-619.

[19] Vepari, C., & Kaplan, D. L. (2007). Silk as a biomaterial. Progress in polymer science, 32(8-9), 991-1007.

[20] S. Kapoor, S. C. Kundu, Silk protein-based hydrogels: promising advanced materials for biomedical applications. Acta Biomater. 31 (2016) 17-32.

[21] Aeschbach, R., Amadb, R., & Neukom, H. (1976). Formation of dityrosine cross-links in proteins by oxidation of tyrosine residues. Biochimica et biophysica acta, 439(2), 292-301.

[22] Partlow, B. P., Hanna, C. W., Rnjak-Kovacina, J., Moreau, J. E., Applegate, M. B., Burke, K. A., Kaplan, D. L. (2014). Highly tunable elastomeric silk biomaterials. Advanced functional materials, 24(29), 4615-4624.

[23] Bradner, S. A., Partlow, B. P., Cebe, P., Omenetto, F. G., & Kaplan, D. L. (2017). Fabrication of elastomeric silk fibers. Biopolymers, 107(9), e23030.

[24] Tabatabai, A. P., Partlow, B. P., Raia, N. R., Kaplan, D. L., & Blair, D. L. (2018). Silk Molecular Weight Influences the Kinetics of Enzymatically Cross-linked Silk Hydrogel Formation. Langmuir, 34(50), 15383-15387.

[25] Sundarakrishnan, A., Acero, E. H., Coburn, J., Chwalek, K., Partlow, B., & Kaplan, D. L. (2016). Phenol red-silk tyrosine cross-linked hydrogels. Acta biomaterialia, 42, 102-113.

[26] Chung, B. G., Lee, K. H., Khademhosseini, A., & Lee, S. H. (2012). Microfluidic fabrication of microengineered hydrogels and their application in tissue engineering. Lab on a Chip, 12(1), 45-59.

[27] Kirchmajer, D. M., & Gorkin Iii, R. (2015). An overview of the suitability of hydrogel-forming polymers for extrusion-based 3D-printing. Journal of Materials Chemistry B, 3(20), 4105-4117.

[28] Chimene, D., Lennox, K. K., Kaunas, R. R., & Gaharwar, A. K. (2016). Advanced bioinks for 3D printing: a materials science perspective. Annals of biomedical engineering, 44(6), 2090-2102.

[29] Wang, Y., Kim, H. J., Vunjak-Novakovic, G., & Kaplan, D. L. (2006). Stem cell-based tissue engineering with silk biomaterials. Biomaterials, 27(36), 6064-6082.

[30] Wang, X., Kluge, J. A., Leisk, G. G., & Kaplan, D. L. (2008). Sonication-induced gelation of silk fibroin for cell encapsulation. Biomaterials, 29(8), 1054-1064.

[31] Sakai, S., Hirose, K., Taguchi, K., Ogushi, Y., & Kawakami, K. (2009). An injectable, in situ enzymatically gellable, gelatin derivative for drug delivery and tissue engineering. Biomaterials, 30(20), 3371-3377.

[32] Lee, F., Chung, J. E., & Kurisawa, M. (2008). An injectable enzymatically crosslinked hyaluronic acid-tyramine hydrogel system with independent tuning of mechanical strength and gelation rate. Soft Matter, 4(4), 880-887.

[33] Lee, F., Bae, K. H., & Kurisawa, M. (2015). Injectable hydrogel systems crosslinked by horseradish peroxidase. Biomedical Materials, 11(1), 014101.

[34] McGill, M., Coburn, J. M., Partlow, B. P., Mu, X., & Kaplan, D. L. (2017). Molecular and macro-scale analysis of enzyme-crosslinked silk hydrogels for rational biomaterial design. Acta biomaterialia, 63, 76-84.

[35] Shulha, H., Foo, C. W. P., Kaplan, D. L., & Tsukruk, V. V. (2006). Unfolding the multi-length scale domain structure of silk fibroin protein. Polymer, 47(16), 5821-5830.

[36] Hersel, U., Dahmen, C., & Kessler, H. (2003). RGD modified polymers: biomaterials for stimulated cell adhesion and beyond. Biomaterials, 24(24), 4385-4415.

[37] Kantlehner, M., Schaffner, P., Finsinger, D., Meyer, J., Jonczyk, A., Diefenbach, B., Kessler, H. (2000). Surface coating with cyclic RGD peptides stimulates osteoblast adhesion and proliferation as well as bone formation. Chembiochem, 1(2), 107-114.

[38] Zhu, J., Tang, C., Kottke-Marchant, K., & Marchant, R. E. (2009). Design and synthesis of biomimetic hydrogel scaffolds with controlled organization of cyclic RGD peptides. Bioconjugate chemistry, 20(2), 333-339.

[39] Kaufmann, D., Fiedler, A., Junger, A., Auernheimer, J., Kessler, H., & Weberskirch, R. (2008). Chemical Conjugation of Linear and Cyclic RGD Moieties to a Recombinant Elastin-Mimetic Polypeptide-A Versatile Approach towards Bioactive Protein Hydrogels. Macromolecular bioscience, 8(6), 577-588.

[40] Murphy, A. R., & Kaplan, D. L. (2009). Biomedical applications of chemically-modified silk fibroin. Journal of materials chemistry, 19(36), 6443-6450.

[41] Serban, M. A., & Kaplan, D. L. (2010). pH-Sensitive ionomeric particles obtained via chemical conjugation of silk with poly (amino acid) s. Biomacromolecules, 11(12), 3406-3412.

[42] Vepari, C. P., & Kaplan, D. L. (2006). Covalently immobilized enzyme gradients within three-dimensional porous scaffolds. Biotechnology and bioengineering, 93(6), 1130-1137.

[43] Saxena, U., & Goswami, P. (2010). Silk mat as biomatrix for the immobilization of cholesterol oxidase. Applied biochemistry and biotechnology, 162(4), 1122-1131.

[44] Wang, X., & Kaplan, D. L. (2011). Functionalization of silk fibroin with NeutrAvidin and biotin. Macromolecular bioscience, 11(1), 100-110.

[45] Sofia, S., McCarthy, M. B., Gronowicz, G., & Kaplan, D. L. (2001). Functionalized silk-based biomaterials for bone formation. Journal of Biomedical Materials Research: An Official Journal of The Society for Biomaterials and The Japanese Society for Biomaterials, 54(1), 139-148.

[46] Vidal, G., Blanchi, T., Mieszawska, A. J., Calabrese, R., Rossi, C., Vigneron, P., . . . & Egles, C. (2013). Enhanced cellular adhesion on titanium by silk functionalized with titanium binding and RGD peptides. Acta biomaterialia, 9(1), 4935-4943.

[47] Bai, L., Zhu, L., Min, S., Liu, L., Cai, Y., & Yao, J. (2008). Surface modification and properties of *Bombyx mori* silk fibroin films by antimicrobial peptide. Applied Surface Science, 254(10), 2988-2995.

[48] Gil, E. S., Mandal, B. B., Park, S. H., Marchant, J. K., Omenetto, F. G., & Kaplan, D. L. (2010). Helicoidal multi-lamellar features of RGD-functionalized silk biomaterials for corneal tissue engineering. Biomaterials, 31(34), 8953-8963.

[49] Kardestuncer, T., McCarthy, M. B., Karageorgiou, V., Kaplan, D., & Gronowicz, G. (2006). RGD-tethered silk substrate stimulates the differentiation of human tendon cells. Clinical Orthopaedics and Related Research (1976-2007), 448, 234-239.

[50] Wang, H., Ma, L., Yang, S., Shao, Z., Meng, C., Duan, D., & Li, Y. (2009). Effect of RGD-modified silk material on the adhesion and proliferation of bone marrow-derived mesenchymal stem cells. Journal of Huazhong University of Science and Technology [Medical Sciences], 29(1), 80-83.

[51] Chen, J., Altman, G. H., Karageorgiou, V., Horan, R., Collette, A., Volloch, V., Kaplan, D. L. (2003). Human bone marrow stromal cell and ligament fibroblast responses on RGD-modified silk fibers. Journal of Biomedical Materials Research Part A: An Official Journal of The Society for Biomaterials, The Japanese Society for Biomaterials, and The Australian Society for Biomaterials and the Korean Society for Biomaterials, 67(2), 559-570.

[52] Kim, J. W., Ki, C. S., Park, Y. H., Kim, H. J., & Um, I. C. (2010). Effect of RGDS and KRSR peptides immobilized on silk fibroin nanofibrous mats for cell adhesion and proliferation. Macromolecular research, 18(5), 442-448.

[53] Ye, C., Shchepelina, O., Calabrese, R., Drachuk, I., Kaplan, D. L., & Tsukruk, V. V. (2011). Robust and responsive silk ionomer microcapsules. Biomacromolecules, 12(12), 4319-4325.

[54] Ye, C., Drachuk, I., Calabrese, R., Dai, H., Kaplan, D. L., & Tsukruk, V. V. (2012). Permeability and micromechanical properties of silk ionomer microcapsules. Langmuir, 28(33), 12235-12244.

[55] Calabrese, R., & Kaplan, D. L. (2012). Silk ionomers for encapsulation and differentiation of human MSCs. Biomaterials, 33(30), 7375-7385.

[56] Kim, S., Geryak, R. D., Zhang, S., Ma, R., Calabrese, R., Kaplan, D. L., & Tsukruk, V. V. (2017). Interfacial Shear Strength and Adhesive Behavior of Silk Ionomer Surfaces. Biomacromolecules, 18(9), 2876-2886.

[57] Drachuk, I., Calabrese, R., Harbaugh, S., Kelley-Loughnane, N., Kaplan, D. L., Stone, M., & Tsukruk, V. V. (2015). Silk macromolecules with amino acid-poly (ethylene glycol) grafts for controlling layer-by-layer encapsulation and aggregation of recombinant bacterial cells. ACS nano, 9(2), 1219-1235.

[58] A. A. Amini, L. S. Nair, Enzymatically cross-linked injectable gelatin gel as osteoblast delivery vehicle. J. Bioact. Compat. Polym. 27(4) (2012) 342-355.

[59] Z. Peng, Y. She, L. Chen, Synthesis of poly (glutamic acid)-tyramine hydrogel by enzyme-mediated gelation for controlled release of proteins. J. Biomater. Sci. Polym. Ed. 26(2) (2015) 111-127.

[60] M. Kurisawa, J. E. Chung, Y. Y. Yang, S. J. Gao, H. Uyama, Injectable biodegradable hydrogels composed of hyaluronic acid-tyramine conjugates for drug delivery and tissue engineering. ChemComm (34) (2005) 4312-4314.

[61] K. S. Kim, S. J. Park, J. A. Yang, J. H. Jeon, S. H. Bhang, B. S. Kim, S. K. Hahn, Injectable hyaluronic acid-tyramine hydrogels for the treatment of rheumatoid arthritis. Acta Biomater. 7(2) (2011) 666-674.

[62] W. S. Toh, T. C. Lim, M. Kurisawa, M. Spector, Modulation of mesenchymal stem cell chondrogenesis in a tunable hyaluronic acid hydrogel microenvironment. Biomaterials, 33(15) (2012) 3835-3845.

[63] K. Xu, K. Narayanan, F. Lee, K. H. Bae, S. Gao, M. Kurisawa, Enzyme-mediated hyaluronic acid-tyramine hydrogels for the propagation of human embryonic stem cells in 3D. Acta Biomater. 24 (2015) 159-171.

[64] R. Jin, C. Hiemstra, Z. Zhong, J. Feijen, Enzyme-mediated fast in situ formation of hydrogels from dextran-tyramine conjugates. Biomaterials, 28(18) (2007) 2791-2800.

[65] L. S. M. Teixeira, S. Bijl, V. V. Pully, C. Otto, R. Jin, J. Feijen, C. A. van Blitterswijk, P. J. Dijkstra, M. Karperien, Self-attaching and cell-attracting in-situ forming dextran-tyramine conjugates hydrogels for arthroscopic cartilage repair. Biomaterials, 33(11) (2012) 3164-3174.

[66] H. Wei, J. Xie, X. Jiang, T. Ye, A. Chang, W. Wu, Synthesis and Characterization of Dextran-Tyramine-Based H2O2-Sensitive Microgels. Macromolecules, 47(17) (2014) 6067-6076.

[67] S. Sakai, K. Kawakami, Synthesis and characterization of both ionically and enzymatically cross-linkable alginate. Acta Biomater. 3(4) (2007) 495-501.

[68] S. Sakai, K. Hirose, K. Moriyama, K. Kawakami, Control of cellular adhesiveness in an alginate-based hydrogel by varying peroxidase and $H_2O_2$ concentrations during gelation. Acta Biomater. 6(4) (2010) 1446-1452.

[69] Y. K. Joung, S. S. You, K. M. Park, D. H. Go, K. D. Park, In situ forming, metal-adhesive heparin hydrogel

[70] S. Sakai, Y. Ogushi, K. Kawakami, Enzymatically crosslinked carboxymethylcellulose-tyramine conjugate hydrogel: cellular adhesiveness and feasibility for cell sheet technology. Acta Biomater, 5(2) (2009) 554-559.

[71] R. Jin, B. Lou, C. Lin, Tyrosinase-mediated in situ forming hydrogels from biodegradable chondroitin sulfate-tyramine conjugates. Polym. Int. 62(3) (2013) 353-361.

[72] K. S. Lim, Y. Ramaswamy, J. J. Roberts, M. H. Alves, L. A. Poole-Warren, P. J. Martens, Promoting cell survival and proliferation in degradable Poly (vinyl alcohol)-Tyramine Hydrogels. Macromol. Biosci. 15(10)(2015) 1423-1432.

[73] T. Kamperman, S. Henke, B. Zoetebier, N. Ruiterkamp, R. Wang, B. Pouran, H. Weinans, M. Karperien, J. Leijten, Nanoemulsion-induced enzymatic crosslinking of tyramine-functionalized polymer droplets. J. Mater. Chem. B, 5(25) (2017) 4835-4844.

[74] T. Yucel, P. Cebe, D. L. Kaplan, Vortex-induced injectable silk fibroin hydrogels. Biophys. J. 97(7) (2009) 2044-2050.

[75] X. Wang, J. A. Kluge, G. G. Leisk, D. L. Kaplan, Sonication-induced gelation of silk fibroin for cell encapsulation. Biomaterials, 29(8) (2008) 1054-1064.

[76] J. Y. Fang, J. P. Chen, Y. L. Leu, H. Wang, Characterization and evaluation of silk protein hydrogels for drug delivery, Chem. Pharm. Bull. 54 (2006) 156-162

[77] A. Motta, C. Migliaresi, F. Faccioni, P. Torricelli, M. Fini, R. Giardino, Fibroin hydrogels for biomedical applications: preparation, characterization and in vitro cell culture studies, J. Biomater. Sci. Polym. Ed. 15 (2004) 851-864.

[78] H. Zhao, S. Xiong, M. Li, Q. Zhang, G. Liu, Comparison of gelation time and polyalcohol effect on hydrogels from domestic and wild silk fibroins. Adv. Mater. Sci. Eng. 2012 (2012).

[79] Rodriguez, M. J., Brown, J., Giordano, J., Lin, S. J., Omenetto, F. G., & Kaplan, D. L. (2017). Silk based bioinks for soft tissue reconstruction using 3-dimensional (3D) printing with in vitro and in vivo assessments. Biomaterials, 117, 105-115.

[80] Jose, R. R., Brown, J. E., Polido, K. E., Omenetto, F. G., & Kaplan, D. L. (2015). Polyol-silk bioink formulations as two-part room-temperature curable materials for 3D printing. ACS Biomaterials Science & Engineering, 1(9), 780-788.

[81] Rodriguez, M. J., Dixon, T. A., Cohen, E., Huang, W., Omenetto, F. G., & Kaplan, D. L. (2018). 3D freeform printing of silk fibroin. Acta biomaterialia, 71, 379-387.

[82] Breslauer, D. N., Muller, S. J., & Lee, L. P. (2010). Generation of monodisperse silk microspheres prepared with microfluidics. Biomacromolecules, 11(3), 643-647.

[83] Mitropoulos, A. N., Perotto, G., Kim, S., Marelli, B., Kaplan, D. L., & Omenetto, F. G. (2014). Synthesis of silk fibroin micro- and submicron spheres using a co-flow capillary device. Advanced Materials, 26(7), 1105-1110.

[84] C. M. Hwang, S. Sant, M. Masaeli, N. N. Kachouie, B. Zamanian, S. H. Lee, A. Khademhosseini, Fabrication of three-dimensional porous cell-laden hydrogel for tissue engineering. Biofabrication 2(3) (2010) 035003.

[85] Chirila, T. V., Suzuki, S., & Papolla, C. (2017). A comparative investigation of *Bombyx mori* silk fibroin hydrogels generated by chemical and enzymatic crosslinking. Biotechnology and applied biochemistry, 64(6), 771-781.

[86] Kim, H. H., Kim, J. W., Choi, J., Park, Y. H., & Ki, C. S. (2018). Characterization of silk hydrogel formed with hydrolyzed silk fibroin-methacrylate via photopolymerization. Polymer, 153, 232-240.

[87] Kang, G. D., Lee, K. H., Ki, C. S., & Park, Y. H. (2004). Crosslinking reaction of phenolic side chains in silk fibroin by tyrosinase. Fibers and Polymers, 5(3), 234.

[88] Applegate, M. B., Partlow, B. P., Coburn, J., Marelli, B., Pirie, C., Pineda, R., Omenetto, F. G. (2016). Photocrosslinking of silk fibroin using riboflavin for ocular prostheses. Advanced Materials, 28(12), 2417-2420.

[89] J. Choi, M. McGill, N. R. Raia, O. Hasturk, D. L. Kaplan, Silk Hydrogels Crosslinked by the Fenton Reaction. Adv. Healthcare Mater. (2019) 1900644.

[90] Brown, J. E., Partlow, B. P., Berman, A. M., House, M. D., & Kaplan, D. L. (2016). Injectable silk-based biomaterials for cervical tissue augmentation. an in vitro study. American journal of obstetrics and gynecology, 214(1), 118-e1.

[91] Compaan, A. M., Christensen, K., & Huang, Y. (2016). Inkjet bioprinting of 3D silk fibroin cellular constructs using sacrificial alginate. ACS Biomaterials Science & Engineering, 3(8), 1519-1526.

[92] Stoppel, W. L., Gao, A. E., Greaney, A. M., Partlow, B. P., Bretherton, R. C., Kaplan, D. L., Black III, L. D. (2016). Elastic, silk-cardiac extracellular matrix hydrogels exhibit time-dependent stiffening that modulates cardiac fibroblast response. Journal of Biomedical Materials Research Part A, 104(12), 3058-3072.

[93] Ribeiro, V. P., da Silva Morais, A., Maia, F. R., Canadas, R. F., Costa, J. B., Oliveira, A. L., Reis, R. L. (2018). Combinatory approach for developing silk fibroin scaffolds for cartilage regeneration. Acta biomaterialia, 72, 167-181.

[94] Golding, A., Guay, J. A., Herrera-Rincon, C., Levin, M., & Kaplan, D. L. (2016). A tunable silk hydrogel device for studying limb regeneration in adult *Xenopus Laevis*. PloS one, 11(6), e0155618.

[95] Zhao, S., Chen, Y., Partlow, B. P., Golding, A. S., Tseng, P., Coburn, J., Kaplan, D. L. (2016). Bio-functionalized silk hydrogel microfluidic systems. Biomaterials, 93, 60-70.

[96] Melikov, R., Press, D. A., Kumar, B. G., Dogru, I. B., Sadeghi, S., Chirea, M., Nizamoglu, S. (2017). Silk-hydrogel lenses for light-emitting diodes. Scientific reports, 7(1), 7258.

[97] T. Sminia, F. Delemarre, E. M. Janse, Histological observations on the intestinal immune response towards horseradish peroxidase in rats. Immunology 50(1) (1983) 53.

[98] A. M. Gardner, F. H. Xu, C. Fady, F. J. Jacoby, D. C. Duffey, Y. Tu, A. Lichtenstein, Apoptotic vs. nonapoptotic cytotoxicity induced by hydrogen peroxide. Free Radic. Biol. Med. 22(1-2) (1997) 73-83.

[99] N. R. Raia, B. P. Partlow, M. McGill, E. P. Kimmerling, C. E. Ghezzi, D. L. Kaplan, Enzymatically crosslinked silk-hyaluronic acid hydrogels. Biomaterials 131 (2017) 58-67.

[100] Vidal, S. E. L., Tamamoto, K. A., Nguyen, H., Abbott, R. D., Cairns, D. M., & Kaplan, D. L. (2019). 3D biomaterial matrix to support long term, full thickness, immuno-competent human skin equivalents with nervous system components. Biomaterials, 198, 194-203.

[101] E. S. Gil, D. J. Frankowski, R. J. Spontak, S. M. Hudson, Swelling behavior and morphological evolution of mixed gelatin/silk fibroin hydrogels. Biomacromolecules 6(6) (2005) 3079-3087.

[102] S. Das, F. Pati, S. Chameettachal, S. Pahwa, A. R. Ray, S. Dhara, S. Ghosh, Enhanced redifferentiation of chondrocytes on microperiodic silk/gelatin scaffolds: toward tailor-made tissue engineering. Biomacromolecules 14(2) (2013) 311-321.

[103] J. C. Bragg, H. Kweon, Y. Jo, K. G. Lee, C. C. Lin, In situ formation of silk-gelatin hybrid hydrogels for affinity-based growth factor sequestration and release. RSC Advances 6(115) (2016) 114353-114360.

[104] W. Xiao, J. He, J. W. Nichol, L. Wang, C. B. Hutson, B. Wang, Y. Du, H. Fan, A. Khademhosseini, Synthesis and characterization of photocrosslinkable gelatin and silk fibroin interpenetrating polymer network hydrogels. Acta Biomater. 7(6) (2011) 2384-2393.

[105] W. Xiao, W. Liu, J. Sun, X. Dan, D. Wei, H. Fan, Ultrasonication and genipin cross-linking to prepare novel silk fibroin-gelatin composite hydrogel. J. Bioact. Compat. Polym. 27(4) (2012) 327-341.

[106] J. Liesivuori, A. H. Savolainen, Methanol and formic acid toxicity: biochemical mechanisms. Pharmacol. Toxicol. 69(3) (1991) 157-163.

[107] L. B. Feril Jr, T. Kondo, Q. L. Zhao, R. Ogawa, K. Tachibana, N. Kudo, S. Fujimoto, S. Nakamura, Enhancement of ultrasound-induced apoptosis and cell lysis by echo-contrast agents. Ultrasound Med. Biol. 29(2) (2003) 331-337.

[108] W. Sun, T. Incitti, C. Migliaresi, A. Quattrone, S. Casarosa, A. Motta, Genipin-crosslinked gelatin-silk fibroin hydrogels for modulating the behaviour of pluripotent cells. J. Tissue Eng. Regen. Med 10(10) (2016) 876-887.

[109] S. Das, F. Pati, Y. J., Choi, G. Rijal, J. H. Shim, S. W. Kim, A. R. Ray, D. Cho, S. Ghosh, Bioprintable, cell-laden silk fibroin-gelatin hydrogel supporting multilineage differentiation of stem cells for fabrication of three-dimensional tissue constructs. Acta Biomater. 11 (2015) 233-246.

[110] S. Chameettachal, S. Midha, S. Ghosh, Regulation of chondrogenesis and hypertrophy in silk fibroin-gelatin-based 3D bioprinted constructs. ACS Biomater. Sci. Eng. 2(9) (2016) 1450-1463.

[111] Sun, W., Incitti, T., Migliaresi, C., Quattrone, A., Casarosa, S., & Motta, A. (2017). Viability and neuronal differentiation of neural stem cells encapsulated in silk fibroin hydrogel functionalized with an IKVAV peptide. Journal of tissue engineering and regenerative medicine, 11(5), 1532-1541.

[112] Ma, M., Zhong, J., Li, W., Zhou, J., Yan, Z., Ding, J., & He, D. (2013). Comparison of four synthetic model peptides to understand the role of modular motifs in the self-assembly of silk fibroin. Soft Matter, 9(47), 11325-11333.

[113] Hong, S., Kim, J. S., Jung, B., Won, C., & Hwang, C. (2019). Coaxial bioprinting of cell-laden vascular constructs using a gelatin-tyramine bioink. Biomaterials science.

[114] K. M. Park, I. Jun, Y. K. Joung, H. Shin, K. D. Park, In situ hydrogelation and RGD conjugation of tyramine-conjugated 4-arm PPO-PEO block copolymer for injectable bio-mimetic scaffolds. Soft Matter 7(3) (2011) 986-992.

[115] L. S. Wang, F. Lee, J. Lim, C. Du, A. C. Wan, S. S. Lee, M. Kurisawa, Enzymatic conjugation of a bioactive peptide into an injectable hyaluronic acid-tyramine hydrogel system to promote the formation of functional vasculature. Acta Biomater. 10(6) (2014) 2539-2550.

[116] C. Loebel, S. E. Szczesny, B. D. Cosgrove, M. Alini, M. Zenobi-Wong, R. L. Mauck, D. Eglin, Cross-linking chemistry of tyramine-modified hyaluronan hydrogels alters mesenchymal stem cell early attachment and behavior. Biomacromolecules 18(3) (2017) 855-864.

[117] Wray, L. S., Hu, X., Gallego, J., Georgakoudi, I., Omenetto, F. G., Schmidt, D., & Kaplan, D. L. (2011). Effect of processing on silk-based biomaterials: Reproducibility and biocompatibility. Journal of Biomedical Materials Research Part B: Applied Biomaterials, 99(1), 89-101.

[118] Li, W., Guan, T., Zhang, X., Wang, Z., Wang, M., Zhong, W., Kong, J. (2015). The effect of layer-by-layer assembly coating on the proliferation and differentiation of neural stem cells. ACS applied materials & interfaces, 7(5), 3018-3029.

[119] Li, W., Zhang, G., Guan, T., Zhang, X., Khosrozadeh, A., Xing, M., & Kong, J. (2018). Manipulable Permeability of Nanogel Encapsulation on Cells Exerts Protective Effect against TNF-α-Induced Apoptosis. ACS Biomaterials Science & Engineering, 4(8), 2825-2835.

[120] Barberini, D. J., Freitas, N. P. P., Magnoni, M. S., Maia, L., Listoni, A. J., Heckler, M. C., Amorim, R. M. (2014). Equine mesenchymal stem cells from bone marrow, adipose tissue and umbilical cord: immunophenotypic characterization and differentiation potential. Stem cell research & therapy, 5(1), 25.

We claim:

1. A composition comprising tyramine-substituted silk fibroin, wherein a first phenol group of the tyramine-substituted silk fibroin is covalently crosslinked to a second phenol group of the tyramine-substituted silk fibroin.

2. The composition of claim 1, wherein the tyramine-substituted silk fibroin is selected from the group consisting of silkworm silk fibroin, spider silk fibroin, and recombinant silk fibroin.

3. The composition of claim 1, further comprising unsubstituted silk fibroin; wherein at least one tyrosine of the unsubstituted silk fibroin is covalently crosslinked to at least one phenol group of the tyramine-substituted silk fibroin.

4. The composition of claim 3, wherein a ratio of unsubstituted silk fibroin to tyramine-substituted fibroin is in a range of 15:1 to 1:15.

5. The composition of claim 1, wherein the tyramine-substituted silk fibroin is created by a method comprising contacting a silk fibroin solution with tyramine hydrochloride in a presence of 1-ethyl-3-(-3-dimethylaminopropyl) carbodiimide hydrochloride and N-hydroxysuccinimide.

6. The composition of claim 1, further comprising at least one cyclic arginine-glycine-aspartic acid (RGD) peptide covalently linked to at least one phenol group of the tyramine-substituted silk fibroin.

7. The composition of claim 6, wherein the at least one cyclic RGD peptide is a cyclic arginine-glycine-aspartic acid-tyrosine-lysine peptide (cyclo(RGDyK) peptide).

8. The composition of claim 7, wherein the cyclo (RGDyK) peptide has a structure of formula I:

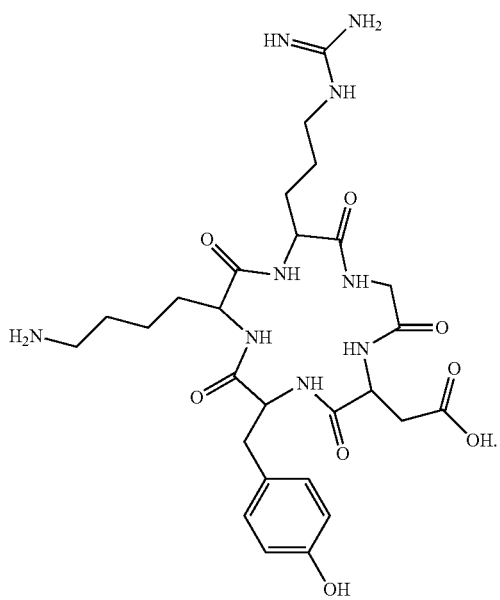

Formula I

9. The composition of claim 1, wherein the composition is or comprises a hydrogel.

10. The composition of claim 1, wherein the tyramine-substituted silk fibroin is present in an amount between 0.5 wt. % and 10 wt. % based on a total weight of the composition.

11. The composition of claim 3, wherein the unsubstituted silk fibroin is present in an amount between 0.5 wt. % and 10 wt. % based on total weight of the composition.

12. The composition of claim 1, wherein a total phenol content of the tyramine-substituted silk fibroin is at least 10% higher than total phenol content of unmodified unsubstituted silk fibroin.

13. The composition of claim 1, wherein a total phenol content of the tyramine-substituted silk fibroin is at least 5.5 mol %.

14. The composition of claim 6, wherein the at least one cyclic RGD peptide is present in an amount from 0.1 mM to about 1.0 mM.

15. The composition of claim 1, wherein the composition retains at least 30% of an original mass of the composition upon exposure to a protease over a degradation duration of at least 4 days.

16. The composition of claim 1, wherein the composition has a surface that has an area of cell spreading with a median value of at least 2000 $\mu m^2$ after 24 hours following positioning cells on the surface at a cell density of at least 1,000 cells/$cm^2$ in a growth medium.

17. The composition of claim 1, wherein the composition has a surface that has a fold change in metabolic activity of cells of at least 1.25 after at least 3 days following positioning cells on the surface a cell density of at least 1,000 cells/$cm^2$ in a growth medium.

18. The composition of claim 1, wherein the composition has a fold change in metabolic activity of encapsulated cells of less than 2.5 after at least 3 days following encapsulating cells in the composition comprising a growth medium, wherein the cells are present at an initial concentration of at least $1\times10^5$ cells/mL.

19. A composition comprising
unsubstituted silk fibroin; and
tyramine-substituted silk fibroin; wherein at least one tyrosine-group of the unsubstituted silk fibroin is covalently crosslinked to at least one phenol-group of the tyramine-substituted silk fibroin.

20. A composition comprising tyramine-substituted silk fibroin, wherein a first phenol group of the tyramine-substituted silk fibroin is covalently crosslinked to a second phenol group in the composition.

* * * * *